(12) United States Patent
Cutler et al.

(10) Patent No.: US 11,641,857 B2
(45) Date of Patent: May 9, 2023

(54) UNUSUALLY POTENT ABA RECEPTOR PAN-ANTAGONISTS

(71) Applicant: The Regents of the University of California, Oakand, CA (US)

(72) Inventors: Sean R. Cutler, Riverside, CA (US); Aditya Vaidya, Riverside, CA (US)

(73) Assignee: The Regents of The University of California, Oakland, CA (US)

( * ) Notice: Subject to any disclaimer, the term of this patent is extended or adjusted under 35 U.S.C. 154(b) by 89 days.

(21) Appl. No.: 16/906,765

(22) Filed: Jun. 19, 2020

(65) Prior Publication Data

US 2020/0397000 A1 Dec. 24, 2020

Related U.S. Application Data

(60) Provisional application No. 62/864,392, filed on Jun. 20, 2019.

(51) Int. Cl.

| | |
|---|---|
| *A01N 43/647* | (2006.01) |
| *C07D 249/06* | (2006.01) |
| *C07D 405/12* | (2006.01) |
| *C07D 401/12* | (2006.01) |
| *C07D 413/12* | (2006.01) |
| *C07D 403/12* | (2006.01) |

(52) U.S. Cl.
CPC ......... *A01N 43/647* (2013.01); *C07D 249/06* (2013.01); *C07D 401/12* (2013.01); *C07D 403/12* (2013.01); *C07D 405/12* (2013.01); *C07D 413/12* (2013.01)

(58) Field of Classification Search
CPC .. A01N 43/647; C07D 249/06; C07D 401/12; C07D 403/12
See application file for complete search history.

(56) References Cited

U.S. PATENT DOCUMENTS

| | | | |
|---|---|---|---|
| 9,173,395 B2 * | 11/2015 | Frackenpohl | A01N 43/38 |
| 9,345,245 B2 * | 5/2016 | Cutler | C07D 215/227 |
| 2011/0230350 A1 * | 9/2011 | Frackenpohl | A01N 43/42 |
| | | | 546/172 |

* cited by examiner

*Primary Examiner* — Kamal A Saeed

(74) *Attorney, Agent, or Firm* — Kilpatrick Townsend & Stockton LLP

(57) ABSTRACT

The present invention sets forth new compounds that potently block activation of ABA receptors. In some aspects, these compounds can be used to enhance germination of crop seeds to stand establishment and to increase transpiration and photosynthetic yields when water is not limiting plant growth.

19 Claims, 72 Drawing Sheets

Chemical Formula: $C_{30}H_{34}N_4O_3$
Exact Mass (M+H)$^+$ = 500.2886
RT(min): 14.223

| Ligand/Condition | PYR1 Mean ± S.D |
|---|---|
| DMSO | 100.0 ± 2.5 |
| ABA | 9.5 ± 1.3 |
| Pure triazole | 101.3 ± 1.8 |
| Pure triazole + ABA | 66.3 ± 6.8 |
| In situ triazole | 98.1 ± 0.6 |
| In situ triazole +ABA | 72.9 ± 1.8 |
| OPZ | 65.8 ± 3.2 |
| OPZ+ ABA | 51.1 ± 5.0 |
| CuSO4 (50 µM) | 92.9 ± 1.7 |
| BTTA (100 µM) | 93.8 ± 0.6 |
| Na ascorbate(100 µM) | 96.5 ± 0.9 |
| Click reagents-combination | 97.3 ± 1.0 |

| # | structure | Vendor ID | Click ID |
|---|---|---|---|
| 1 | 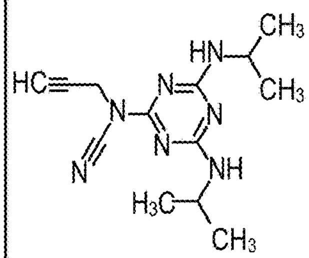 | BAS 01321692 | CLK001_F06 |
| 2 | 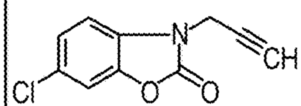 | BAS 00714775 | CLK001_H06 |
| 3 | 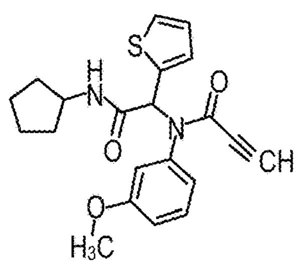 | ASN 06087882 | CLK003_A11 |
| 4 | 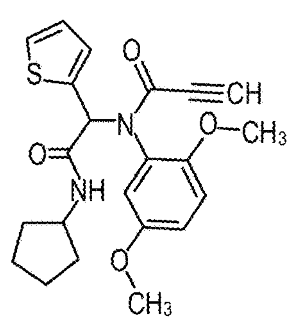 | ASN 06087944 | CLK003_B11 |

FIG. 4

| # | structure | Vendor ID | Click ID |
|---|---|---|---|
| 5 | 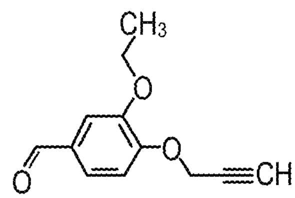 | BAS 06618269 | CLK003_F10 |
| 6 | 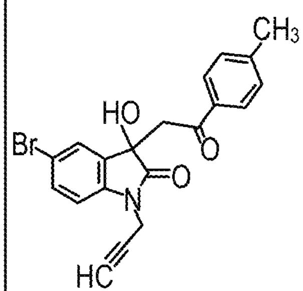 | BAS 04819281 | CLK003_G11 |
| 7 | 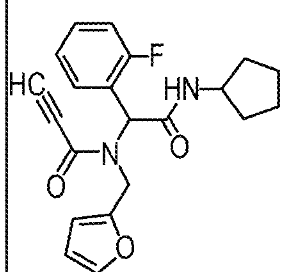 | ASN 06088251 | CLK004_B02 |
| 8 | 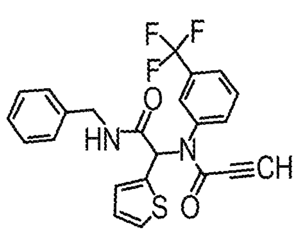 | ASN 06090454 | CLK004_C08 |

FIG. 4 (Cont'd)

| # | structure | Vendor ID | Click ID |
|---|---|---|---|
| 9 | 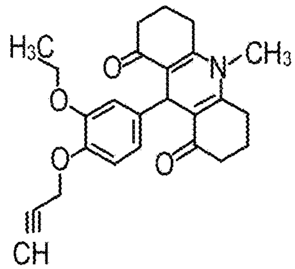 | BAS 04232970 | CLK005_B02 |
| 10 | 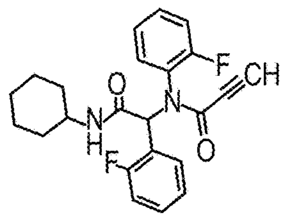 | ASN 06089493 | CLK005_E04 |
| 11 | 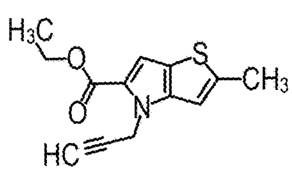 | ASN 08223902 | CLK005_E08 |
| 12 | 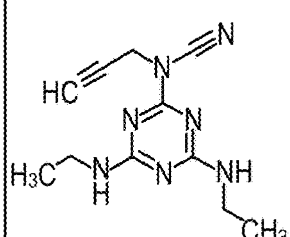 | BAS 01321688 | CLK005_E10 |

| # | structure | Vendor ID | Click ID |
|---|---|---|---|
| 13 | 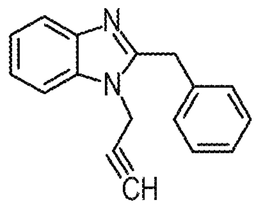 | BAS 11135971 | CLK005_F08 |
| 14 | 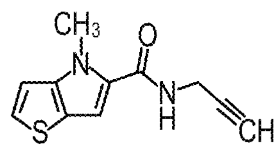 | ASN 06915234 | CLK005_F10 |
| 15 | 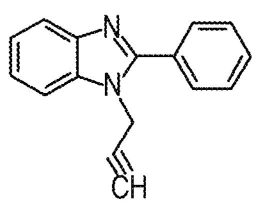 | BAS 11135972 | CLK006_A04 |
| 16 | 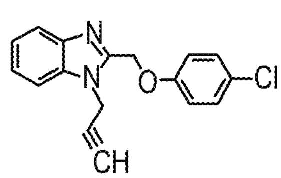 | BAS 11136195 | CLK006_A05 |

| # | structure | Vendor ID | Click ID |
|---|---|---|---|
| 17 | 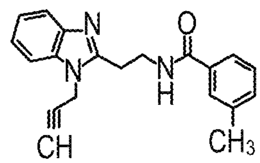 | BAS 11721778 | CLK006_A06 |
| 18 | 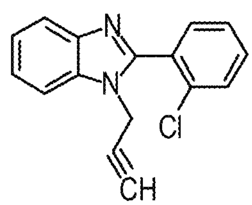 | BAS 11136000 | CLK006_B04 |
| 19 | 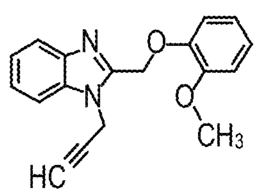 | BAS 11136246 | CLK006_B05 |
| 20 | 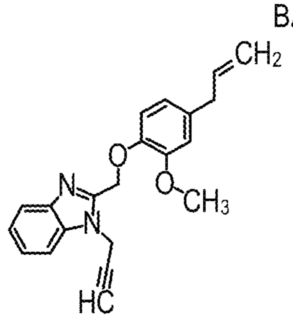 | BAS 11787642 | CLK006_B06 |

FIG. 4 (Cont'd)

| # | structure | Vendor ID | Click ID |
|---|---|---|---|
| 21 | 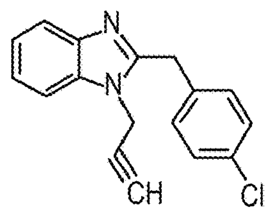 | BAS 11135457 | CLK006_B08 |
| 22 | 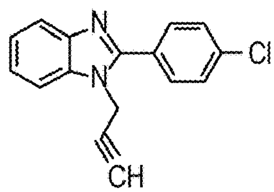 | BAS 11136025 | CLK006_C04 |
| 23 | 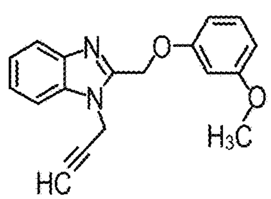 | BAS 11136271 | CLK006_C05 |
| 24 | 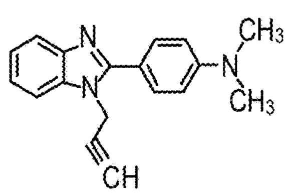 | BAS 11136039 | CLK006_D04 |

| # | structure | Vendor ID | Click ID |
|---|---|---|---|
| 25 | 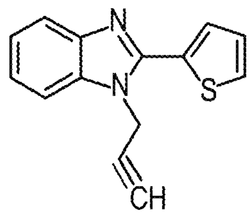 | BAS 11136349 | CLK006_D05 |
| 26 | 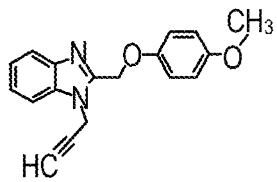 | BAS 11136247 | CLK006_D08 |
| 27 | 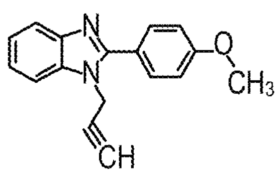 | BAS 11136065 | CLK006_E04 |
| 28 | 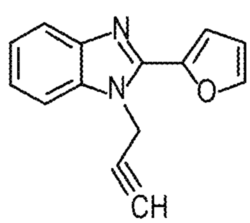 | BAS 11136350 | CLK006_E05 |

| # | structure | Vendor ID | Click ID |
|---|---|---|---|
| 29 | 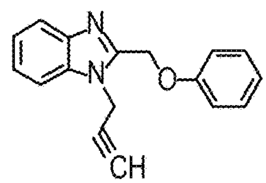 | BAS 11136169 | CLK006_G04 |
| 30 | 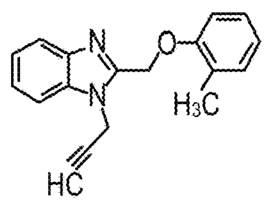 | BAS 11136221 | CLK007_A06 |
| 31 | 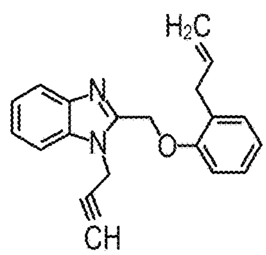 | BAS 13175024 | CLK007_C09 |
| 32 | 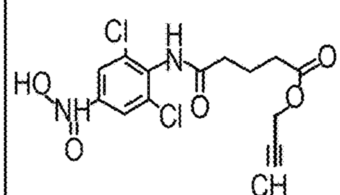 | 5152433 | CLK009_D04 |

| # | structure | Vendor ID | Click ID |
|---|---|---|---|
| 33 | 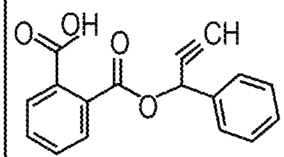 | 5105989 | CLK009_E02 |
| 34 | 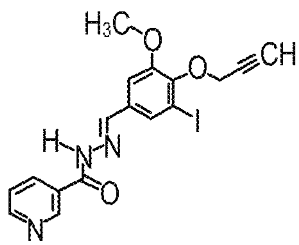 | 5665633 | CLK009_F10 |
| 35 | 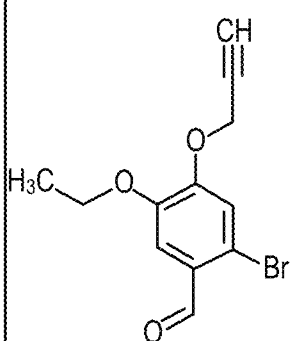 | 6566086 | CLK013_H04 |
| 36 | 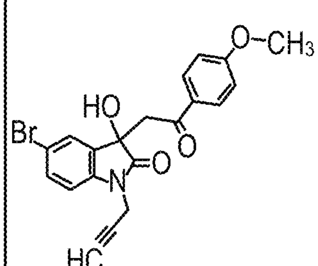 | 7406206 | CLK018_D05 |

FIG. 4 (Cont'd)

| # | structure | Vendor ID | Click ID |
|---|---|---|---|
| 37 | 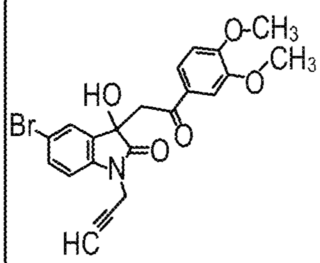 | 7389441 | CLK018_F04 |
| 38 | 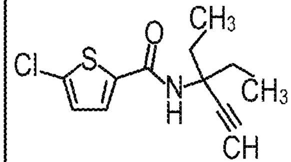 | 7947566 | CLK021_A02 |
| 39 | 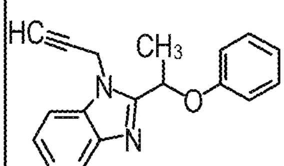 | 7998282 | CLK021_C08 |
| 40 | 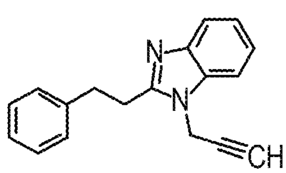 | 9003806 | CLK021_C09 |

FIG. 4 (Cont'd)

| # | structure | Vendor ID | Click ID |
|---|---|---|---|
| 41 | 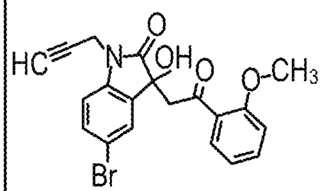 | 7968091 | CLK021_D04 |
| 42 | 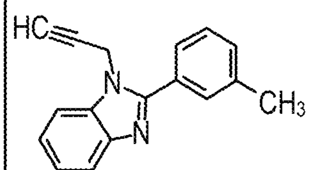 | 7998911 | CLK021_D08 |
| 43 | 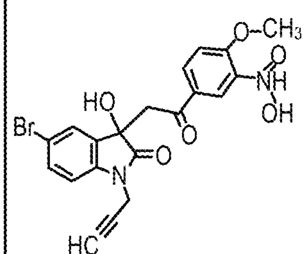 | STK214627 | CLK025_B07 |
| 44 | 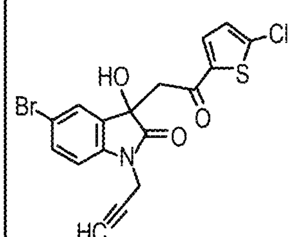 | STK214630 | CLK025_D07 |

| # | structure | Vendor ID | Click ID |
|---|---|---|---|
| 45 | 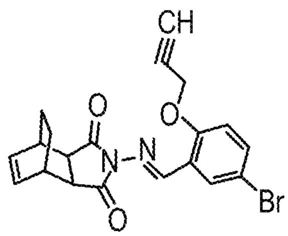 | STK281889 | CLK025_F02 |
| 46 | 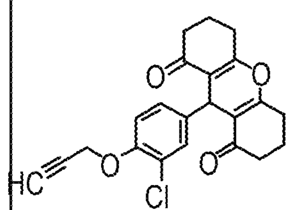 | F0660-0389 | CLK029_A05 |
| 47 | 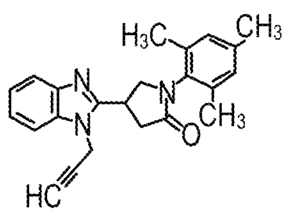 | F0660-1369 | CLK029_A06 |
| 48 | 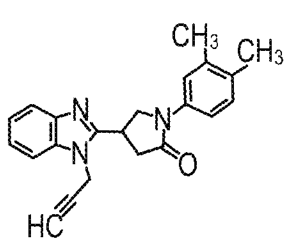 | F0660-0585 | CLK029_B05 |

| # | structure | Vendor ID | Click ID |
|---|---|---|---|
| 49 | 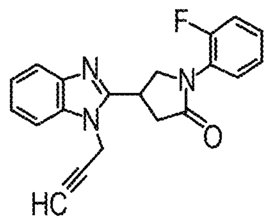 | F0660-1565 | CLK029_B06 |
| 50 | 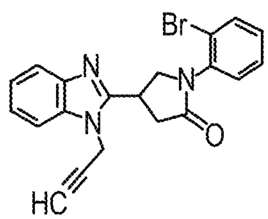 | F0660-1761 | CLK029_C06 |
| 51 | 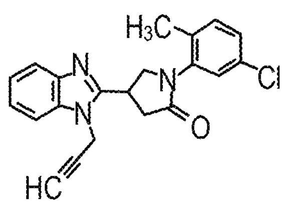 | F0660-0781 | CLK029_D05 |
| 52 | 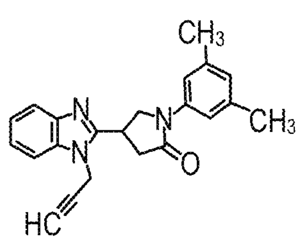 | F0660-2153 | CLK029_D06 |

| # | structure | Vendor ID | Click ID |
|---|---|---|---|
| 53 | 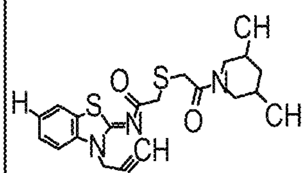 | F0620-1898 | CLK029_E04 |
| 54 | 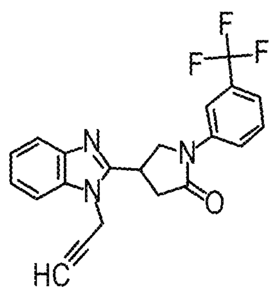 | F0660-0879 | CLK029_E05 |
| 55 | 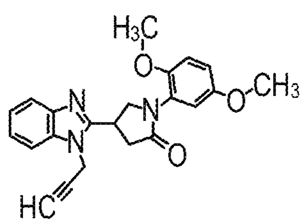 | F0660-2251 | CLK029_E06 |
| 56 | 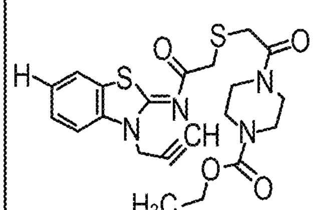 | F0620-1882 | CLK029_F03 |

FIG. 4 (Cont'd)

| # | structure | Vendor ID | Click ID |
|---|---|---|---|
| 57 | 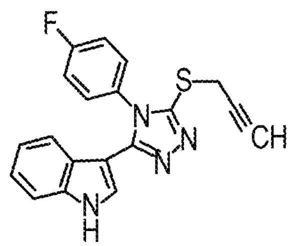 | F0653-0770 | CLK029_F04 |
| 58 | 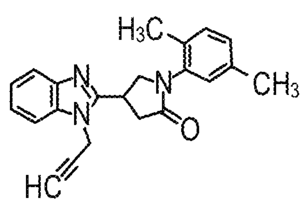 | F0660-1075 | CLK029_F05 |
| 59 | 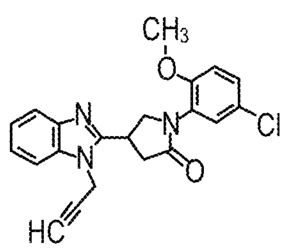 | F0660-2447 | CLK029_F06 |
| 60 | 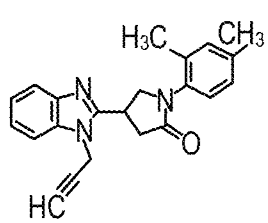 | F0660-0193 | CLK029_G04 |

FIG. 4 (Cont'd)

| # | structure | Vendor ID | Click ID |
|---|---|---|---|
| 61 | 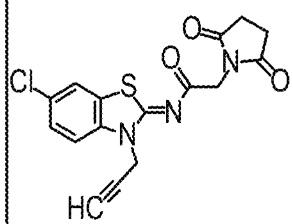 | F1365-2352 | CLK029_G11 |
| 62 | 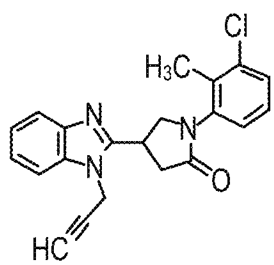 | F0660-0291 | CLK029_H04 |
| 63 | 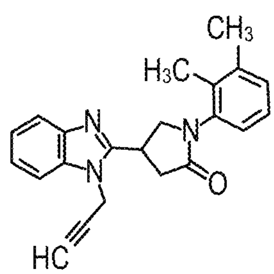 | F0660-1271 | CLK029_H05 |
| 64 | 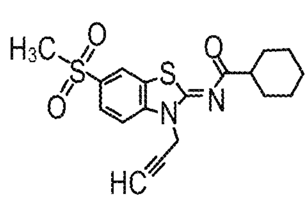 | F1365-2819 | CLK030_D07 |

| # | structure | Vendor ID | Click ID |
|---|---|---|---|
| 65 | 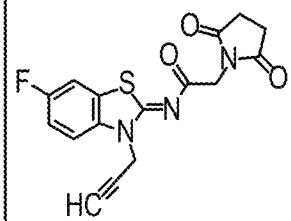 | F1365-2616 | CLK030_F05 |
| 66 | 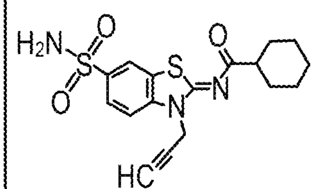 | F1365-2951 | CLK031_E03 |
| 67 | 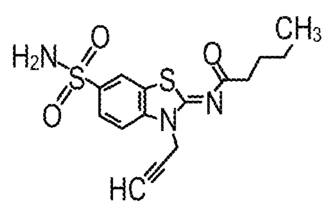 | F1365-2993 | CLK031_F07 |
| 68 | 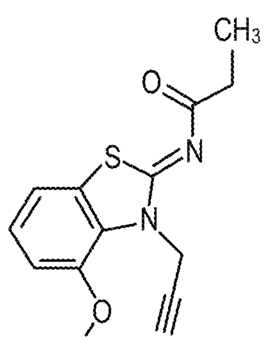 | F1816-0952 | CLK034_F10 |

| # | structure | Vendor ID | Click ID |
|---|---|---|---|
| 69 | 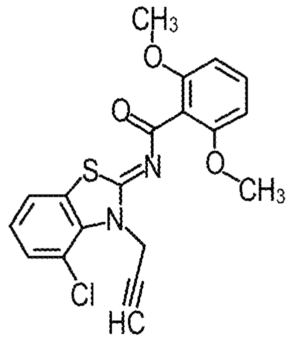 | F1816-1220 | CLK035_D06 |
| 70 | 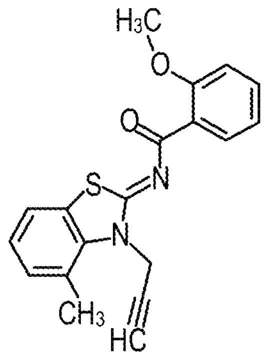 | F1816-1053 | CLK035_G03 |
| 71 | 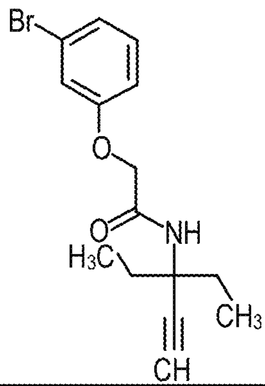 | T5303593 | CLK037A03 |
| 72 | 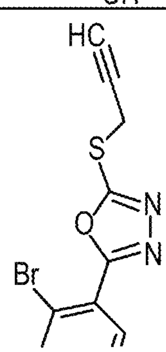 | T5245539 | CLK037B02 |

| # | structure | Vendor ID | Click ID |
|---|---|---|---|
| 73 | 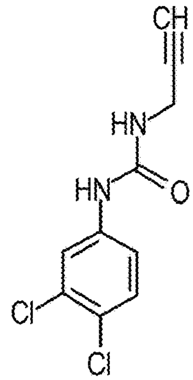 | T5338958 | CLK037B04 |
| 74 | 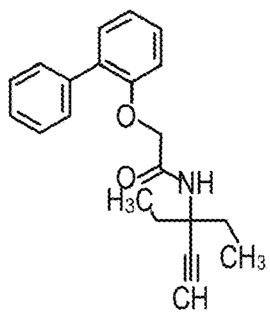 | T5684501 | CLK037B06 |
| 75 | 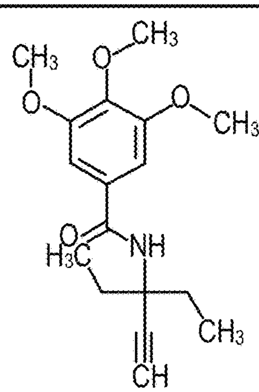 | T5251597 | CLK037C02 |
| 76 | 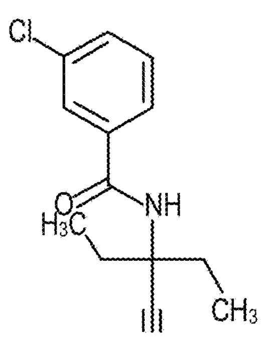 | T5346274 | CLK037D05 |

| # | structure | Vendor ID | Click ID |
|---|---|---|---|
| 77 | 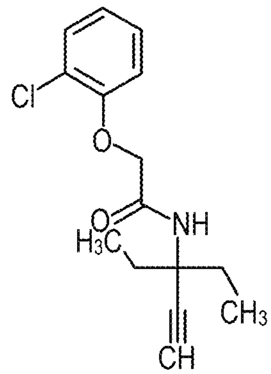 | T5361568 | CLK037D06 |
| 78 | 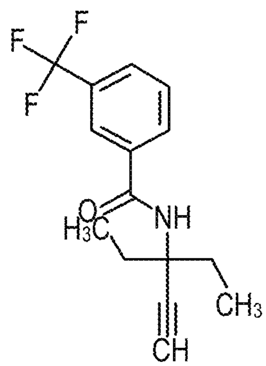 | T5318013 | CLK037F03 |
| 79 | 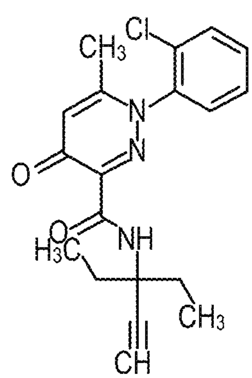 | T5501753 | CLK037F10 |
| 80 | 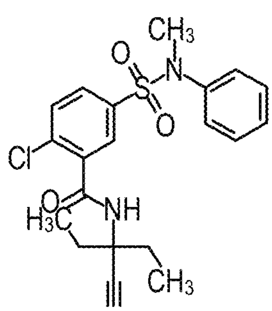 | T5340795 | CLK037G04 |

| # | structure | Vendor ID | Click ID |
|---|---|---|---|
| 81 | 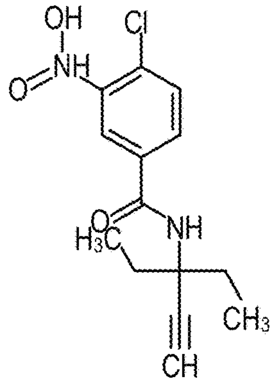 | T5348233 | CLK037G05 |
| 82 | 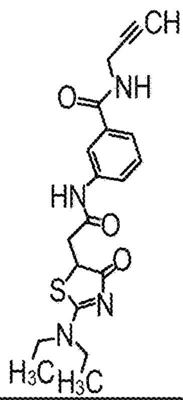 | T5504536 | CLK037G10 |
| 83 | 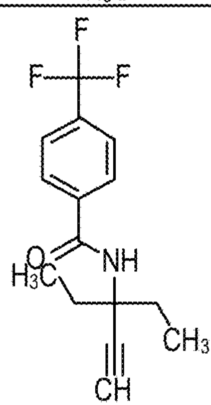 | T5302162 | CLK037H02 |
| 84 | 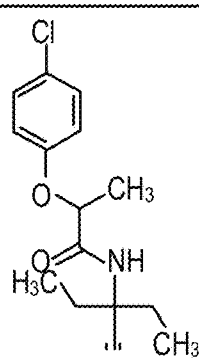 | T5482330 | CLK038A02 |

FIG. 4 (Cont'd)

| # | structure | Vendor ID | Click ID |
|---|---|---|---|
| 85 | 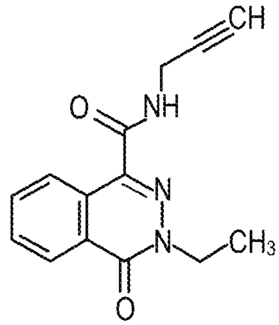 | T5634471 | CLK038B08 |
| 86 | 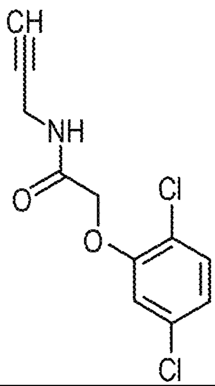 | T5674813 | CLK039A06 |
| 87 | 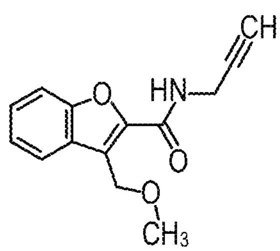 | T5682518 | CLK039A10 |
| 88 | 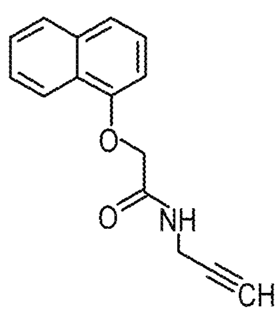 | T5677217 | CLK039C07 |

| # | structure | Vendor ID | Click ID |
|---|---|---|---|
| 89 | 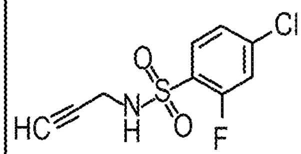 | T5673745 | CLK039E04 |
| 90 | 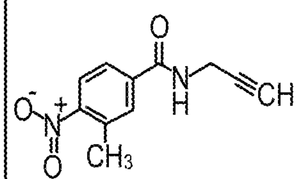 | T5674360 | CLK039E05 |
| 91 | 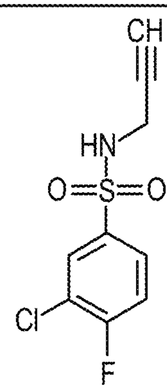 | T5673752 | CLK039G04 |
| 92 | 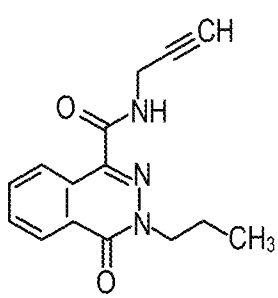 | T5674787 | CLK039G05 |

| # | structure | Vendor ID | Click ID |
|---|---|---|---|
| 93 | 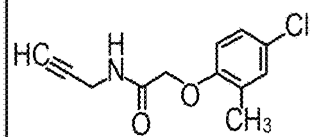 | T5677213 | CLK039H06 |
| 94 | 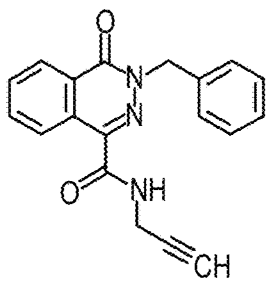 | T5699614 | CLK040A04 |
| 95 | 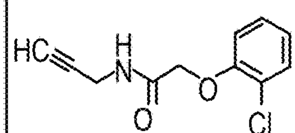 | T5700007 | CLK040B04 |
| 96 | 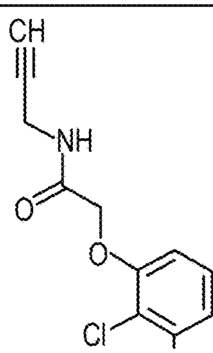 | T5696063 | CLK040D03 |

| # | structure | Vendor ID | Click ID |
|---|---|---|---|
| 97 | 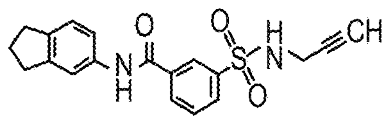 | T5814547 | CLK041A09 |
| 98 | 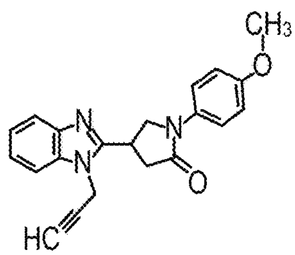 | T5816145 | CLK041A10 |
| 99 | 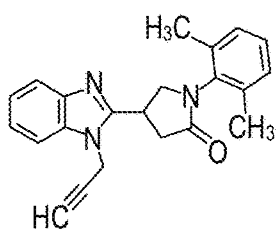 | T5816888 | CLK041B10 |
| 100 | 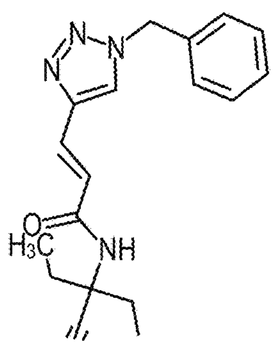 | T5760990 | CLK041D03 |

| # | structure | Vendor ID | Click ID |
|---|---|---|---|
| 101 | 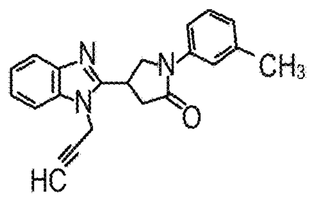 | T5815669 | CLK041F09 |
| 102 | 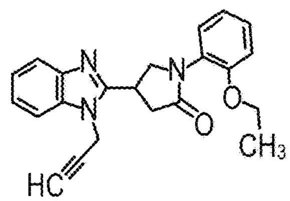 | T5814795 | CLK041G08 |
| 103 | 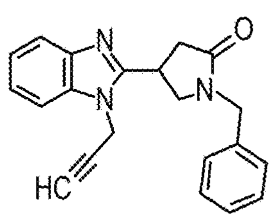 | T5815734 | CLK041G09 |
| 104 | 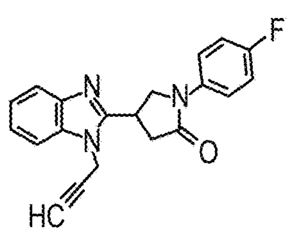 | T5814797 | CLK041H08 |

| # | structure | Vendor ID | Click ID |
|---|---|---|---|
| 105 | 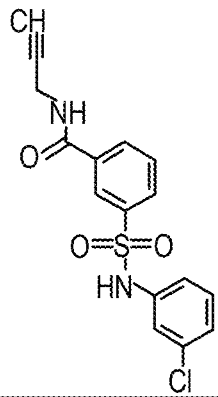 | T5837887 | CLK042A03 |
| 106 | 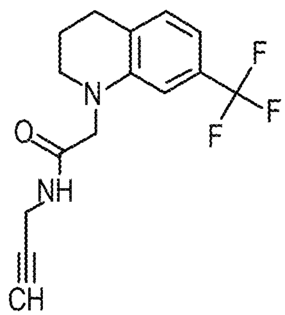 | T5906009 | CLK042D11 |
| 107 | 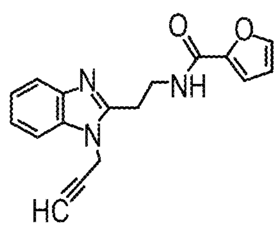 | T5840791 | CLK042F03 |
| 108 | 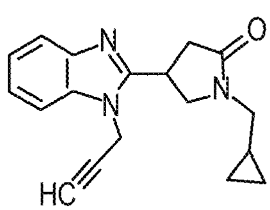 | T5845211 | CLK042F04 |

FIG. 4 (Cont'd)

| # | structure | Vendor ID | Click ID |
|---|---|---|---|
| 109 | 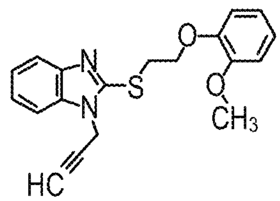 | T5845235 | CLK042G04 |
| 110 | 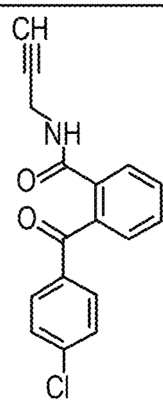 | T5973408 | CLK043F07 |
| 111 | 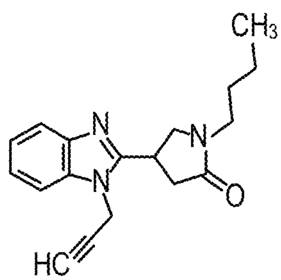 | T6017115 | CLK044A03 |
| 112 | 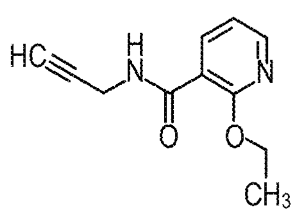 | T6051328 | CLK044E07 |

| # | structure | Vendor ID | Click ID |
|---|---|---|---|
| 113 | 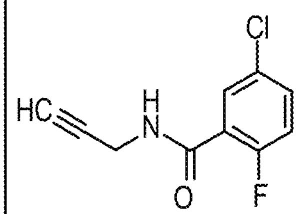 | T6052793 | CLK044F08 |
| 114 | 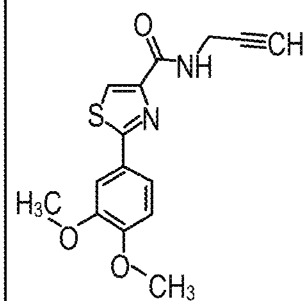 | T6042228 | CLK044G05 |
| 115 | 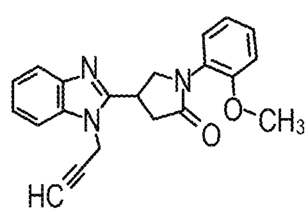 | T6015972 | CLK044H02 |
| 116 | 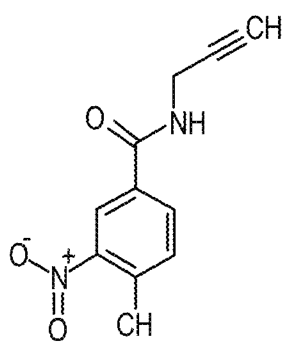 | T6049165 | CLK044H06 |

| # | structure | Vendor ID | Click ID |
|---|---|---|---|
| 117 | 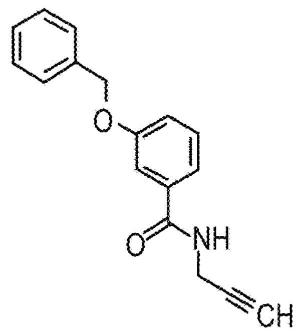 | T6074787 | CLK045D04 |
| 118 | 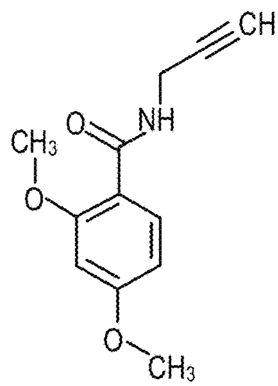 | T6079930 | CLK045G04 |
| 119 | 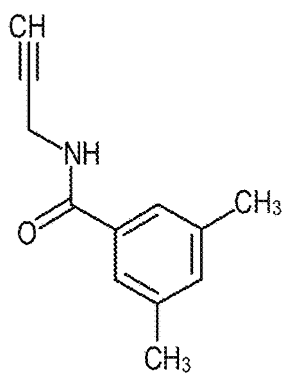 | T6134740 | CLK046C11 |
| 120 | 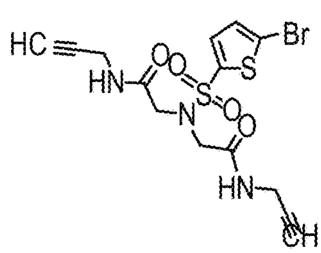 | T6126236 | CLK046D07 |

| # | structure | Vendor ID | Click ID |
|---|---|---|---|
| 121 | 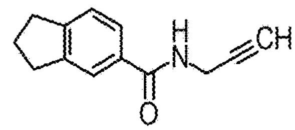 | T6131938 | CLK046F09 |
| 122 | 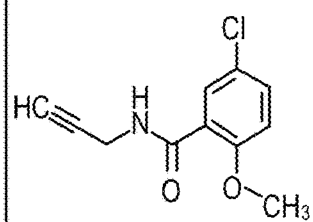 | T6247294 | CLK046G11 |
| 123 | 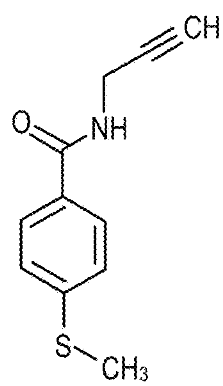 | T6133232 | CLK046H09 |
| 124 | 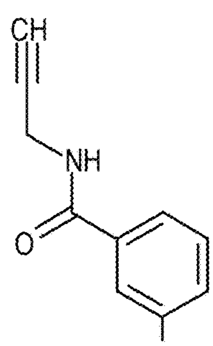 | T6136299 | CLK046H11 |

| # | structure | Vendor ID | Click ID |
|---|---|---|---|
| 125 | 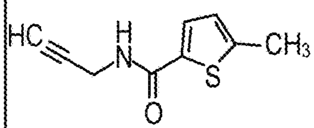 | T6136477 | CLK047A02 |
| 126 | 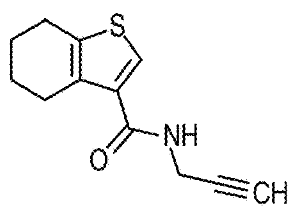 | T6138073 | CLK047A04 |
| 127 | 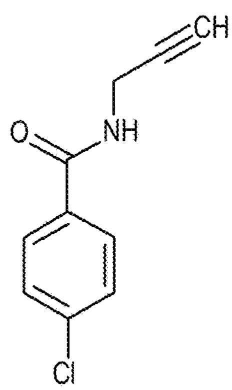 | T6136478 | CLK047B02 |
| 128 | 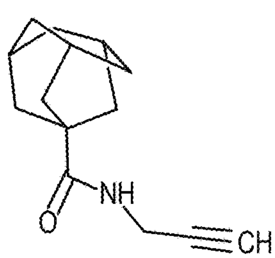 | T6143738 | CLK047B06 |

| # | structure | Vendor ID | Click ID |
|---|---|---|---|
| 129 | 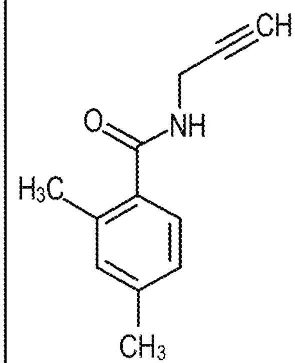 | T6136575 | CLK047C02 |
| 130 | 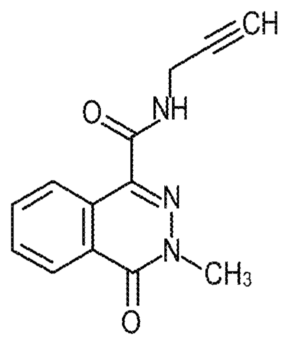 | T6137000 | CLK047C03 |
| 131 | 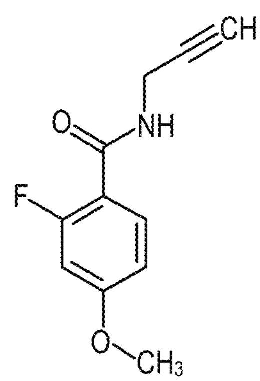 | T6142267 | CLK047C05 |
| 132 | 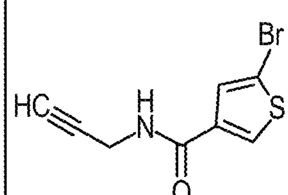 | T6144812 | CLK047C07 |

| # | structure | Vendor ID | Click ID |
|---|---|---|---|
| 133 | 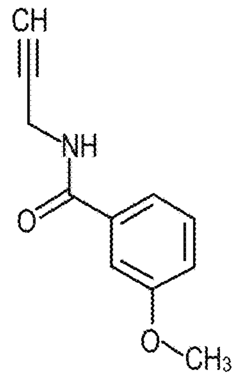 | T6146879 | CLK047C09 |
| 134 | 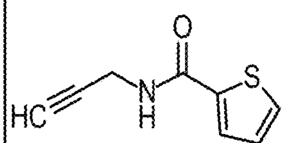 | T6137031 | CLK047D03 |
| 135 | 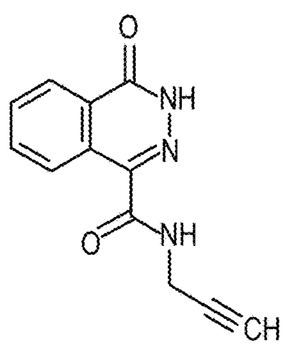 | T6136814 | CLK047E02 |
| 136 | 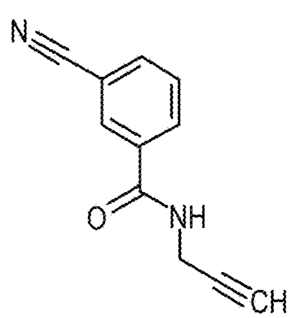 | T6137033 | CLK047E03 |

| # | structure | Vendor ID | Click ID |
|---|---|---|---|
| 137 | 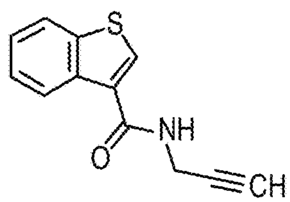 | T6143956 | CLK047E06 |
| 138 | 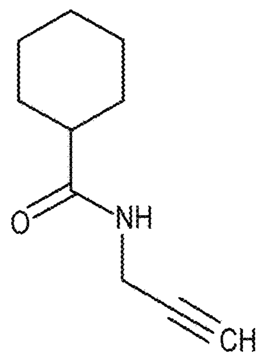 | T6145541 | CLK047E07 |
| 139 | 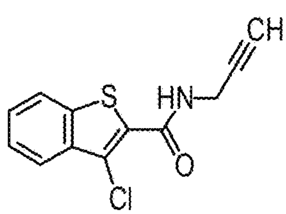 | T6146370 | CLK047E08 |
| 140 | 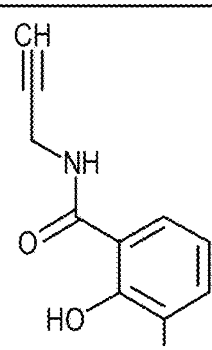 | T6150835 | CLK047E10 |

| # | structure | Vendor ID | Click ID |
|---|---|---|---|
| 141 | 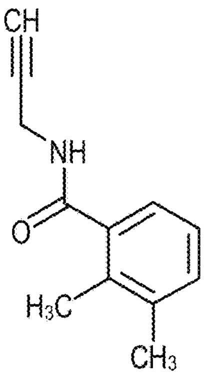 | T6136843 | CLK047F02 |
| 142 | 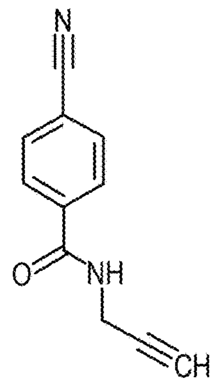 | T6137053 | CLK047F03 |
| 143 | 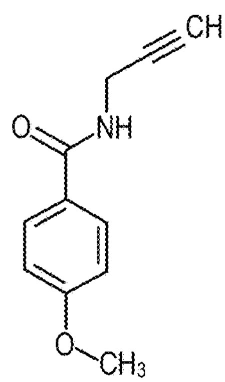 | T6136845 | CLK047G02 |
| 144 | 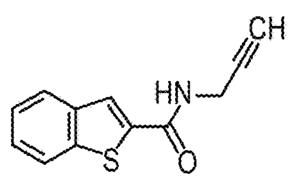 | T6137576 | CLK047G03 |

| # | structure | Vendor ID | Click ID |
|---|---|---|---|
| 145 | (3,4-dimethyl-N-(prop-2-yn-1-yl)benzamide structure) | T6149865 | CLK047G11 |
| 146 | (4-bromo-N-(prop-2-yn-1-yl)benzamide structure) | T6136949 | CLK047H02 |
| 147 | (2,3-dihydrobenzothiophene-2-carboxamide N-propargyl structure) | T6137982 | CLK047H03 |
| 148 | (4-methyl-N-(prop-2-yn-1-yl)picolinamide structure) | T6149989 | CLK048A02 |

FIG. 4 (Cont'd)

| # | structure | Vendor ID | Click ID |
|---|---|---|---|
| 149 | 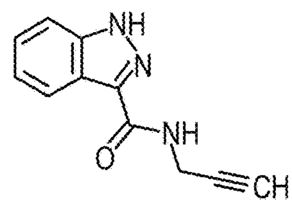 | T6153234 | CLK048A03 |
| 150 | 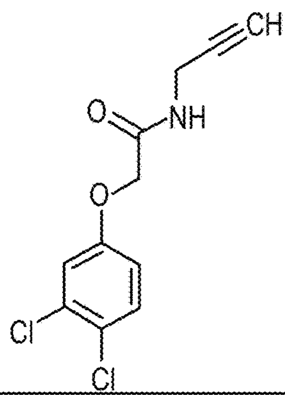 | T6154797 | CLK048A04 |
| 151 | 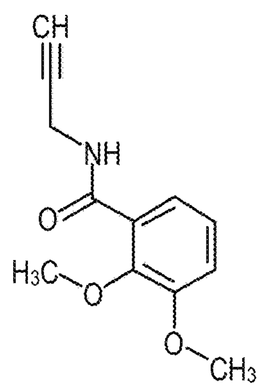 | T6160253 | CLK048A06 |
| 152 | 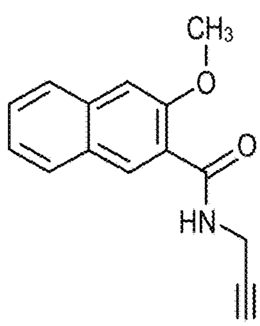 | T6159205 | CLK048A07 |

| # | structure | Vendor ID | Click ID |
|---|---|---|---|
| 153 | 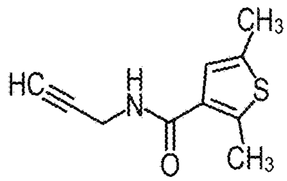 | T6167001 | CLK048A11 |
| 154 | 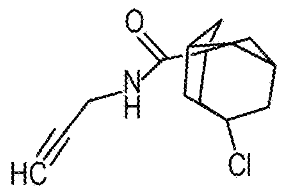 | T6151274 | CLK048B02 |
| 155 | 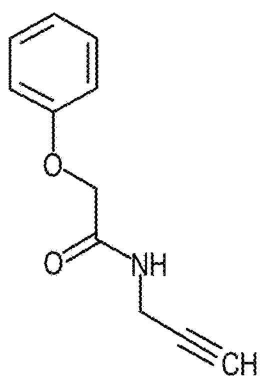 | T6156885 | CLK048B04 |
| 156 | 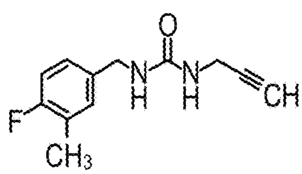 | T6159394 | CLK048B07 |

FIG. 4 (Cont'd)

| # | structure | Vendor ID | Click ID |
|---|---|---|---|
| 157 | 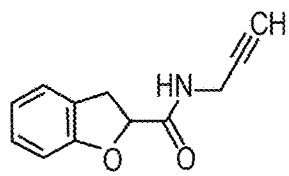 | T6163535 | CLK048B09 |
| 158 | 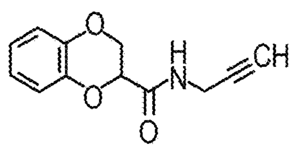 | T6160827 | CLK048C06 |
| 159 | 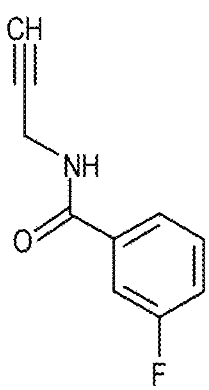 | T6163537 | CLK048C09 |
| 160 | 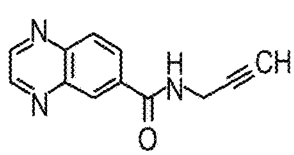 | T6165055 | CLK048C10 |

| # | structure | Vendor ID | Click ID |
|---|---|---|---|
| 161 | 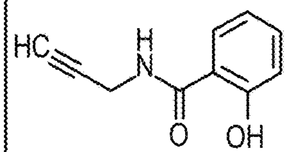 | T6167053 | CLK048C11 |
| 162 | 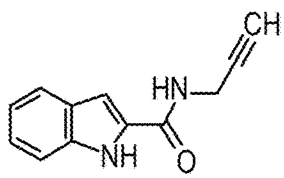 | T6154156 | CLK048D03 |
| 163 | 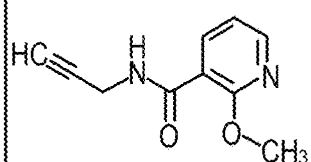 | T6159604 | CLK048D07 |
| 164 | 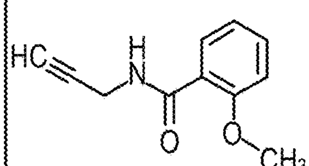 | T6167319 | CLK048D11 |

| # | structure | Vendor ID | Click ID |
|---|---|---|---|
| 165 | 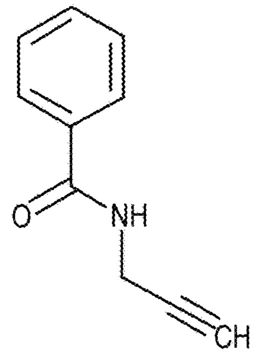 | T6154158 | CLK048E03 |
| 166 | 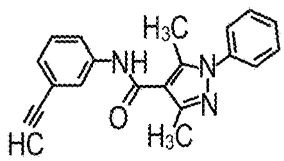 | T6163215 | CLK048E08 |
| 167 | 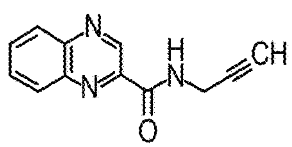 | T6163697 | CLK048E09 |
| 168 | 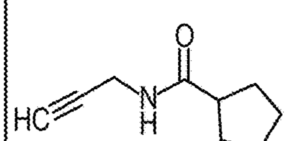 | T6152994 | CLK048F02 |

| # | structure | Vendor ID | Click ID |
|---|---|---|---|
| 169 | 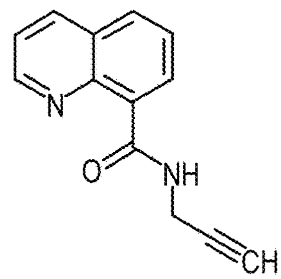 | T6154173 | CLK048F03 |
| 170 | 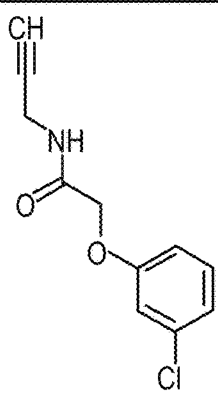 | T6165769 | CLK048F10 |
| 171 | 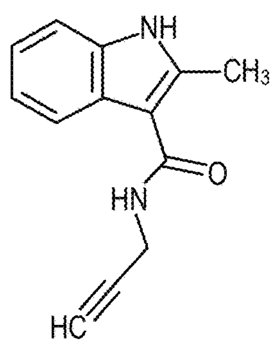 | T6154230 | CLK048G03 |
| 172 | 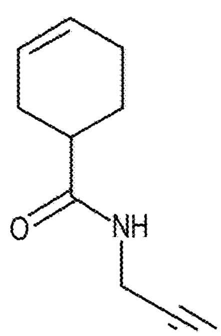 | T6163238 | CLK048G08 |

| # | structure | Vendor ID | Click ID |
|---|---|---|---|
| 173 | 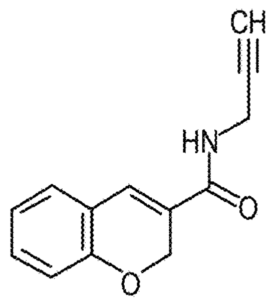 | T6164999 | CLK048H09 |
| 174 | 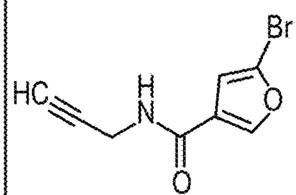 | T6164239 | CLK049A02 |
| 175 | 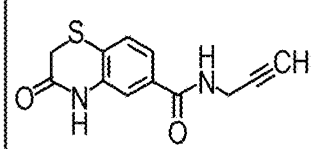 | T6179175 | CLK049A09 |
| 176 | 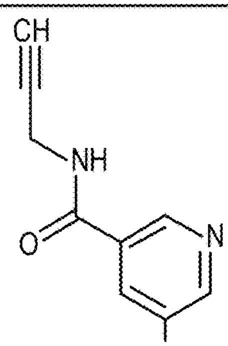 | T6164307 | CLK049B02 |

| # | structure | Vendor ID | Click ID |
|---|---|---|---|
| 177 | 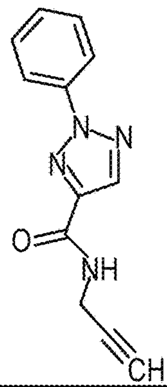 | T6164332 | CLK049C02 |
| 178 | 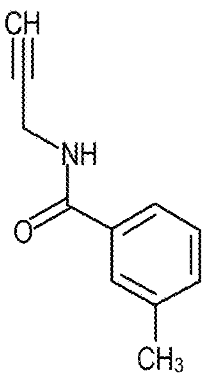 | T6180437 | CLK049C07 |
| 179 | 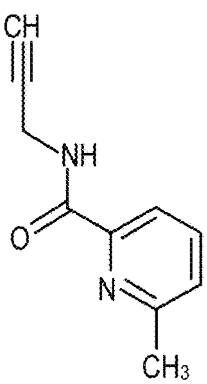 | T6183277 | CLK049E10 |
| 180 | 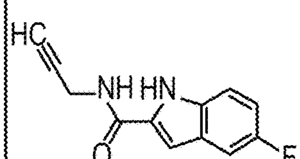 | T6164560 | CLK049E02 |

FIG. 4 (Cont'd)

| # | structure | Vendor ID | Click ID |
|---|---|---|---|
| 181 | 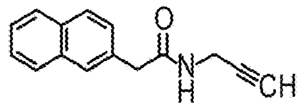 | T6181646 | CLK049E09 |
| 182 | 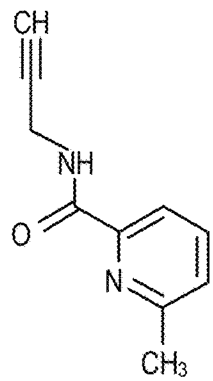 | T6183277 | CLK049E10 |
| 183 | 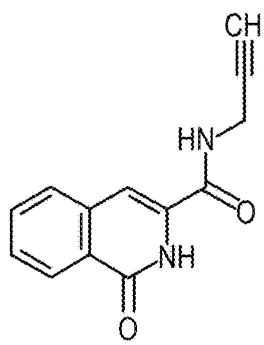 | T6180238 | CLK049F06 |
| 184 | 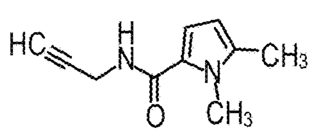 | T6183308 | CLK049F10 |

| # | structure | Vendor ID | Click ID |
|---|---|---|---|
| 185 | 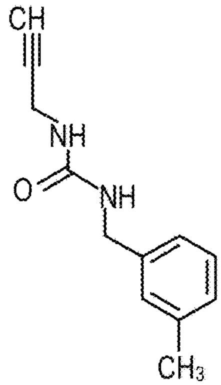 | T6185930 | CLK050A03 |
| 186 | 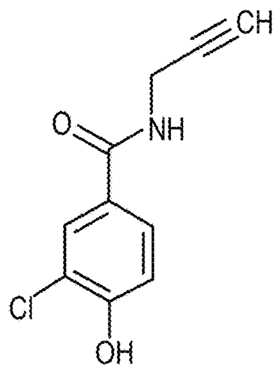 | T6189082 | CLK050A04 |
| 187 | 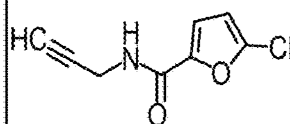 | T6195297 | CLK050A06 |
| 188 | 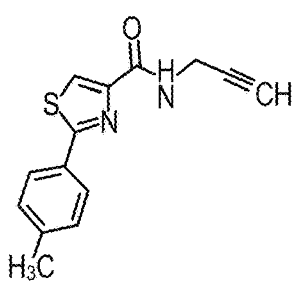 | T6197802 | CLK050B08 |

FIG. 4 (Cont'd)

| # | structure | Vendor ID | Click ID |
|---|---|---|---|
| 189 | 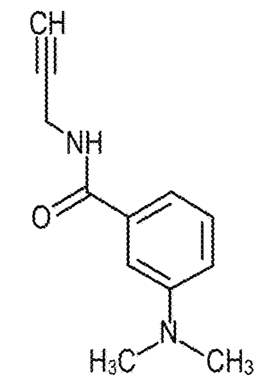 | T6202871 | CLK050B10 |
| 190 | 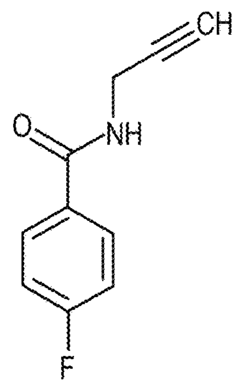 | T6194208 | CLK050C05 |
| 191 | 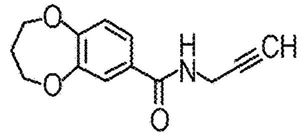 | T6223558 | CLK050C08 |
| 192 | 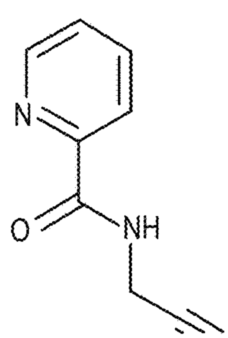 | T6203512 | CLK050C10 |

| # | structure | Vendor ID | Click ID |
|---|---|---|---|
| 193 | 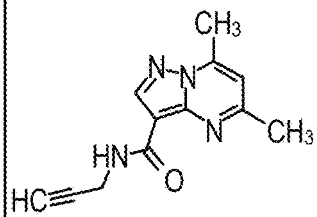 | T6201525 | CLK050D11 |
| 194 | 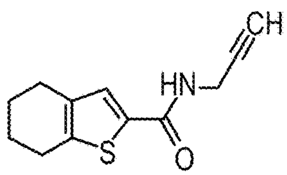 | T6199844 | CLK050E09 |
| 195 | 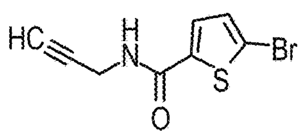 | T6195260 | CLK050G05 |
| 196 | 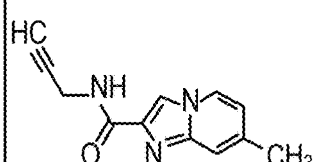 | T6199896 | CLK050G09 |

| # | structure | Vendor ID | Click ID |
|---|---|---|---|
| 197 | 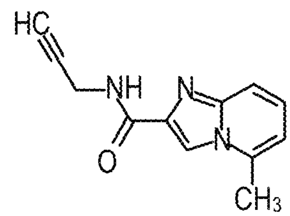 | T6199914 | CLK050H09 |
| 198 | 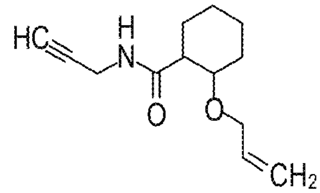 | T6212481 | CLK051H02 |
| 199 | 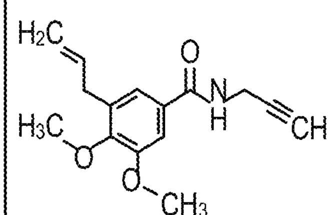 | T6248551 | CLK052A02 |
| 200 | 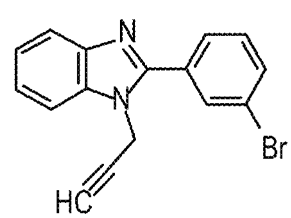 | T5444987 | CLK052G05 |

| # | structure | Vendor ID | Click ID |
|---|---|---|---|
| 201 | 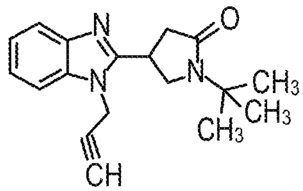 | BAS 11787974 | CLK008_C02 |
| 202 | 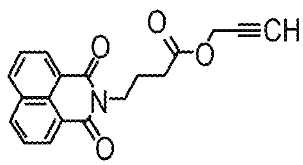 | ASN 12291324 | CLK008_C05 |
| 203 | 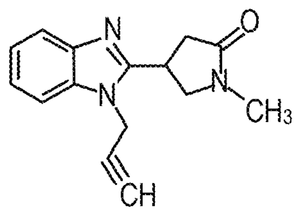 | ASN 12292402 | CLK008_D02 |
| 204 | 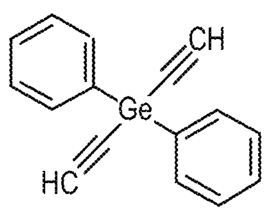 | ASN 12291912 | CLK008_E05 |

| ClickID | VendorID | Hit plate no | Well ID | PYR1 | PYL4 | PYL8 | conversion | % Greening |
|---|---|---|---|---|---|---|---|---|
| CLK001_F06 | BAS 01321692 | 1 | A2 | 77.3 | 69.7 | 69.6 | 1.00 | 14.3 |
| CLK001_H06 | BAS 00714775 | 1 | B2 | 83.9 | 58.9 | 90.1 | 1.00 | 43.8 |
| CLK003_A11 | ASN 06087882 | 1 | C2 | 73.5 | 77.3 | 74.4 | 0.94 | 2.9 |
| CLK003_B11 | ASN 06087944 | 1 | D2 | 64.6 | 55.3 | 71.9 | 0.97 | 0.3 |
| CLK003_F10 | BAS 06618269 | 1 | E2 | 64.8 | 18.4 | 14.4 | 1.00 | 0.0 |
| CLK003_G11 | BAS 04819281 | 1 | F2 | 57.6 | 43.2 | 16.3 | 0.75 | 0.5 |
| CLK004_B03 | ASN 06088251 | 1 | G2 | 73.3 | 69.3 | 84.5 | 0.95 | 0.1 |
| CLK004_C08 | ASN 06090454 | 1 | H2 | 52.2 | 52.6 | 30.1 | 0.88 | 0.0 |
| CLK005_B02 | BAS 04232970 | 1 | A3 | 69.8 | 38.9 | 24.1 | 1.00 | 0.0 |
| CLK005_E04 | ASN 06085493 | 1 | B3 | 75.5 | 86.9 | 80.5 | 0.92 | 17.9 |
| CLK005_E08 | ASN 08323902 | 1 | C3 | 46.4 | 36.0 | 16.5 | 1.00 | 24.1 |
| CLK005_E10 | BAS 01321688 | 1 | D3 | 55.5 | 80.3 | 61.3 | 0.99 | 37.2 |
| CLK005_F08 | BAS 11135971 | 1 | E3 | 46.0 | 14.7 | 12.1 | 1.00 | 0.0 |
| CLK005_F10 | ASN 06915234 | 1 | F3 | 64.6 | 88.8 | 68.2 | 1.00 | 85.2 |
| CLK006_A04 | BAS 11135972 | 1 | G3 | 65.9 | 2.3 | 10.4 | 1.00 | 0.0 |
| CLK006_A05 | BAS 11136195 | 1 | H3 | 71.5 | 24.5 | 9.0 | 0.84 | 0.0 |
| CLK006_A06 | BAS 11721778 | 1 | A4 | 67.6 | 33.6 | 24.9 | 1.00 | 0.0 |
| CLK006_B04 | BAS 11136000 | 1 | B4 | 52.8 | 7.5 | 11.0 | 0.89 | 1.0 |
| CLK006_B05 | BAS 11136246 | 1 | C4 | 67.5 | 24.4 | 10.2 | 0.90 | 1.3 |
| CLK006_B06 | BAS 11787642 | 1 | D4 | 55.6 | 33.1 | 13.4 | 0.75 | 2.1 |
| CLK006_B08 | BAS 11135457 | 1 | E4 | 48.9 | 13.0 | 6.8 | 0.85 | 4.7 |
| CLK006_C04 | BAS 11136025 | 1 | F4 | 59.7 | 8.1 | 12.3 | 0.82 | 0.2 |
| CLK006_C05 | BAS 11136271 | 1 | G4 | 67.0 | 20.0 | 12.8 | 0.98 | 0.0 |
| CLK006_D04 | BAS 11136039 | 1 | H4 | 74.1 | 29.8 | 16.2 | 0.92 | 0.0 |
| CLK006_D05 | BAS 11136349 | 1 | A5 | 26.7 | -4.4 | 12.0 | 1.00 | 0.0 |
| CLK006_D08 | BAS 11136247 | 1 | B5 | 54.9 | 23.0 | 14.8 | 0.76 | 1.7 |
| CLK006_E04 | BAS 11136065 | 1 | C5 | 74.2 | 11.4 | 6.6 | 0.73 | 3.0 |
| CLK006_E05 | BAS 11136350 | 1 | D5 | 35.7 | 6.1 | 10.9 | 1.00 | 0.0 |
| CLK006_G04 | BAS 11136169 | 1 | E5 | 66.2 | 12.3 | 8.6 | 0.78 | 5.0 |
| CLK007_A06 | BAS 11136221 | 1 | F5 | 62.0 | 15.5 | 12.7 | 0.79 | 0.0 |
| CLK007_C09 | BAS 13175024 | 1 | G5 | 73.6 | 25.2 | 10.2 | 1.00 | 0.0 |
| CLK009_D04 | 5152433 | 1 | H5 | 61.8 | 57.0 | 96.1 | 0.83 | 0.3 |
| CLK009_E02 | 5105989 | 1 | A6 | 50.8 | 65.3 | 52.6 | 1.00 | 4.3 |
| CLK009_F10 | 5665633 | 1 | B6 | 66.0 | 49.1 | 57.6 | 0.77 | 22.2 |
| CLK013_H04 | 6566086 | 1 | C6 | 59.1 | 23.0 | 12.9 | 0.80 | 3.1 |
| CLK018_D05 | 7406106 | 1 | D6 | 95.6 | 17.0 | 15.8 | 0.79 | 13.9 |
| CLK018_F04 | 7389441 | 1 | E6 | 94.4 | 26.8 | 12.0 | 0.64 | 6.3 |
| CLK021_A02 | 7947566 | 1 | F6 | 14.3 | 6.6 | 10.5 | 0.63 | 112.4 |
| CLK021_C08 | 7998282 | 1 | G6 | 75.4 | 6.4 | 7.2 | 0.51 | 2.8 |
| CLK021_C09 | 9003806 | 1 | H6 | 89.9 | 13.9 | 10.3 | 0.97 | 0.0 |
| CLK021_D04 | 7968091 | 1 | A7 | 58.2 | 14.9 | 12.8 | 0.75 | 12.0 |
| CLK021_D08 | 7998911 | 1 | B7 | 97.1 | 8.4 | 10.5 | 0.97 | 0.4 |
| CLK025_B07 | STK214627 | 1 | C7 | 76.6 | 12.8 | 16.1 | 0.59 | 16.9 |
| CLK025_D07 | STK214630 | 1 | D7 | 77.0 | 19.1 | 16.6 | 0.62 | 19.4 |
| CLK025_F02 | STK281889 | 1 | E7 | 66.5 | 20.8 | 15.1 | 0.52 | 4.4 |
| CLK029_A05 | F0660-0389 | 1 | F7 | 8.5 | 4.7 | 10.8 | 0.98 | 0.0 |

*FIG. 5*

| | | | | | | | | |
|---|---|---|---|---|---|---|---|---|
| CLK029_A06 | F0660-1369 | 1 | G7 | 99.4 | 17.5 | 31.2 | 1.00 | 0.0 |
| CLK029_B05 | F0660-0585 | 1 | H7 | 97.1 | 21.9 | 16.1 | 1.00 | 0.0 |
| CLK029_B06 | F0660-1565 | 1 | A8 | 91.1 | 15.7 | 13.7 | 0.90 | 5.0 |
| CLK029_C06 | F0660-1761 | 1 | B8 | 20.7 | 5.2 | 7.9 | 0.98 | 14.2 |
| CLK029_D05 | F0660-0781 | 1 | C8 | 98.6 | 34.2 | 28.8 | 1.00 | 9.0 |
| CLK029_D06 | F0660-2153 | 1 | D8 | 7.4 | 6.3 | 7.8 | 0.98 | 1.1 |
| CLK029_E04 | F0620-1898 | 1 | E8 | 82.3 | 12.4 | 13.9 | 0.94 | 0.7 |
| CLK029_E05 | F0660-0879 | 1 | F8 | 87.8 | 13.9 | 15.5 | 0.96 | 0.1 |
| CLK029_E06 | F0660-2251 | 1 | G8 | 102.4 | 24.6 | 36.3 | 0.91 | 3.1 |
| CLK029_F03 | F0620-1882 | 1 | H8 | 10.2 | 4.8 | 6.6 | 0.98 | 0.0 |
| CLK029_F04 | F0653-0770 | 1 | A9 | 80.3 | 20.1 | 10.7 | 0.98 | 6.7 |
| CLK029_F05 | F0660-1075 | 1 | B9 | 107.4 | 27.2 | 20.5 | 0.88 | 10.1 |
| CLK029_F06 | F0660-2447 | 1 | C9 | 104.5 | 44.6 | 40.6 | 0.92 | 17.6 |
| CLK029_G04 | F0660-0193 | 1 | D9 | 104.6 | 21.8 | 22.0 | 0.84 | 4.6 |
| CLK029_G11 | F1365-2352 | 1 | E9 | 104.6 | 40.1 | 42.1 | 1.00 | 0.0 |
| CLK029_H04 | F0660-0291 | 1 | F9 | 104.8 | 61.5 | 51.6 | 0.67 | 21.2 |
| CLK029_H05 | F0660-1271 | 1 | G9 | 102.0 | 47.8 | 31.5 | 0.85 | 2.2 |
| CLK030_D07 | F1365-2819 | 1 | H9 | 103.8 | 41.1 | 30.7 | 1.00 | 0.1 |
| CLK030_F05 | F1365-2616 | 1 | A10 | 77.9 | 11.5 | 12.3 | 0.87 | 0.1 |
| CLK031_E03 | F1365-2951 | 1 | B10 | 102.3 | 44.7 | 20.2 | 1.00 | 2.5 |
| CLK031_F07 | F1365-2993 | 1 | C10 | 93.6 | 24.2 | 15.5 | 1.00 | 0.0 |
| CLK034_F10 | F1816-0952 | 1 | D10 | 80.5 | 13.6 | 12.3 | 0.99 | 1.3 |
| CLK035_D06 | F1816-1220 | 1 | E10 | 104.1 | 16.1 | 25.4 | 0.93 | 0.0 |
| CLK035_G03 | F1816-1053 | 1 | F10 | 89.6 | 20.0 | 14.8 | 0.64 | 0.6 |
| CLK037A03 | T5303593 | 1 | G10 | 44.1 | 31.3 | 66.7 | 0.77 | 107.9 |
| CLK037B02 | T5245539 | 1 | H10 | 36.5 | 30.6 | 48.9 | 0.78 | 11.3 |
| CLK037B04 | T5338958 | 1 | A11 | 15.1 | 9.6 | 13.4 | 0.91 | 60.9 |
| CLK037B06 | T5684501 | 1 | B11 | 45.4 | 73.3 | 93.7 | 0.74 | 43.2 |
| CLK037C02 | T5251597 | 1 | C11 | 54.3 | 34.7 | 44.6 | 0.68 | 56.6 |
| CLK037D05 | T5346274 | 1 | D11 | 82.5 | 26.5 | 60.6 | 0.83 | 104.7 |
| CLK037D06 | T5361568 | 1 | E11 | 61.8 | 37.4 | 61.0 | 0.80 | 92.1 |
| CLK037F03 | T5318013 | 1 | F11 | 59.8 | 24.2 | 62.6 | 0.77 | 52.0 |
| CLK037F10 | T5501753 | 1 | G11 | 95.1 | 39.1 | 23.1 | 0.78 | 45.7 |
| CLK037G04 | T5340795 | 1 | H11 | 79.9 | 20.1 | 88.8 | 0.60 | 2.1 |
| CLK037G05 | T5348233 | 2 | A2 | 67.4 | 32.9 | 82.9 | 1.00 | 13.7 |
| CLK037G10 | T5504536 | 2 | B2 | 82.7 | 53.8 | 69.2 | 0.62 | 3.3 |
| CLK037H02 | T5302162 | 2 | C2 | 50.0 | 20.5 | 57.2 | 0.58 | 62.1 |
| CLK038A02 | T5481330 | 2 | D2 | 77.4 | 80.4 | 88.7 | 0.77 | 88.8 |
| CLK038B08 | T5634471 | 2 | E2 | 66.7 | 81.3 | 92.6 | 0.65 | 72.7 |
| CLK039A06 | T5674813 | 2 | F2 | 76.4 | 50.2 | 79.4 | 0.77 | 72.4 |
| CLK039A10 | T5681518 | 2 | G2 | 64.7 | 73.5 | 75.9 | 0.64 | 70.1 |
| CLK039C07 | T5677217 | 2 | H2 | 78.1 | 69.7 | 92.6 | 0.71 | 33.6 |
| CLK039E04 | T5673745 | 2 | A3 | 99.3 | 97.2 | 100.3 | 1.00 | 75.9 |
| CLK039E05 | T5674360 | 2 | B3 | 87.4 | 86.2 | 87.2 | 0.75 | 103.4 |
| CLK039G04 | T5673752 | 2 | C3 | 37.5 | 15.8 | 29.0 | 0.85 | 31.4 |
| CLK039G05 | T5674787 | 2 | D3 | 65.5 | 76.2 | 88.1 | 0.88 | 73.8 |
| CLK039H06 | T5677213 | 2 | E3 | 36.8 | 33.4 | 34.6 | 0.80 | 0.5 |

*FIG. 5 (Cont'd)*

| | | | | | | | | |
|---|---|---|---|---|---|---|---|---|
| CLK040A04 | T5699614 | 2 | F3 | 74.1 | 55.0 | 49.4 | 0.74 | 64.0 |
| CLK040B04 | T5700007 | 2 | G3 | 68.1 | 60.6 | 77.9 | 0.73 | 59.8 |
| CLK040D03 | T5696063 | 2 | H3 | 77.0 | 64.0 | 84.8 | 0.92 | 53.7 |
| CLK041A09 | T5814547 | 2 | A4 | 69.5 | 17.9 | 20.4 | 1.00 | 0.6 |
| CLK041A10 | T5816145 | 2 | B4 | 73.4 | 11.8 | 19.0 | 0.75 | 0.0 |
| CLK041B10 | T5816888 | 2 | C4 | 95.5 | 43.5 | 53.8 | 0.75 | 4.6 |
| CLK041D03 | T5760990 | 2 | D4 | 49.9 | 13.1 | 15.8 | 0.43 | 11.7 |
| CLK041F08 | T5815669 | 2 | E4 | 86.0 | 22.1 | 22.3 | 0.71 | 6.9 |
| CLK041G08 | T5814795 | 2 | F4 | 97.2 | 30.7 | 51.5 | 0.97 | 1.4 |
| CLK041G09 | T5815734 | 2 | G4 | 90.8 | 22.3 | 35.0 | 0.85 | 0.2 |
| CLK041H08 | T5814797 | 2 | H4 | 68.1 | 14.1 | 16.7 | 0.95 | 0.0 |
| CLK042A03 | T5837887 | 2 | A5 | 22.7 | 12.3 | 14.4 | 0.64 | 16.2 |
| CLK042D11 | T5906009 | 2 | B5 | 77.8 | 23.2 | 48.7 | 0.85 | 2.4 |
| CLK043F03 | T5840791 | 2 | C5 | 11.4 | 9.8 | 10.4 | 1.00 | 0.0 |
| CLK042F04 | T5845211 | 2 | D5 | 61.3 | 35.5 | 35.0 | 0.85 | 4.8 |
| CLK042G04 | T5845235 | 2 | E5 | 34.8 | 23.9 | 27.6 | 0.88 | 4.1 |
| CLK043F07 | T5973408 | 2 | F5 | 59.4 | 15.8 | 36.3 | 0.80 | 33.3 |
| CLK044A03 | T6017115 | 2 | G5 | 69.9 | 37.6 | 41.2 | 0.68 | 8.7 |
| CLK044E07 | T6051328 | 2 | H5 | 67.8 | 48.5 | 77.2 | 0.95 | 41.6 |
| CLK044F08 | T6052793 | 2 | A6 | 86.9 | 76.0 | 76.3 | 0.85 | 87.6 |
| CLK044G05 | T6043228 | 2 | B6 | 78.2 | 89.0 | 93.5 | 0.80 | 25.4 |
| CLK044H02 | T6015972 | 2 | C6 | 99.3 | 33.9 | 62.0 | 0.75 | 3.7 |
| CLK044H06 | T6049165 | 2 | D6 | 57.6 | 60.7 | 61.9 | 0.78 | 94.6 |
| CLK045D04 | T6074787 | 2 | E6 | 35.7 | 28.8 | 34.9 | 0.57 | 63.8 |
| CLK045G04 | T6079930 | 2 | F6 | 83.1 | 87.2 | 91.4 | 0.81 | 88.9 |
| CLK046C11 | T6134740 | 2 | G6 | 78.8 | 75.4 | 81.9 | 1.00 | 74.4 |
| CLK046D07 | T6126336 | 2 | H6 | 81.1 | 65.1 | 65.2 | 1.00 | 0.0 |
| CLK046F09 | T6131938 | 2 | A7 | 64.4 | 71.8 | 68.7 | 0.72 | 67.4 |
| CLK046G11 | T6247294 | 2 | B7 | 90.8 | 85.1 | 82.3 | 0.91 | 72.5 |
| CLK046H08 | T6133232 | 2 | C7 | 58.1 | 68.8 | 63.5 | 0.72 | 46.8 |
| CLK046H11 | T6136299 | 2 | D7 | 81.3 | 75.7 | 83.0 | 0.73 | 94.2 |
| CLK047A02 | T6136477 | 2 | E7 | 82.2 | 71.3 | 84.7 | 0.89 | 94.2 |
| CLK047A04 | T6138073 | 2 | F7 | 46.3 | 31.1 | 47.1 | 0.44 | 42.8 |
| CLK047B02 | T6136478 | 2 | G7 | 76.2 | 73.1 | 75.1 | 0.63 | 103.8 |
| CLK047B06 | T6143738 | 2 | H7 | 72.6 | 14.7 | 59.3 | 0.81 | 0.0 |
| CLK047C02 | T6136575 | 2 | A8 | 30.2 | 27.8 | 46.7 | 0.91 | 40.5 |
| CLK047C03 | T6137000 | 2 | B8 | 52.4 | 68.4 | 73.5 | 0.58 | 61.3 |
| CLK047C05 | T6142267 | 2 | C8 | 67.0 | 82.7 | 73.5 | 0.64 | 92.6 |
| CLK047C07 | T6144812 | 2 | D8 | 74.5 | 71.3 | 75.6 | 0.58 | 90.3 |
| CLK047C09 | T6146879 | 2 | E8 | 50.4 | 46.3 | 51.9 | 0.62 | 89.7 |
| CLK047D03 | T6137031 | 2 | F8 | 71.2 | 28.6 | 64.1 | 0.86 | 87.1 |
| CLK047E02 | T6136814 | 2 | G8 | 48.8 | 57.2 | 64.5 | 0.48 | 40.6 |
| CLK047E03 | T6137033 | 2 | H8 | 55.1 | 43.6 | 58.8 | 0.97 | 31.3 |
| CLK047E06 | T6143956 | 2 | A9 | 66.1 | 64.3 | 76.1 | 0.68 | 81.2 |
| CLK047E07 | T6145541 | 2 | B9 | 73.1 | 21.8 | 65.9 | 0.75 | 18.0 |
| CLK047E08 | T6146370 | 2 | C9 | 65.6 | 76.5 | 81.3 | 0.87 | 71.8 |
| CLK047E10 | T6150835 | 2 | D9 | 57.9 | 35.2 | 51.9 | 0.67 | 57.6 |

*FIG. 5 (Cont'd)*

| | | | | | | | | |
|---|---|---|---|---|---|---|---|---|
| CLX047F02 | T6136843 | 2 | E9 | 42.6 | 19.9 | 40.9 | 0.87 | 22.9 |
| CLX047F03 | T6137053 | 2 | F9 | 61.2 | 66.0 | 62.1 | 0.74 | 71.1 |
| CLX047G02 | T6136845 | 2 | G9 | 71.9 | 79.3 | 79.4 | 0.85 | 97.4 |
| CLX047G03 | T6137576 | 2 | H9 | 61.8 | 61.2 | 69.0 | 0.96 | 56.3 |
| CLX047G11 | T6149865 | 2 | A10 | 84.4 | 84.8 | 71.2 | 0.91 | 44.5 |
| CLX047H02 | T6136949 | 2 | B10 | 43.6 | 36.2 | 35.7 | 0.93 | 51.5 |
| CLX047H03 | T6137982 | 2 | C10 | 62.5 | 37.4 | 47.8 | 0.58 | 44.5 |
| CLX048A02 | T6149989 | 2 | D10 | 76.3 | 70.9 | 75.6 | 0.43 | 98.9 |
| CLX048A03 | T6153234 | 2 | E10 | 34.5 | 32.0 | 33.1 | 0.75 | 73.9 |
| CLX048A04 | T6154797 | 2 | F10 | 41.8 | 38.7 | 44.1 | 0.54 | 44.0 |
| CLX048A06 | T6160253 | 2 | G10 | 53.0 | 51.0 | 69.1 | 0.54 | 78.8 |
| CLX048A07 | T6159205 | 2 | H10 | 41.7 | 48.4 | 51.9 | 0.87 | 37.6 |
| CLX048A11 | T6167001 | 2 | A11 | 49.4 | 34.6 | 41.9 | 0.65 | 21.3 |
| CLX048B02 | T6151274 | 2 | B11 | 50.3 | 17.2 | 41.3 | 0.55 | 0.8 |
| CLX048B04 | T6156885 | 2 | C11 | 54.1 | 58.6 | 79.4 | 0.76 | 59.1 |
| CLX048B07 | T6159394 | 2 | D11 | 35.5 | 16.1 | 19.4 | 0.58 | 2.7 |
| CLX048B09 | T6163535 | 2 | E11 | 45.3 | 21.1 | 38.1 | 0.77 | 10.1 |
| CLX048C06 | T6160827 | 2 | F11 | 47.7 | 40.7 | 64.8 | 0.78 | 24.2 |
| CLX048C09 | T6163537 | 2 | G11 | 79.5 | 61.7 | 81.3 | 0.99 | 103.3 |
| CLX048C10 | T6165055 | 2 | H11 | 56.1 | 79.3 | 71.4 | 0.86 | 32.4 |
| CLX048C11 | T6167053 | 3 | A2 | 47.6 | 62.2 | 47.0 | 0.93 | 3.8 |
| CLX048D03 | T6154156 | 3 | B2 | 66.0 | 96.4 | 96.9 | 0.78 | 81.9 |
| CLX048D07 | T6159604 | 3 | C2 | 70.4 | 72.0 | 88.0 | 0.97 | 91.4 |
| CLX048D11 | T6167319 | 3 | D2 | 78.1 | 91.4 | 98.2 | 0.94 | 111.0 |
| CLX048E03 | T6154158 | 3 | E2 | 74.3 | 50.7 | 87.4 | 1.00 | 124.2 |
| CLX048E08 | T6163215 | 3 | F2 | 39.7 | 11.0 | 11.4 | 0.75 | 0.0 |
| CLX048E09 | T6163697 | 3 | G2 | 77.6 | 106.7 | 112.8 | 0.82 | 109.9 |
| CLX048F02 | T6152994 | 3 | H2 | 54.9 | 25.8 | 35.1 | 0.98 | 0.8 |
| CLX048F03 | T6154173 | 3 | A3 | 79.1 | 85.0 | 95.5 | 0.77 | 63.6 |
| CLX048F10 | T6165769 | 3 | B3 | 55.8 | 78.7 | 79.4 | 0.71 | 72.9 |
| CLX048G03 | T6154330 | 3 | C3 | 40.3 | 32.8 | 33.9 | 0.75 | 91.8 |
| CLX048G08 | T6163238 | 3 | D3 | 62.8 | 34.0 | 67.7 | 0.90 | 5.2 |
| CLX048H09 | T6164999 | 3 | E3 | 65.5 | 84.5 | 81.0 | 0.65 | 124.1 |
| CLX049A03 | T6164239 | 3 | F3 | 84.4 | 93.3 | 93.4 | 0.61 | 125.7 |
| CLX049A09 | T6179175 | 3 | G3 | 49.8 | 93.3 | 78.6 | 0.82 | 47.2 |
| CLX049B02 | T6164307 | 3 | H3 | 73.1 | 83.2 | 81.0 | 0.66 | 49.3 |
| CLX049C02 | T6164332 | 3 | A4 | 47.2 | 114.9 | 93.2 | 0.81 | 109.1 |
| CLX049C07 | T6180437 | 3 | B4 | 78.2 | 84.0 | 99.1 | 0.97 | 128.6 |
| CLX049E10 | T6183277 | 3 | C4 | 87.2 | 118.5 | 112.2 | 0.94 | 108.6 |
| CLX049E02 | T6164560 | 3 | D4 | 38.6 | 68.3 | 55.6 | 0.72 | 93.2 |
| CLX049E09 | T6181646 | 3 | E4 | 39.4 | 14.2 | 8.8 | 0.81 | 4.8 |
| CLX049E10 | T6183277 | 3 | F4 | 60.9 | 56.1 | 78.3 | 0.90 | 134.8 |
| CLX049F06 | T6180238 | 3 | G4 | 74.2 | 63.6 | 69.3 | 0.66 | 14.6 |
| CLX049F10 | T6183308 | 3 | H4 | 61.9 | 41.5 | 51.3 | 0.99 | 0.0 |
| CLX050A03 | T6185930 | 3 | A5 | 38.1 | 19.9 | 18.1 | 0.69 | 9.2 |
| CLX050A04 | T6189082 | 3 | B5 | 39.3 | 39.1 | 48.2 | 0.73 | 75.0 |
| CLX050A06 | T6195297 | 3 | C5 | 60.7 | 57.4 | 79.6 | 0.59 | 83.4 |

*FIG. 5 (Cont'd)*

| | | | | | | | | |
|---|---|---|---|---|---|---|---|---|
| CLK050B08 | T6197802 | 3 | D5 | 44.8 | 107.5 | 76.6 | 0.57 | 44.1 |
| CLK050B10 | T6202871 | 3 | E5 | 48.5 | 73.7 | 79.9 | 0.78 | 84.6 |
| CLK050C05 | T6194308 | 3 | F5 | 89.1 | 87.8 | 82.7 | 0.92 | 111.6 |
| CLK050C08 | T6223558 | 3 | G5 | 79.2 | 91.9 | 74.9 | 0.76 | 118.3 |
| CLK050C10 | T6203513 | 3 | H5 | 65.3 | 85.9 | 65.4 | 0.96 | 46.7 |
| CLK050D11 | T6201525 | 3 | A6 | 81.8 | 120.7 | 114.3 | 0.80 | 75.1 |
| CLK050E09 | T6199844 | 3 | B6 | 66.4 | 93.3 | 91.0 | 0.68 | 91.8 |
| CLK050G05 | T6195260 | 3 | C6 | 81.8 | 80.0 | 94.2 | 0.79 | 123.7 |
| CLK050G09 | T6199896 | 3 | D6 | 59.7 | 118.5 | 94.6 | 0.70 | 66.6 |
| CLK050H09 | T6199914 | 3 | E6 | 45.6 | 84.1 | 61.4 | 0.78 | 27.3 |
| CLK051H02 | T6213481 | 3 | F6 | 57.8 | 49.4 | 68.1 | 0.71 | 80.0 |
| CLK052A03 | T6248551 | 3 | G6 | 54.2 | 84.1 | 57.6 | 0.59 | 42.5 |
| CLK052G05 | T5444987 | 3 | H6 | 91.3 | 16.3 | 10.5 | 0.79 | 1.9 |
| CLK008_C02 | BAS 11787974 | 3 | A7 | 52.1 | 22.1 | 30.3 | 0.76 | 2.0 |
| CLK008_C05 | ASN 12291324 | 3 | B7 | 35.9 | 94.2 | 59.9 | 0.56 | 11.3 |
| CLK008_D02 | ASN 12292402 | 3 | C7 | 38.5 | 13.2 | 11.5 | 0.72 | 0.4 |
| CLK008_E05 | ASN 12291912 | 3 | D7 | 17.2 | 11.6 | 6.8 | 0.99 | 0.7 |

FIG. 5 (Cont'd)

| Ligand | R | RT-min | m/z |
|---|---|---|---|
| ASV1E9T | quinolin-2-yl | 13.457 | 594.3080 |
| ASV1C8T | naphthalen-2-yl | 13.450 | 592.3123 |
| ASV1D11T | 5-Br-furan-2-yl | 12.747 | 612.1755 |
| ASV1A7T | 5-Br-thiophen-3-yl | 13.280 | 628.1469 |
| ASV1C7T | 6-Br-pyridin-2-yl | 13.163 | 623.1932 |
| ASV1F3T | 2,2-difluoro-benzo[1,3]dioxol-4-yl | 13.483 | 622.2701 |
| ASV1C9T | 5-Cl-thiophen-2-yl | 13.333 | 582.2079 |
| ASV2B5T | 3-Cl-thiophen-2-yl | 13.037 | 582.2103 |
| ASV1C10T | 2-Br-thiazol-5-yl | 12.737 | 629.1422 |
| ASV2A10T | 5-methyl-furan-2-yl | 12.020 | 547.2851 |
| 48E9T | quinoxalin-2-yl | 12.857 | 594.2980 |
| 49A2T | 5-Br-furan-3-yl | 12.937 | 612.1663 |
| 49C10T | 6-methyl-pyridin-2-yl | 12.677 | 558.2985 |

| Ligand | PYR1 | PYL4 | PYL8 |
|---|---|---|---|
| ASV1E9T | 121±26 | 67±29 | 92±34 |
| ASV1C8T | 747±196 | 1475±301 | 213±63 |
| ASV1D11T | 414±80 | 296±90 | 173±53 |
| ASV1A7T | 144±45 | 319±58 | 161±87 |
| 49A2T | 116±39 | 149±50 | 180±62 |
| ASV1C7T | 235±96 | 646±245 | 357±149 |
| ASV1F3T | 269±41 | 1083±388 | 539±219 |
| 48E9T | 156±14 | 97±17 | 149±36 |
| 49C10T | 387±69 | 762±183 | 320±83 |
| ASV1C9T | 162±25 | 281±53 | 171±42 |
| ASV2B5T | 627±132 | 3157±966 | 2003±496 |
| 1H6T | 375±73 | 860±272 | 1007±289 |
| 6E4T | 195±42 | 20025±3358 | 7424±3420 |
| ASV1C10T | 226±73 | 107±37 | 215±102 |
| ASV2A10T | 363±94 | 827±307 | 161±87 |
| OPZ | 8073±1985 | 64736±14409 | 6679±3840 |
| AA1 | n.s | n.s | n.s |
| PanMe | 26307±7716 | 6236±1740 | 5869±1070 |

*FIG. 10*

| Ligand | Greening EC₅₀(nM) | % Germination at 200 nM |
|---|---|---|
| Mock | | 100 |
| ABA | | 1.2 |
| ASV1E9T | 1386 | 81 |
| ASV1C8T | 2258 | 21 |
| ASV1D11T | 2273 | 16 |
| ASV1A7T | 3174 | 16 |
| 4BA2T | 3361 | 18 |
| ASV1C7T | 4305 | 0 |
| ASV1F3T | 4462 | 55 |
| 4BE3T | 5709 | 22 |
| 4OC10T | 8875 | 6.5 |
| ASV1C9T | 13133 | 24 |
| ASV2B5T | 18068 | 0 |
| 1H8T | >60000 | 3 |
| 9E4T | >60000 | 0.8 |
| ASV1C10T | >60000 | 1.7 |
| ASV2A10T | >60000 | 10 |
| OPZ | >60000 | 0 |
| Pyrabactin | Toxic-N.D | 43 |
| AA1 | >60000 | 0 |

| Ligand | % Normalized root growth | | | | | |
|---|---|---|---|---|---|---|
| | 5 µM | P value to mock | P value to ABA | 10 µM | P value to mock | P value to ABA |
| Mock | 100 | 1 | | 100 | 1 | |
| ABA | 31 | <0.0001 | 1 | 31 | <0.0001 | 1 |
| ASV1E3T | 96 | 0.9998 | <0.0001 | 105 | 0.9998 | <0.0001 |
| ASV1C8T | 83 | 0.0708 | <0.0001 | 93 | 0.9921 | <0.0001 |
| ASV1D11T | 79 | 0.0072 | <0.0001 | 88 | 0.5581 | <0.0001 |
| ASV1A7T | 82 | 0.0370 | <0.0001 | 90 | 0.6923 | <0.0001 |
| 49A2T | 78 | 0.0058 | <0.0001 | 83 | 0.0765 | <0.0001 |
| ASV1C7T | 56 | <0.0001 | 0.0007 | 73 | 0.0001 | <0.0001 |
| ASV1F3T | 45 | <0.0001 | 0.2095 | 58 | <0.0001 | 0.0001 |
| 48E9T | 90 | 0.7536 | <0.0001 | 80 | 0.0139 | <0.0001 |
| 49C10T | 53 | <0.0001 | 0.0030 | 63 | <0.0001 | <0.0001 |
| ASV1C9T | 72 | <0.0001 | <0.0001 | 87 | 0.3101 | <0.0001 |
| ASV2B5T | 46 | <0.0001 | 0.1456 | 61 | <0.0001 | <0.0001 |
| 1H6T | 44 | <0.0001 | 0.3550 | 48 | <0.0001 | 0.0765 |
| 6E4T | 34 | <0.0001 | 0.9993 | 35 | <0.0001 | 0.9998 |
| ASV1C10T | 68 | <0.0001 | <0.0001 | 95 | 0.9990 | <0.0001 |
| ASV2A10T | 54 | <0.0001 | 0.0029 | 79 | 0.0063 | <0.0001 |
| OPZ | 63 | <0.0001 | <0.0001 | 72 | <0.0001 | <0.0001 |
| AA1 | 46 | <0.0001 | 0.0964 | 40 | <0.0001 | 0.8647 |
| PanMe | 75 | 0.0004 | <0.0001 | 58 | <0.0001 | <0.0001 |

*FIG. 13*

| Ligand | PYR1 | PYL4 | PYL8 | Greening EC50(nM) | % Germination at 200 nM |
|---|---|---|---|---|---|
| Mock | | | | | 100 |
| ABA | | | | | 1-2 |
| ASV1E9 | 121±26 | 67±29 | 92±34 | 1366 | 81 |
| ASV1C8 | 747±196 | 1475±301 | 213±63 | 2258 | 21 |
| ASV1D11 | 414±80 | 296±90 | 173±53 | 2279 | 16 |
| ASV1A7 | 144±45 | 319±58 | 161±87 | 3174 | 16 |
| 49A2 | 116±39 | 149±50 | 180±62 | 3361 | 16 |
| ASV1C7 | 235±96 | 646±245 | 357±149 | 4305 | 0 |
| ASV1F3 | 269±41 | 1083±388 | 539±219 | 4462 | 5.5 |
| 48E9 | 156±14 | 97±17 | 149±36 | 5709 | 22 |
| 49C10 | 387±69 | 762±183 | 320±83 | 8875 | 6.5 |
| ASV1C9 | 162±25 | 281±53 | 171±42 | 13133 | 24 |
| ASV2B5 | 627±132 | 3157±966 | 2003±496 | 18068 | 0 |
| 1H6 | 375±73 | 860±272 | 1007±289 | >50000 | 3 |
| 6E4 | 195±42 | 20025±3358 | 7424±3420 | >50000 | 0.8 |
| ASV1C10 | 226±73 | 107±37 | 215±102 | >50000 | 1.7 |
| ASV2A10 | 363±94 | 827±307 | 161±87 | >50000 | 10 |
| OPZ | 8073±1985 | 64736±1440 | 6679±3840 | >50000 | 0 |
| AA1 | n.s | n.s | n.s | ≈50000 | 0 |
| PanMe | 26307±7716 | 6236±1740 | 5869±1070 | Toxic-N.D | 43 |

*FIG. 19*

UNUSUALLY POTENT ABA RECEPTOR PAN-ANTAGONISTS

CROSS-REFERENCE TO RELATED APPLICATIONS

The present patent application claims the benefit of U.S. Provisional Patent Application No. 62/864,392, filed Jun. 20, 2019, the contents of which are incorporated by reference herein for all purposes.

STATEMENT AS TO RIGHTS TO INVENTIONS MADE UNDER FEDERALLY SPONSORED RESEARCH AND DEVELOPMENT

This invention was made with government support under Grant No. 1656890, which was awarded by the National Science Foundation. The government has certain rights in this invention.

FIELD OF THE INVENTION

The present invention sets forth new compounds that potently block activation of ABA receptors. In some aspects, these compounds can be used to enhance germination of crop seeds to stand establishment and to increase transpiration and photosynthetic yields when water is not limiting plant growth.

BACKGROUND OF THE INVENTION

ABA receptors are cellular targets in plants that can be activated to enhance stress tolerance or inhibited to increase growth and germination. Currently developed inhibitors have numerous limitations including phototoxicity at high concentrations, complicated synthetic routes, incomplete antagonism of important receptor target sites, and low potency in vitro and in vivo.

Abscisic acid (ABA) is key phytohormone that controls a wide array of physiological processes in plants such as seed development, germination and dormancy and responses to biotic and abiotic stresses (1). ABA acts via the PYR/PYL/RCAR (pyrabactin resistance 1/pyrabactin resistance like/regulatory component of ABA receptor) soluble receptor proteins (2, 3). Upon binding, ABA triggers a conformational change in a mobile gate loop flanking the ligand binding pocket such that the ABA-receptor complex can then bind to and inhibit Glade A family of type II C protein phosphatases (PP2Cs), which dephosphorylate and inactivate SNF1-related protein kinase 2 (SnRK2). SnRK2s are activated in the presence of ABA, and phosphorylate downstream targets leading to numerous cellular outputs (4, 5). Novel scaffolds that can agonize and antagonize these receptors may help dissect the roles of ABA in various physiological processes and be useful for manipulating abiotic stress responses, transpiration, and plant growth. For example, ABA receptor agonists induce guard cell closure and reduce transpiration and water use, which is beneficial when water levels are limiting growth, while antagonists can be used to stimulate stomatal opening and increase gas exchange, which may be beneficial when water is not limiting growth. Antagonists can be valuable reagents for stimulating germination, particularly during adverse conditions which often reduce germination in an ABA-mediated process called thermoinhibition. Antagonists will also block ABA's inhibitory effects on plant growth and can be used to stimulate growth when environmental abiotic stressors are minimal, for example in controlled growth environments. Thus both ABA receptor agonists and antagonists could have broad agricultural applications.

While there are several ABA agonists (2, 6-22), only a few antagonists of ABA receptors have been reported. Most ABA receptor antagonists are ABA analogs such as AS6 (23), PAO4 (24), and PanMe (25), or are inspired from natural products such as RK460 (26), and have multi-step and costly synthetic routes which may eventually increase production costs. Furthermore, they have intrinsic limitations including modest in vitro activity (AS6, PAO4, PanMe), unfavorable ABA receptor selectivity profile (RK460) or, as we show here, phytotoxicity (PanMe). Recently, a small molecule pan-antagonist (AA1) was identified from a forward chemical genetic screen for inhibitors of ABA-induced germination arrest (2); we show here that AA1 is not an ABA receptor pan-antagonist and has very limited bioactivity in vivo and negligible activity in vitro.

In principle, there are at least two simple mechanism for blocking ABA receptor activation: preventing gate closure or disrupting activity of the activated closed gate conformer. X-ray crystallographic studies show that AS6 and PanMe both enable gate closure but both ligands possess substituents that create steric clashes and frustrate the ability of activated receptors to bind PP2Cs and activate downstream signaling. AS6 is an ABA derivative modified at its 3'-carbon with a hexylthioether linker that extends through a solvent accessible pore called the 3'-tunnel; this extension prevents association of the closed, activated receptor with PP2Cs. PanMe similarly blocks PP2C interactions, but its 4'-toluyl-propynylether can adopt two conformations, one that resides in the 4'-tunnel and blocks interactions of activated receptors with the Trp-lock residue on the PP2C, and another conformer that occupies the 3'-tunnel. Antagonists that prevent gate closure have not yet been described but should, in principle, be possible of forming stable interactions between an antagonist and the open gate conformer. In this invention, we describe new highly potent OP derivatives developed using click chemistry that antagonize ABA receptors. Structure activity relationships of the new antagonists suggest that the gate is unlikely to adopt a canonical closed-conformer upon antagonist binding.

BRIEF SUMMARY OF THE INVENTION

We have synthesized potent ABA antagonists. These new antagonists have the highest reported activity in vitro and in vivo. The compounds can be used to manipulate physiological functions controlled by ABA such as germination and transpiration for agricultural benefit.

In some aspects, the invention presents a composition or compound as otherwise disclosed herein.

In some aspects, the invention presents an agricultural formulation comprising a compound as otherwise disclosed herein. In some aspects, the agricultural formulation further comprises a carrier.

In some aspects, the invention presents a method of increasing drought tolerance in a plant, the method comprising contacting a plant with a sufficient amount of the agricultural formulation as otherwise disclosed herein, thereby increasing drought tolerance in the plant compared to not contacting the plant with the formulation.

In some aspects, the invention presents a method of bringing a plant in contact with the agricultural formulation as otherwise disclosed herein, comprising contacting the plant with the agricultural formulation.

In some aspects, the invention presents a method of activating a PYR/PYL protein, the method comprising contacting the PYR/PYL protein with a compound of Formula I, II, or III as disclosed herein.

In some embodiments, the agricultural formulation further comprises an agricultural chemical that is useful for promoting plant growth, reducing weeds, or reducing pests. In some embodiments, the agricultural formulation further comprises at least one of a fungicide, an herbicide, a pesticide, a nematicide, an insecticide, a plant activator, a synergist, an herbicide safener, a plant growth regulator, an insect repellant, an acaricide, a molluscicide, or a fertilizer. In some embodiments, the agricultural formulation further comprises a surfactant. In some embodiments, the agricultural formulation further comprises a carrier.

In some aspects, the invention provides methods for increasing abiotic stress tolerance in a plant, the method comprising the step of contacting a plant with a sufficient amount of the above formulations to increase abiotic stress tolerance in the plant compared to the abiotic stress tolerance in the plant when not contacted with the formulation. In some embodiments, the plant is a monocot. In some embodiments, the plant is a dicot. In some embodiments, the abiotic stress tolerance comprises drought tolerance.

In some aspects, the invention provides a method of enhancing seed germination in a plant, the method comprising the step of contacting a plant, a plant part, or a plant seed with a sufficient amount of the above formulations to enhance germination.

In some aspects, the invention provides a plant or plant part in contact with the above formulations. In some embodiments, the plant or plant part is a seed.

In some aspects, the invention provides a method of inactivating a PYR/PYL protein. In some embodiments, the PYR/PYL protein binds a type 2 protein phosphatase (PP2C) polypeptide when the PYR/PYL protein binds the agonist compound quinabactin. In some embodiments, the method comprises the step of contacting the PYR/PYL protein with any of the compounds described herein.

Further aspects, objects, and advantages of the invention will become apparent upon consideration of the detailed description and figures that follow.

BRIEF DESCRIPTION OF THE DRAWINGS

FIG. 13. Normalized primary root lengths of seedlings treated with different antagonists at 5 and 10 µM, in presence of 10 µM ABA. Statistical comparisons done to mock and ABA treated seedlings done using one-way ANOVA using Dunnett's test, with n=36 for mock and ABA treated seedlings and n=6 for chemical treatments.

FIG. 19. Table showing antagonist potency against different *Arabidopsis* receptors, as measured using agonist/receptor-mediated inhibition of ΔN-HAB1 phosphatase activity (n=3); n.s indicates that PP2C activity was not significantly different at 50 μM test chemical in presence of 5 uM ABA (the highest concentration tested). All assays contained 50 Nm receptor and 25 nM ΔN-HAB1 except PYL4 where the receptor concentration was 100 nM. The potency of different antagonists on *Arabidopsis* greening assays and their corresponding-greening EC50 values (concentrations required to restore greening to 50% of mock treated in presence of 1 uM ABA). No greening was observed with 1 uM ABA and greening for chemical treatments was normalized to mock which was treated as 100%. % germination in *Arabidopsis* germination assays in presence of 1 uM ABA and 200 nM antagonist. Mock treated controls had 100% germination, while ABA controls had a germination of 1-2%.

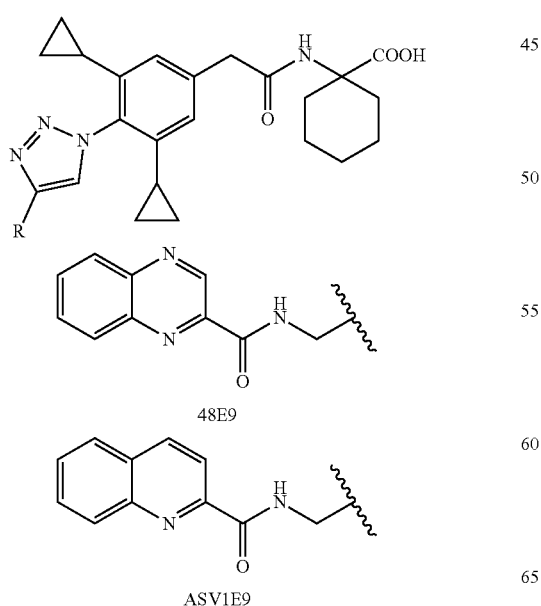

48E9

ASV1E9

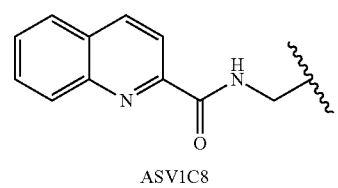

ASV1C8

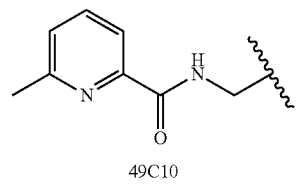

49C10

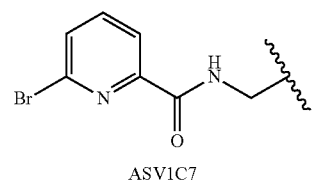

ASV1C7

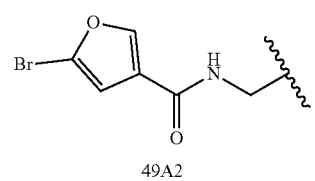

49A2

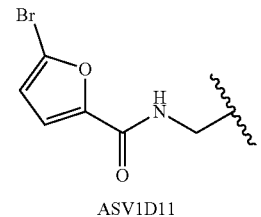

ASV1D11

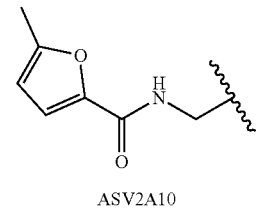

ASV2A10

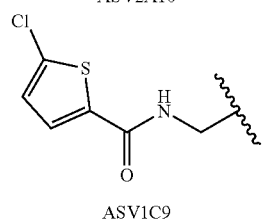

ASV1C9

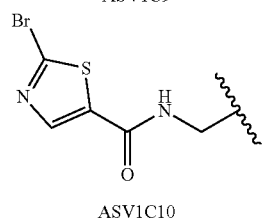

ASV1C10

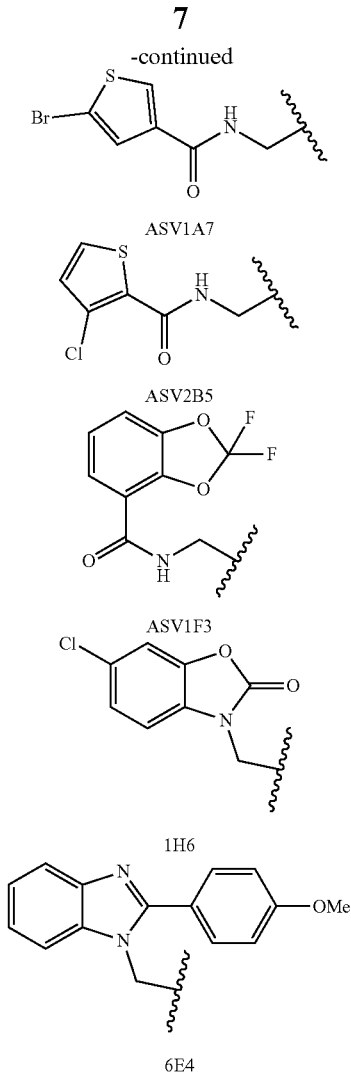

ASV1A7

ASV2B5

ASV1F3

1H6

6E4

DETAILED DESCRIPTION OF THE INVENTION

I. Definitions

Figure 1:
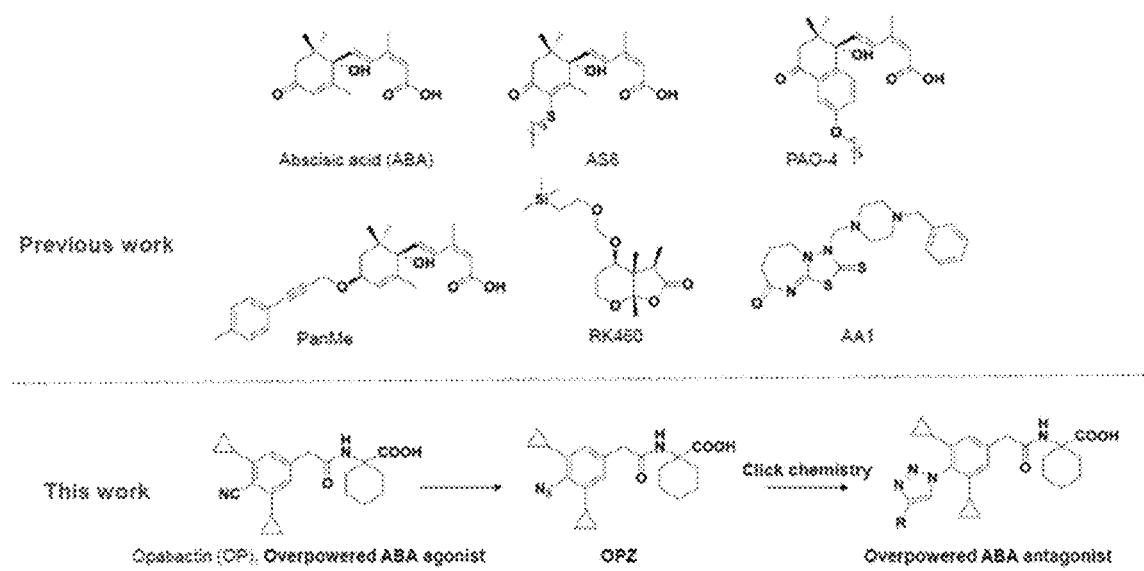
FIG. 1. Structures of existing ABA antagonists and click chemistry approach adopted in the present invention.

"Agonists" are agents that, e.g., induce or activate the expression of a described target protein or bind to, stimulate, increase, open, activate, facilitate, enhance activation, sensitize or up-regulate the activity of one or more plant PYR/PYL proteins (or encoding polynucleotide). Agonists can include naturally occurring and synthetic molecules. In some embodiments, the agonists are combined with agrichemicals to produce an agricultural formulation. Examples of suitable agrichemicals include fungicides, herbicides, pesticides, fertilizers, or surfactants. Assays for determining whether an agonist "agonizes" or "does not agonize" a PYR/PYL protein include, e.g., contacting putative agonists to purified PYR/PYL protein(s) and then determining the functional effects on the PYR/PYL protein activity, as described herein, or contacting putative agonists to cells expressing PYR/PYL protein(s) and then determining the functional effects on the described target protein activity, as described herein. One of skill in the art will be able to determine whether an assay is suitable for determining whether an agonist agonizes or does not agonize a PYR/PYL protein. Samples or assays comprising PYR/PYL proteins that are treated with a putative agonist are compared to control samples without the agonist to examine the extent of effect. Control samples (untreated with agonists) are assigned a relative activity value of 100%. Agonism of the PYR/PYL protein is achieved when the activity value relative to the control is 110%, optionally 150%, optionally 200%, 300%, 400%, 500%, 1000-3000%, or higher.

The term "PYR/PYL receptor polypeptide" refers to a protein characterized in part by the presence of one or more or all of a polyketide cyclase domain 2 (PF10604), a polyketide cyclase domain 1 (PF03364), and a Bet V I domain (PF03364), which in wild-type form mediates abscisic acid (ABA) and ABA analog signaling. A wide variety of PYR/PYL receptor polypeptide sequences are known in the art. In some embodiments, a PYR/PYL receptor polypeptide comprises a polypeptide that is substantially identical to any one of SEQ ID NOs:1-119. See, e.g., Int. Pat. Pub. No. WO 2011/139798 (U.S. Pat. App. Pub. No. US 2011/0271408).

The term "activity assay" refers to any assay that measures or detects the activity of a PYR/PYL receptor polypeptide. An exemplary assay to measure PYR/PYL receptor activity is a yeast two-hybrid assay that detects binding of a PYR/PYL polypeptide to a type 2 protein phosphatase (PP2C) polypeptide, as described in the Examples.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

The phrase "substantially identical," used in the context of two nucleic acids or polypeptides, refers to a sequence that has at least 60% sequence identity with a reference sequence. Alternatively, percent identity can be any integer from 60% to 100%. Some embodiments include at least: 60%, 65%, 70%, 75%, 80%, 85%, 90%, 91%, 92%, 93%, 94% 95%, 96%, 97%, 98%, or 99%, compared to a reference sequence using the programs described herein; preferably BLAST using standard parameters, as described below. Embodiments of the present invention provide for polypeptides, and nucleic acids encoding polypeptides, that are substantially identical to any of SEQ ID NO:1-119.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci.* USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=-2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci.* USA 89:10915 (1989)).

The BLAST algorithm also performs a statistical analysis of the similarity between two sequences (see, e.g., Karlin & Altschul, Proc. *Nat'l. Acad. Sci.* USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alter a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, Proteins (1984)).

The term "plant" includes whole plants, shoot vegetative organs or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the methods of the invention includes angiosperms (monocotyledonous and dicotyledonous plants), gymnosperms, ferns, bryophytes, and multicellular and unicellular algae. It includes plants of a variety of ploidy levels, including aneuploid, polyploid, diploid, haploid, and hemizygous.

As used herein, the term "drought-resistance" or "drought-tolerance," including any of their variations, refers to the ability of a plant to recover from periods of drought stress (i.e., little or no water for a period of days). Typically, the drought stress will be at least 5 days and can be as long as, for example, 18 to 20 days or more (e.g., at least 6, 7, 8, 9, 10, 11, 12, 13, 14, 15, 16, 17, 18, 19, 20 days), depending on, for example, the plant species.

As used herein, the terms "abiotic stress," "stress," or "stress condition" refer to the exposure of a plant, plant cell, or the like, to a non-living ("abiotic") physical or chemical agent that has an adverse effect on metabolism, growth, development, propagation, or survival of the plant (collectively, "growth"). A stress can be imposed on a plant due, for example, to an environmental factor such as water (e.g., flooding, drought, or dehydration), anaerobic conditions (e.g., a lower level of oxygen or high level of $CO_2$), abnormal osmotic conditions, salinity, or temperature (e.g., hot/heat, cold, freezing, or frost), a deficiency of nutrients or exposure to pollutants, or by a hormone, second messenger, or other molecule. Anaerobic stress, for example, is due to a reduction in oxygen levels (hypoxia or anoxia) sufficient to produce a stress response. A flooding stress can be due to prolonged or transient immersion of a plant, plant part, tissue, or isolated cell in a liquid medium such as occurs during monsoon, wet season, flash flooding, or excessive irrigation of plants, or the like. A cold stress or heat stress can occur due to a decrease or increase, respectively, in the temperature from the optimum range of growth temperatures for a particular plant species. Such optimum growth temperature ranges are readily determined or known to those skilled in the art. Dehydration stress can be induced by the loss of water, reduced turgor, or reduced water content of a cell, tissue, organ or whole plant. Drought stress can be induced by or associated with the deprivation of water or reduced supply of water to a cell, tissue, organ or organism. Salinity-induced stress (salt-stress) can be associated with or induced by a perturbation in the osmotic potential of the intracellular or extracellular environment of a cell. As used herein, the term "abiotic stress tolerance" or "stress tolerance" refers to a plant's increased resistance or tolerance to abiotic stress as compared to plants under normal conditions and the ability to perform in a relatively superior manner when under abiotic stress conditions.

A polypeptide sequence is "heterologous" to an organism or a second polypeptide sequence if it originates from a foreign species, or, if from the same species, is modified from its original form.

The terms "a," "an," or "the" as used herein not only include aspects with one member, but also (unless specified otherwise) include aspects with more than one member. For example, an embodiment of a method of imaging that comprises using a compound set forth in claim 1 would include an aspect in which the method comprises using two or more compounds set forth in claim 1.

"Alkenyl" as used herein includes a straight or branched aliphatic hydrocarbon group of 2 to about 15 carbon atoms that contains at least one carbon-carbon double bond. Preferred alkenyl groups have 2 to about 6 carbon atoms. More preferred alkenyl groups contain 2 to about 3 carbon atoms. "Lower alkenyl" as used herein includes alkenyl of 2 to about 6 carbon atoms. Representative alkenyl groups include vinyl, allyl, n-butenyl, 2-butenyl, 3-methylbutenyl, n-pentenyl, and the like.

"Alkoxy" as used herein includes an alkyl—O— group wherein the alkyl group is as defined herein. Representative alkoxy groups include methoxy, ethoxy, n-propoxy, i-propoxy, n-butoxy, heptoxy, and the like.

"Alkyl" as used herein includes an aliphatic hydrocarbon group, which may be straight or branched-chain, having about 1 to about 20 carbon atoms in the chain. Preferred alkyl groups have 1 to 8, 1 to 6, 1 to 4, or 1 to 3 carbon atoms in the chain. "Branched-chain" as used herein includes groups in which one or more lower alkyl groups such as methyl, ethyl or propyl are attached to a linear alkyl chain (e.g., 2-methyl-3-pentyl). "Lower alkyl" as used herein includes 1 to about 6 carbon atoms in the chain, which may be straight or branched (e.g., methyl, ethyl, n-propyl, isopropyl, n-butyl, 2-butyl, t-butyl, n-pentyl, 2-pentyl, 3-pentyl, 2-methyl-2-butyl, and the like). Representative alkyl groups include methyl, ethyl, n-propyl, isopropyl, n-butyl, t-butyl, n-pentyl, and 3-pentyl.

"Alkylthio" as used herein includes an alkyl—S— group wherein the alkyl group is as defined herein. Preferred alkylthio groups are those wherein the alkyl group is lower alkyl. Representative alkylthio groups include methylthio, ethylthio, isopropylthio, heptylthio, and the like.

"Alkynyl" as used herein includes a straight or branched aliphatic hydrocarbon group of 2 to about 15 carbon atoms that contains at least one carbon-carbon triple bond. Preferred alkynyl groups have 2 to about 12 carbon atoms. More preferred alkynyl groups contain 2 to about 6 carbon atoms. "Lower alkynyl" as used herein includes alkynyl of 2 to about 6 carbon atoms. Representative alkynyl groups include propynyl, 2-butynyl, 3-methylbutynyl, n-pentynyl, heptynyl, and the like.

"Amino" as used herein includes a group of formula $Y_1Y_2N$ wherein $Y_1$ and $Y_2$ are independently hydrogen, acyl, aryl, or alkyl; or $Y_1$ and $Y_2$, together with the nitrogen through which $Y_1$ and $Y_2$ are linked, join to form a 4- to 7-membered azaheterocyclyl group (e.g., piperidinyl). Optionally, when $Y_1$ and $Y_2$ are independently hydrogen or alkyl, an additional substituent can be added to the nitrogen, making a quaternary ammonium ion. Representative amino groups include primary amino ($H_2N$—), methylamino, dimethylamino, diethylamino, tritylamino, and the like. Preferably, "amino" is an —NRR' group where R and R' are members independently selected from the group consisting of H and alkyl. Preferably, at least one of R and R' is H.

"Comprises" as used herein is not closed—that is, it does not limit a composition to include only the expressly disclosed components. For example, "a composition comprising A and B" could be a composition containing only A and B; a composition containing A, B, and C; a composition containing A, B, C, and D; and the like.

"Cycloalkyl" as used herein includes a non-aromatic mono- or multicyclic ring system of about 3 to about 10 carbon atoms, preferably of about 3 to about 5 carbon atoms. More preferred cycloalkyl rings include cyclopropyl. A cycloalkyl group optionally comprises at least one $sp^2$-hybridized carbon (e.g., a ring incorporating an endocyclic or exocyclic olefin). Representative monocyclic cycloalkyl groups include cyclopentyl, cyclohexyl, cyclohexenyl, cycloheptyl, and the like. Representative multicyclic cycloalkyl include 1-decalin, norbornyl, adamantyl, and the like.

"Halo" or "halogen" as used herein includes fluoro, chloro, bromo, or iodo. A preferred halogen is fluoro.

"Haloalkyl" as used herein includes an alkyl group wherein the alkyl group includes one or more halo-substituents. For example, "fluoroalkyl" is an alkyl group wherein the alkyl group includes fluoro-substituents (e.g., trifluoromethyl).

When any two substituent groups or any two instances of the same substituent group are "independently selected" from a list of alternatives, they may be the same or different. For example, if $R^a$ and $R^b$ are independently selected from the group consisting of methyl, hydroxymethyl, ethyl, hydroxyethyl, and propyl, then a molecule with two $R^a$ groups and two $R^b$ groups could have all groups be methyl. Alternatively, the first $R^a$ could be methyl, the second $R^a$ could be ethyl, the first $R^b$ could be propyl, and the second $R^b$ could be hydroxymethyl (or any other substituents taken from the group). Alternatively, both $R^a$ and the first $R^b$ could be ethyl, while the second $R^b$ could be hydroxymethyl (i.e., some pairs of substituent groups may be the same, while other pairs may be different).

The prefixes "u" and "μ" are used herein interchangeably to denote "micro." For example, "uM" and "μM" are used interchangeably denote "micromolar."

Abscisic acid is a multifunctional phytohormone involved in a variety of phyto-protective functions including bud dormancy, seed dormancy or maturation, abscission of leaves and fruits, and response to a wide variety of biological stresses (e.g. cold, heat, salinity, and drought). ABA is also responsible for regulating stomatal closure by a mechanism independent of $CO_2$ concentration. The PYR/PYL family of ABA receptor proteins mediate ABA signaling. Plants examined to date express more than one PYR/PYL receptor protein family member, which have at least somewhat redundant activity. PYR/PYL receptor proteins mediate ABA signaling as a positive regulator in, for example, seed germination, post-germination growth, stomatal movement and plant tolerance to stress including, but not limited to, drought.

A wide variety of wild-type (naturally occurring) PYR/PYL polypeptide sequences are known in the art. Although PYR1 was originally identified as an abscisic acid (ABA) receptor in *Arabidopsis*, in fact PYR1 is a member of a group of at least 14 proteins (PYR/PYL proteins) in the same protein family in *Arabidopsis* that also mediate ABA signaling. This protein family is also present in other plants (see, e.g., SEQUENCE LISTING) and is characterized in part by the presence of one or more or all of a polyketide cyclase domain 2 (PF10604), a polyketide cyclase domain 1 (PF03364), and a Bet V I domain (PF03364). START/Bet v 1 superfamily domain are described in, for example, Radauer, BMC Evol. Biol. 8:286 (2008). In some embodiments of the methods described, a wild-type PYR/PYL receptor polypeptide comprises any of SEQ ID NOs:1-119. In some embodiments, a wild-type PYR/PYL receptor polypeptide is substantially identical to (e.g., at least 70%, 75%, 80%, 85%, 90%, 91%, 92%, 93%, 94% 95%, 96%, 97%, 98%, or 99% identical to) any of SEQ ID NOs:1-119. In some embodiments, a PYR/PYL receptor polypeptide is substantially identical to (e.g., at least 70%, 75%, 80%, 85%, 90%, 91%, 92%, 93%, 94% 95%, 96%, 97%, 98%, or 99% identical to) any of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, or 119.

As used herein, the term "transgenic" describes a non-naturally occurring plant that contains a genome modified by man, wherein the plant includes in its genome an exogenous nucleic acid molecule, which can be derived from the same or a different plant species. The exogenous nucleic acid molecule can be a gene regulatory element such as a promoter, enhancer, or other regulatory element, or can contain a coding sequence, which can be linked to a heterologous gene regulatory element. Transgenic plants that arise from sexual cross or by selfing are descendants of such a plant and are also considered "transgenic."

II. Aba Receptor Antagonists

The present invention sets forth small-molecule ABA receptor antagonists. In some aspects, the present invention provides for agricultural formulations and methods comprising the ABA receptor antagonists described herein.

In certain aspects and embodiments, the present invention sets forth a compound of Formula I:

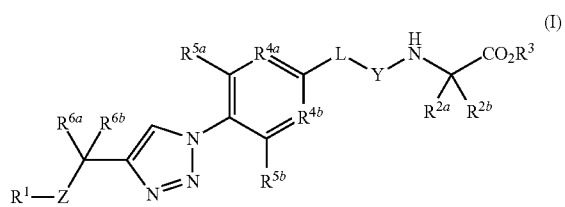

wherein
$R^1$ is a heterocycle, aryl, or heteroaryl group, optionally substituted with from 1 to 4 $R^9$ groups;
L is selected from the group consisting of a single bond, —$(O)_m$—$CH_2$—, and —$(O)_m$—$CH(R^{10})$—;
m is an integer selected from the group consisting of 0 and 1;
Y is —C(O)— or —S(O)$_2$—;
Z is a single bond or —C(O)—$NR^7$—
$R^{2a}$ and $R^{2b}$ are each independently selected from the group consisting of hydrogen and $R^{10}$, wherein at most one of $R^{2a}$ or $R^{2b}$ is hydrogen; or, alternatively, $R^{2a}$ and $R^{2b}$ join to form a four- to seven-membered carbocyclic or heterocyclic ring, optionally substituted with from 1 to 4 $R^9$ groups;
$R^3$ is selected from the group consisting of hydrogen, $R^{10}$, and $C_{7-11}$ arylalkyl, optionally substituted with from 1 to 4 $R^9$ groups;
$R^{4a}$ and $R^{4b}$ are each independently selected from the group consisting of N and CH;
$R^{5a}$ and $R^{5b}$ are selected from the group consisting of hydrogen, $C_{1-3}$ alkyl, $C_{3-5}$ cycloalkyl, $C_{1-3}$ haloalkyl, $C_{1-3}$ alkoxy, $C_{1-3}$ haloalkoxy, $C_{1-3}$ hydroxyalkyl, halo, hydroxyl, cyano, amino, —(CO)OH, —(CO)(O—$C_{1-6}$ alkyl), —(CO)NH$_2$, and)—(CO)NH($R^{10}$; and wherein at least one of $R^{5a}$ and $R^{5b}$ is $C_{3-5}$ cyclopropyl;
$R^{6a}$ and $R^{6b}$ are independently selected from the group consisting of hydrogen, $C_{1-3}$ alkyl, $C_{3-5}$ cycloalkyl, $C_{1-3}$ haloalkyl, $C_{1-3}$ alkoxy, $C_{1-3}$ haloalkoxy, $C_{1-3}$ hydroxyalkyl, halo, hydroxyl, cyano, amino, —(CO)OH, —(CO)(O—$C_{1-6}$ alkyl), —(CO)NH$_2$; or, alternatively, $R^{6a}$ and $R^{6b}$ join to form a four- to seven-membered carbocyclic or heterocyclic ring, optionally substituted with from 1 to 4 $R^9$ groups and —(CO)NH($R^{10}$);

each $R^7$ is independently selected from the group consisting of hydrogen, $C_{1-3}$ alkyl, $C_{3-5}$ cycloalkyl, $C_{1-3}$ haloalkyl, $C_{1-3}$ hydroxyalkyl, and $C_{4-5}$ cycloalkylalkyl;

each $R^9$ is independently selected from the group consisting of $C_{1-6}$ alkyl, $C_{3-6}$ cycloalkyl, $C_{1-6}$ haloalkyl, $C_{1-6}$ alkoxy, $C_{1-6}$ haloalkoxy, $C_{1-6}$ hydroxyalkyl, halo, hydroxyl, cyano, amino, —(CO)OH, —(CO)(O—$C_{1-6}$ alkyl), —(CO)NH$_2$, —O(CO)R$^7$, and —NH(CO)R$^7$;

each $R^{10}$ is independently selected from the group consisting of $C_{1-6}$ alkyl, optionally substituted with 1 to 4 $R^{12}$ groups;

each $R^{11}$ is independently selected from the group consisting of $C_{1-6}$ alkyl, $C_{7-11}$ arylalkyl, and $C_{4-10}$ heteroarylalkyl, wherein said $R^{11}$ is further substituted with 1 to 4 $R^{12}$ groups;

each $R^{12}$ is independently selected from the group consisting of $C_{1-6}$ alkyl, $C_{3-6}$ cycloalkyl, $C_{1-6}$ haloalkyl, $C_{1-6}$ alkoxy, $C_{1-6}$ haloalkoxy, $C_{1-6}$ hydroxyalkyl, halo, hydroxyl, cyano, amino, —(CO)NH$_2$, —(CO)NH($C_{1-6}$ alkyl), —(CO)OH, —(CO)(O—$C_{1-6}$ alkyl), —(CO)NH$_2$, $C_{6-10}$ aryl, and $C_{2-9}$ heteroaryl.

In certain aspects and embodiments, the present invention sets forth the compound as otherwise disclosed herein, wherein L is a single bond or —CH$_2$—.

In certain aspects and embodiments, the present invention sets forth the compound as otherwise disclosed herein, wherein —L—Y— is —CH$_2$—C(=O)—.

In certain aspects and embodiments, the present invention sets forth the compound as otherwise disclosed herein, wherein Y is —C(=O)—.

In certain aspects and embodiments, the present invention sets forth the compound as otherwise disclosed herein, wherein Z is —C(=O)—NH—.

In certain aspects and embodiments, the present invention sets forth the compound as otherwise disclosed herein, wherein $R^1$ is an aryl group.

In certain aspects and embodiments, the present invention sets forth the compound as otherwise disclosed herein, wherein $R^1$ is a heteroaryl group.

Figure 8:
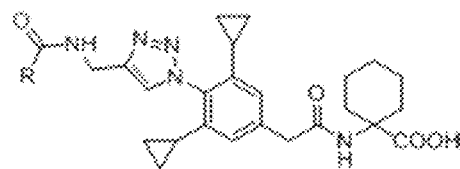
FIG. 8. (A) Structures of in situ triazoles generated from solid phase synthesis and (B) their corresponding phosphatase activity after click reactions with OPZ using the two plates ASV1 and ASV2 (+5 µM ABA). In each plate, wells C12-E12 and C12-E12 represent ABA controls (5 µM), F1-H1 and F12-H12 represent mock controls (receptor/PP2C, no ABA) and A1 and A12 contain triazoles 48E8T (0.5 µM) or 49A2T (0.5 µM, B 1, B12) in presence of 5 µM ABA.
Figure 8:
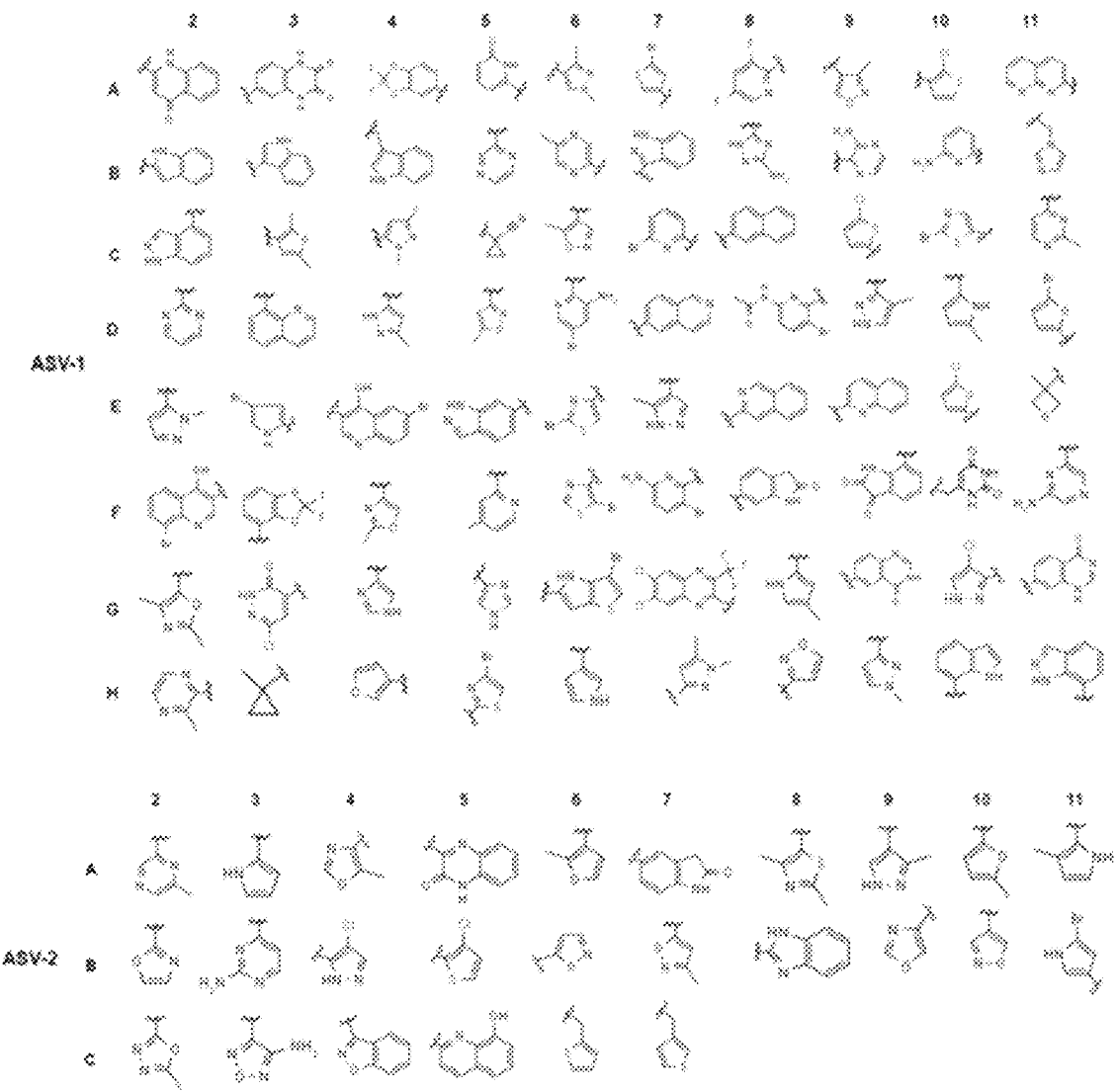

In certain aspects and embodiments, the present invention sets forth the compound as otherwise disclosed herein, wherein $R^1$ is selected from the group consisting of the R substituents of FIG. 8.

In certain aspects and embodiments, the present invention sets forth the compound as otherwise disclosed herein, wherein $R^1$ is selected from the group consisting of the R substituents of Example 9.

Figure 16:
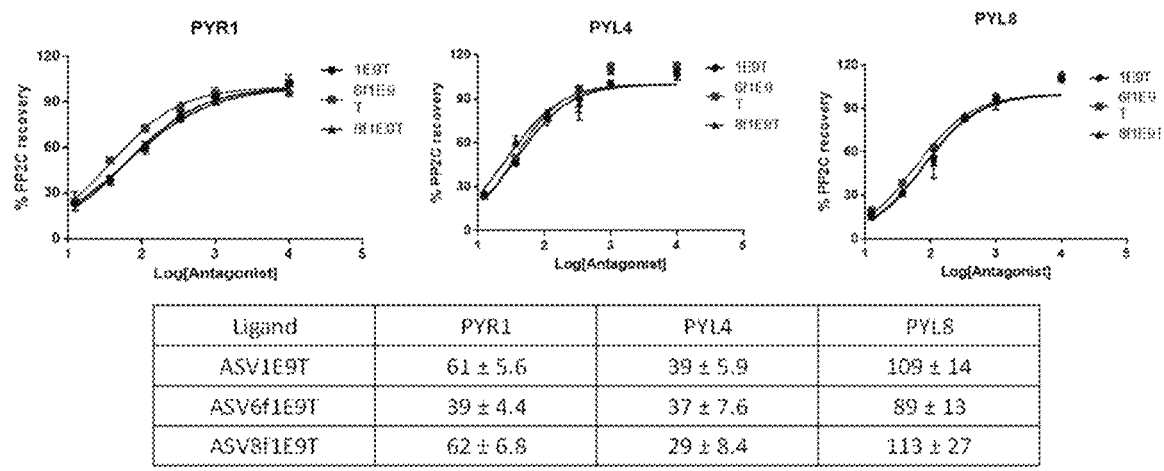
FIG. 16. Structures of azide building blocks 3CBZ and OPZ and their corresponding triazoles formed by click reaction with alkyne 48E9 and their antagonist potency against different *Arabidopsis* receptors, as measured using agonist/receptor-mediated inhibition of ΔN-HAB1 phosphatase activity (n=3). All assays contained 50 nM receptor and 25 nM ΔN-HAB1 except PYL4 where the receptor concentration was 100 nM.
Figure 16:
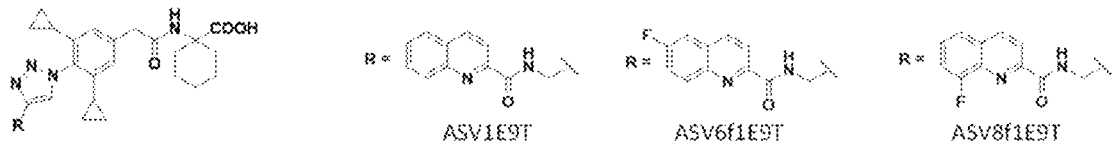
Figure 17:
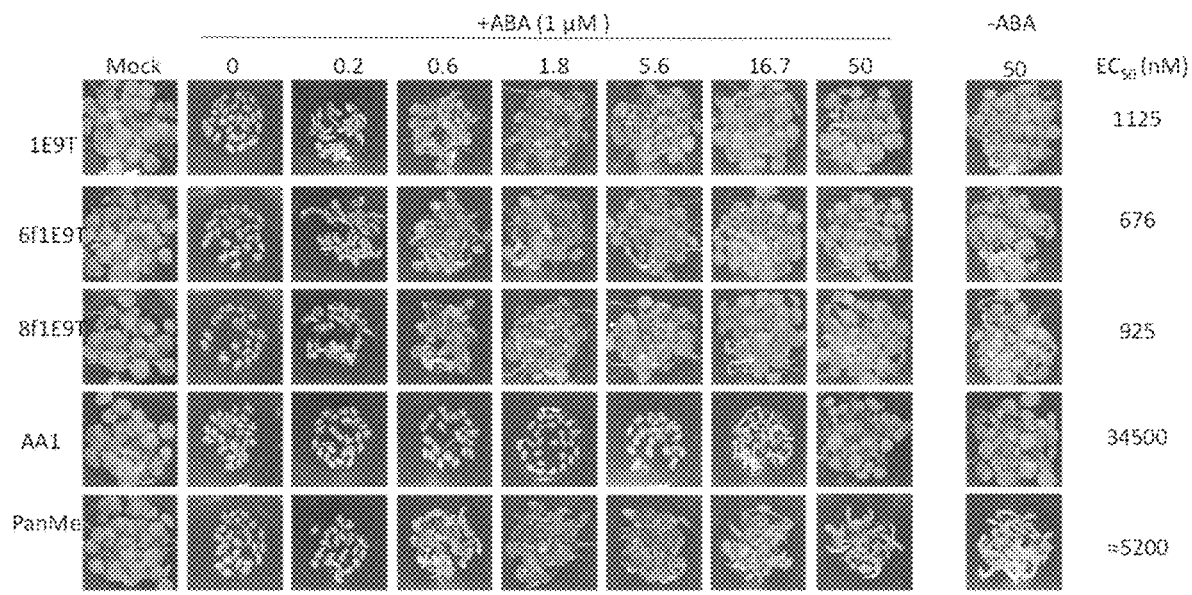
FIG. 17. Plate results from in vivo activity assays of antagonists from FIG. 16.
Figure 18:
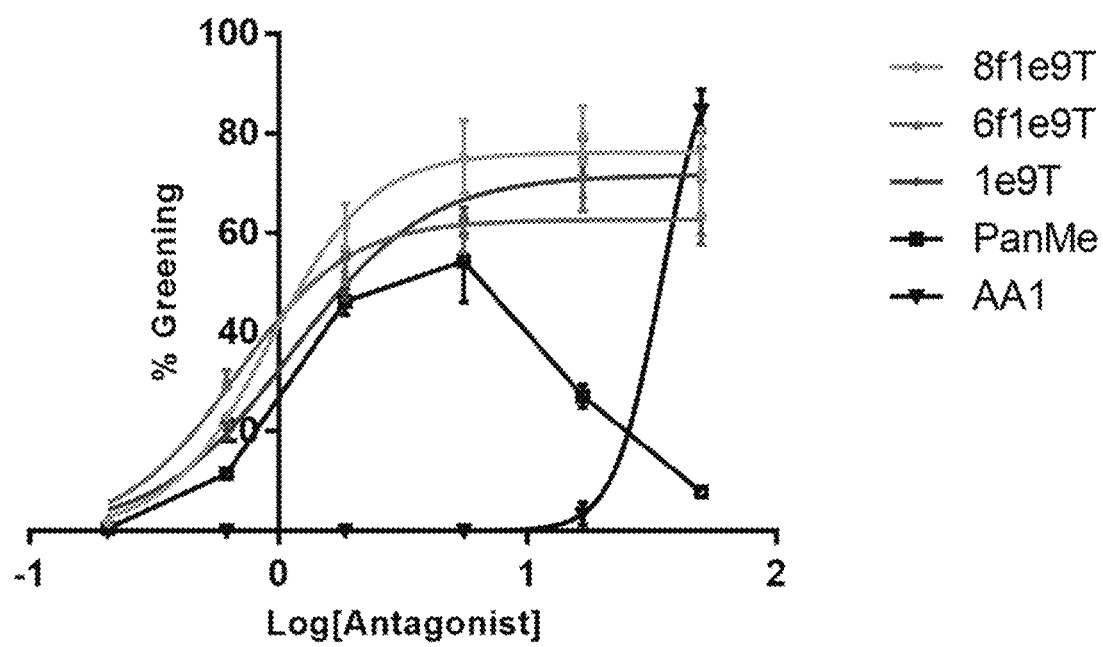
FIG. 18. Results from greening assays of antagonists from FIG. 16.

In certain aspects and embodiments, the present invention sets forth the compound as otherwise disclosed herein, wherein $R^1$ is selected from the group consisting of the R substituents of FIG. 16.

In certain aspects and embodiments, the present invention sets forth the compound as otherwise disclosed herein, wherein $R^{2a}$ and $R^{2b}$ join to form a spirocyclohexyl or spirocyclopentyl group, optionally substituted with from 1 to 4 $R^9$ groups.

In certain aspects and embodiments, the present invention sets forth the compound as otherwise disclosed herein, wherein $R^{2a}$ and $R^{2b}$ join to form a spirocyclohexyl group.

In certain aspects and embodiments, the present invention sets forth the compound as otherwise disclosed herein, wherein $R^3$ is hydrogen.

In certain aspects and embodiments, the present invention sets forth the compound as otherwise disclosed herein, wherein $R^{4a}$ and $R^{4b}$ are CH.

In certain aspects and embodiments, the present invention sets forth the compound as otherwise disclosed herein, wherein $R^{5a}$ and $R^{5b}$ are selected from the group consisting of hydrogen, $C_{1-3}$ alkyl, $C_{3-5}$ cyclopropyl, $C_{1-3}$ haloalkyl, $C_{1-3}$ alkoxy, and $C_{1-3}$ haloalkoxy.

In certain aspects and embodiments, the present invention sets forth the compound as otherwise disclosed herein, wherein $R^{6a}$ and $R^{6b}$ are hydrogen.

In certain aspects and embodiments, the present invention sets forth the compound as otherwise disclosed herein, wherein each $R^7$ is independently selected from the group consisting of hydrogen, $C_{1-3}$ alkyl, and $C_{1-3}$ haloalkyl.

In certain aspects and embodiments, the present invention sets forth the compound as otherwise disclosed herein, wherein each $R^7$ is hydrogen.

In certain aspects and embodiments, the present invention sets forth the compound as otherwise disclosed herein, wherein the group:

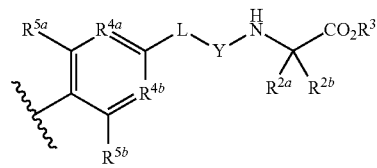

is selected from the group consisting of:

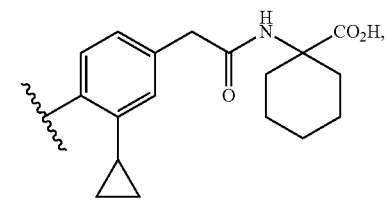

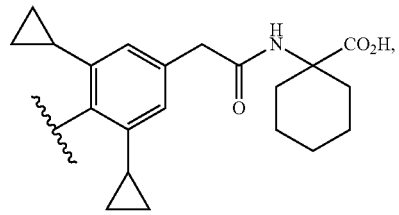

and a salt thereof.

In certain aspects and embodiments, the present invention sets forth an agricultural chemical formulation formulated for contacting to plants, the agricultural formulation comprising a carrier and the compound as otherwise disclosed herein.

In some aspects, the present invention provides an agricultural formulation consisting of, consisting essentially of, or comprising a compound as set forth herein. In some aspects, the formulation further comprises a carrier.

In certain aspects and embodiments, the present invention sets forth a method of enhancing seed germination in a plant, the method comprising contacting a seed with a sufficient amount of the formulation (as otherwise disclosed herein) to enhance germination.

In certain aspects and embodiments, the present invention sets forth a method of enhancing transpiration in a plant, the method comprising contacting the plant with a sufficient amount of the compound (as otherwise disclosed herein) to enhance transpiration.

In certain aspects and embodiments, the present invention sets forth a method of enhancing transpiration in a plant, the method comprising contacting the plant with a sufficient amount of the formulation (as otherwise disclosed herein) to enhance transpiration.

In certain aspects and embodiments, the present invention sets forth the method as otherwise disclosed herein, wherein the plant is wheat.

In certain aspects and embodiments, the present invention sets forth a method of antagonizing ABA receptor activity in a plant, the method comprising contacting the plant with a sufficient amount of the compound as otherwise disclosed herein.

In certain aspects and embodiments, the present invention sets forth a method of antagonizing ABA receptor activity in a plant, the method comprising contacting the plant with a sufficient amount of the formulation as otherwise disclosed herein.

In certain aspects and embodiments, the present invention sets forth a method of enhancing photosynthesis in a plant, the method comprising contacting the plant with a sufficient amount of the compound as otherwise disclosed herein.

In certain aspects and embodiments, the present invention sets forth a method of enhancing photosynthesis in a plant, the method comprising contacting the plant with a sufficient amount of the formulation as otherwise disclosed herein.

In some aspects, the present invention provides agricultural chemical formulations formulated for contacting to plants, wherein the formulation comprises an ABA antagonist of the present invention. In some aspects, the plants that are contacted with the antagonists comprise or express an endogenous PYR/PYL polypeptide. In some aspects the plants that are contacted with the antagonists do not comprise or express a heterologous PYR/PYL polypeptide (e.g., the plants are not transgenic or are transgenic but express heterologous proteins other than heterologous PYR/PYL proteins). In some aspects, the plants that are contacted with the antagonists do comprise or express a heterologous PYR/PYL polypeptide.

The formulations can be suitable for treating plants or plant propagation material, such as seeds, in accordance with the present invention, e.g., in a carrier. Suitable additives include buffering agents, wetting agents, coating agents, polysaccharides, and abrading agents. Exemplary carriers include water, aqueous solutions, slurries, solids and dry powders (e.g., peat, wheat, bran, vermiculite, clay, pasteurized soil, many forms of calcium carbonate, dolomite, various grades of gypsum, bentonite and other clay minerals, rock phosphates and other phosphorous compounds, titanium dioxide, humus, talc, alginate and activated charcoal). Any agriculturally suitable carrier known to one skilled in the art would be acceptable and is contemplated for use in the present invention. Optionally, the formulations can also include at least one surfactant, herbicide, fungicide, pesticide, or fertilizer.

In some aspects, the present invention provides an agricultural formulation comprising the sulfonamide antagonist compound as disclosed herein and an agriculturally acceptable adjuvant.

In some embodiments, the formulation further comprises at least one of a fungicide, an herbicide, a pesticide, a nematicide, an insecticide, a plant activator, a synergist, an herbicide safener, a plant growth regulator, an insect repellant, an acaricide, a molluscicide, or a fertilizer.

In some aspects, the agricultural formulation further comprises a surfactant.

In some embodiments, the agricultural chemical formulation comprises at least one of a surfactant, an herbicide, a pesticide, such as but not limited to a fungicide, a bactericide, an insecticide, an acaricide, and a nematicide, a plant activator, a synergist, an herbicide safener, a plant growth regulator, an insect repellant, or a fertilizer. In some embodiments, the formulation further comprises a surfactant.

In some embodiments, the agricultural chemical formulation comprises an effective amount of one or more herbicides selected from paraquat (592), mesotrione (500), sulcotrione (710), clomazone (159), fentrazamide (340), mefenacet (491), oxaziclomefone (583), indanofan (450), glyphosate (407), prosulfocarb (656), molinate (542), triasulfuron (773), halosulfuron-methyl (414), or pretilachlor (632). The above herbicidal active ingredients are described, for example, in "The Pesticide Manual", Editor C. D. S. Tomlin, 12th Edition, British Crop Protection Council, 2000, under the entry numbers added in parentheses; for example, mesotrione (500) is described therein under entry number 500. The above compounds are described, for example, in U.S. Pat. No. 7,338,920, which is incorporated by reference herein in its entirety.

In some embodiments, the agricultural chemical formulation comprises an effective amount of one or more fungicides selected from sedaxane, fludioxonil, penthiopyrad, prothioconazole, flutriafol, difenoconazole, azoxystrobin, captan, cyproconazole, cyprodinil, boscalid, diniconazole, epoxiconazole, fluoxastrobin, trifloxystrobin, metalaxyl, metalaxyl-M (mefenoxam), fluquinconazole, fenarimol, nuarimol, pyrifenox, pyraclostrobin, thiabendazole, tebuconazole, triadimenol, benalaxyl, benalaxyl-M, benomyl, carbendazim, carboxin, flutolanil, fuberizadole, guazatine, myclobutanil, tetraconazole, imazalil, metconazole, bitertanol, cymoxanil, ipconazole, iprodione, prochloraz, pencycuron, propamocarb, silthiofam, thiram, triazoxide, triticonazole, tolylfluanid, or a manganese compound (such as mancozeb, maneb). In some embodiments, the agricultural chemical formulation comprises an effective amount of one or more of an insecticide, an acaricide, or a nematcide selected from thiamethoxam, imidacloprid, clothianidin, lamda-cyhalothrin, tefluthrin, beta-cyfluthrin, permethrin, abamectin, fipronil, or spinosad. Details (e.g., structure, chemical name, commercial names, etc) of each of the above pesticides with a common name can be found in the e-Pesticide Manual, version 3.1, 13th Edition, Ed. CDC Tomlin, British Crop Protection Council, 2004-05. The above compounds are described, for example, in U.S. Pat. No. 8,124, 565, which is incorporated by reference herein in its entirety.

In some embodiments, the agricultural chemical formulation comprises an effective amount of one or more fungicides selected from cyprodinil ((4-cyclopropyl-6-methylpyrimidin-2-yl)-phenyl-amine) (208), dodine (289); chlorothalonil (142); folpet (400); prothioconazole (685); boscalid (88); proquinazid (682); dithianon (279); fluazinam (363); ipconazole (468); or metrafenone. Some of the above compounds are described, for example, in "The Pesticide Manual" [The Pesticide Manual—A World Compendium; Thirteenth Edition; Editor: C. D. S. Tomlin; The British Crop Protection Council, 2003], under the entry numbers added in parentheses. The above compounds also are described, for example, in U.S. Pat. No. 8,349,345, which is incorporated by reference herein in its entirety.

In some embodiments, the agricultural chemical formulation comprises an effective amount of one or more fungicides selected from fludioxonil, metalaxyl, or a strobilurin fungicide, or a mixture thereof. In some embodiments, the strobilurin fungicide is azoxystrobin, picoxystrobin, kresoxim-methyl, or trifloxystorbin. In some embodiments, the agricultural chemical formulation comprises an effective amount of one or more of an insecticide selected from a phenylpyrazole or a neonicotinoid. In some embodiments, the phenylpyrazole is fipronil and the neonicotinoid is selected from thiamethoxam, imidacloprid, thiacloprid, clothianidin, nitenpyram or acetamiprid. The above compounds are described, for example, in U.S. Pat. No. 7,071,188, which is incorporated by reference herein in its entirety. In some embodiments, the agricultural chemical formulation comprises an effective amount of one or more biological pesticide, including but not limited to, Pasteuria spp., Paeciliomyces, Pochonia chlamydosporia, *Myrothecium* metabolites, Muscodor volatiles, *Tagetes* spp., *Bacillus firmus*, including *Bacillus firmus* CNCM I-1582.

In some aspects, the present invention sets forth a method of increasing stress tolerance in a plant, the method comprising contacting the plant with a sufficient amount of a formulation otherwise disclosed herein so as to increase stress tolerance in the plant compared to not contacting the plant with the formulation. In some aspects, the plant is a seed. In some aspects, the stress tolerance is drought tolerance.

In some embodiments, the plant is a monocot. In some alternative embodiments, the plant is a dicot. In some embodiments, the abiotic stress tolerance comprises drought tolerance.

The types of plant that can be treated with the ABA antagonists described herein include both monocotyledonous (i.e., monocot) and dicotyledonous (i.e., dicot) plant species including cereals such as barley, rye, sorghum, tritcale, oats, rice, wheat, soybean and corn; beets (for example sugar beet and fodder beet); cucurbits including cucumber, muskmelon, cantaloupe, squash and watermelon; cole crops including broccoli, cabbage, cauliflower, bok choi, and other leafy greens, other vegetables including tomato, pepper, lettuce, beans, pea, onion, garlic and peanut; oil crops including canola, peanut, sunflower, rape, and soybean; solanaceous plants including tobacco; tuber and root crops including potato, yam, radish, beets, carrots and sweet potatoes; fruits including strawberry; fiber crops including cotton and hemp; other plants including coffee, bedding plants, perennials, woody ornamentals, turf and cut flowers including carnation and roses; sugar cane; containerized tree crops; evergreen trees including fir and pine; deciduous trees including maple and oak; and fruit and nut trees including cherry, apple, pear, almond, peach, walnut and citrus.

In some embodiments, the contacting step comprises delivering the formulation to the plant by aircraft or irrigation.

The ABA antagonist compounds or formulations can be applied to plants using a variety of known methods, e.g., by spraying, atomizing, dipping, pouring, irrigating, dusting or scattering the formulations over the propagation material, or brushing or pouring or otherwise contacting the formulations over the plant or, in the event of seed, by coating, encapsulating, spraying, dipping, immersing the seed in a liquid formulation, or otherwise treating the seed. In an alternative to directly treating a plant or seed before planting, the formulations of the invention can also be introduced into the soil or other media into which the seed is to be planted. For example, the formulations can be introduced into the soil by spraying, scattering, pouring, irrigating or otherwise treating the soil. In some embodiments, a carrier is also used in this embodiment. The carrier can be solid or liquid, as noted above. In some embodiments peat is suspended in water as a carrier of the ABA antagonist, and this mixture is sprayed into the soil or planting media or over the seed as it is planted.

It will be understood that the ABA antagonists described herein mimic the function of ABA on cells. Thus, it is expected that one or more cellular responses triggered by contacting the cell with ABA will also be triggered be contacting the cell with the ABA antagonists described herein. The ABA antagonists described herein mimic the function of ABA and are provided in a useful formulation.

In some aspects, the present invention sets forth a method of enhancing seed germination in a plant, the method comprising contacting a seed with a sufficient amount of a formulation otherwise disclosed herein to enhance germination.

In some aspects, the present invention sets forth a method of enhancing transpiration in a plant, the method comprising contacting the plant with a sufficient amount of a formulation otherwise disclosed herein to enhance transpiration. In some aspects, the plant is wheat.

In some aspects, the present invention sets forth a method of antagonizing ABA receptor activity in a plant, the method comprising contacting the plant with a sufficient amount of a formulation otherwise disclosed herein.

It is understood that the examples and embodiments described herein are for illustrative purposes only. Various modifications or changes in light thereof will be suggested to persons skilled in the art and are to be included within the spirit and purview of this application and the scope of the appended claims. All publications, sequence accession numbers, patents, and patent applications cited herein are hereby incorporated by reference in their entirety for all purposes.

EXAMPLES

Example 1-a Click Chemistry Approach to Identify ABA Antagonists

We recently described the potent bbABA agonist opabactin (OP), which has a C4-nitrile substituent that mimics ABA's C4' ring ketone. Our strategy to creating ABA receptor antagonists (FIG. 1) was to append domains on to the C4-position of OP and identify derivatives that either prevent gate closure or disrupt function of the closed gate conformer. To investigate this idea, we designed OPZ, which replaces OP's 4-benzylnitrile substituent with a 4-benzylazide. OPZ can be easily diversified into OP-4-triazoles using the highly efficient Cu(I) catalyzed 1-3 dipolar alkyne-azide cycloaddition commonly known as "click chemistry". A library of 4002 OP-4-triazoles was synthesized and screened using in vitro ABA receptor activation assays to identify receptor antagonists.

Example 2-Synthesis of OPZ, a Clickable OP Derivative

Figure 2:
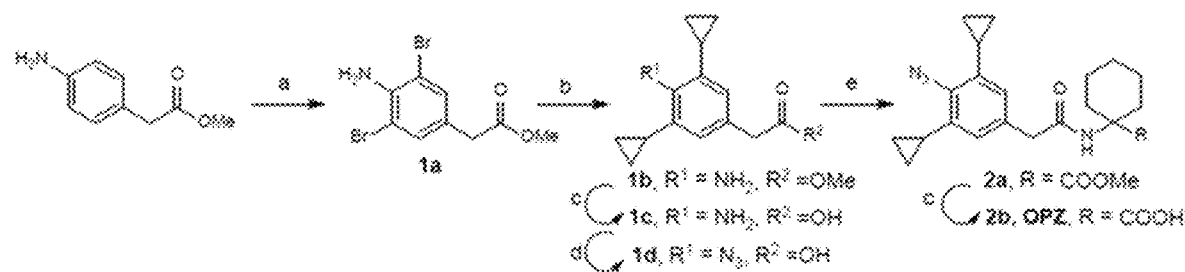
FIG. 2. Synthesis of OPZ and reagents and conditions. (a) Ammonium bromide, oxone, MeOH, 12 hr; (b) Cyclopropyl boronic acid, $K_3PO_4$, $P(Cy)_3$, $Pd(OAc)_2$, Toluene/water, 110° C., 3 hr; (c) LiOH, MeOH/$H_2O$, RT, 24 hr; (d) $NaNO_2$, HCl, $NaN_3$, 0-RT, 12 hr; (e) Methyl 1-aminocyclohexanoate, EDCI, DMAP, DCM, 0° C.-RT, 12 hr.

Reactions to synthesize desired compounds were carried out under an atmosphere of argon in oven-dried glassware, unless otherwise stated. Indicated reaction temperatures refer to those of the reaction bath, while room temperature (rt) is noted as 25° C. All other solvents were of anhydrous quality purchased from Aldrich Chemical Co. and used as received. Pure reaction products were typically dried under high vacuum. Commercially available starting materials and reagents were purchased from Aldrich, TCI, Fisher Scientific, Combiblocks, Click Chemistry Tools and AK Scientific and were used as received unless specified otherwise. Analytical thin layer chromatography (TLC) was performed with (5×20 cm, 60 Å, 250 µm). Visualization was accomplished using a 254 nm UV lamp. $^1$NMR and $^{13}$C NMR spectra were recorded on Bruker 700 MHz. Chemical shifts are reported in ppm with the solvent resonance as internal standard ([DMSO-d6 2.5 ppm] for $^1$H, $^{13}$C respectively). Data are reported as follows: chemical shift, multiplicity (s=singlet, d=doublet, dd=doublet of doublet, t=triplet, q=quartet, br=broad, m=multiplet), number of protons, and coupling constants. Products exact masses were obtained by analysis on an Agilent 6224 TOF LC-MS using electrospray ionization in positive ion mode, using an Agilent Poroshell 120 3×50 mm, C18-column, particle size 2.7 μm (Agilent, Part number: 699975-302). LC conditions were as follows: flow rate was set to 0.5 mL/min, using a mixture of acetonitrile/0.1% formic acid/water. Gradients were as follows: 0→>2 min: 2% acetonitrile; linear increase to 90% acetonitrile between 2→17 min (3 min: 15% acetonitrile, 5 min: 25% acetonitrile, 10 min: 40% acetonitrile, 12 min: 70% acetonitrile, 17 min: 90% acetonitrile); 17→22.5 min: 90% acetonitrile; 22.5→23 min: linear decrease to 2% acetonitrile; 23→>25.5 min: 2% acetonitrile. Elution was monitored by UV absorption at 254 nm and by MS-TOF. The positive ion mode ESI conditions were as follows: gas temperature 325° C., drying gas flow rate 11 L/min, nebulizer 35 psig and VCap 3500V. MS TOF conditions were as follows: fragmentor 120V and skimmer 65V. MassHunter (Agilent Technologies, version B.04.00) was used to determine the exact mass of the compounds of interest and UV spectra checked to confirm sample purity. All compounds used for biological assays were ≥95% pure. (+)-ABA and AA1 were commercially available and purchased from BioSynth and Life Chemicals respectively, whereas the ligand PanMe was synthesized according a literature procedure (25. OPZ was synthesized over six steps as outlined in FIG. 2 below.

Methyl (4-amino-3,5-dibromophenyl)acetate (1a). To a solution of Methyl (p-aminophenyl)acetate (5 g, 30.26 mmoles, 1 equiv) in anhydrous methanol was added ammonium bromide (5.93 g, 60.52 mmoles, 2 equiv) followed by oxone (9.21 g, 60.52 mmoles, 2 equiv) portion wise and the reaction stirred overnight. After completion of reaction (TLC), the reaction was concentrated in vacuo, adsorbed on silica and purified by silica gel flash chromatography using hexane/ethyl acetate gradient to yield 4.63 g of 1a as a pale yellow solid in 48% yield. $^1$H NMR (700 MHz, DMSO-d6) δ ppm 3.56 (s, 2H), 3.61 (s, 2H), 5.27 (br s, 2H), 7.53 (s, 2H). $^{11}$C NMR (176 MHz, DMSO-d6) δ ppm 38.33, 52.20, 107.79, 125.17, 133.26, 142.08, 172.10.

Methyl (4-amino-3,5-dicyclopropylphenyl)acetate (1b) To a solution of 1a (3.72 g, 11.52 mmoles, 1 equiv) in toluene/water (12 ml toluene: 600 uL water) was added K$_3$PO$_4$ (8.56 g, 40.31 mmoles, 3.5 equiv), P(Cy)$_3$ (323 mg, 1.15 mmoles, 0.1 equiv), Pd(OAc)$_2$ (129.3 mg, 0.578 mmoles, 0.05 equiv) and cyclopropyl boronic acid (2.47 g, 28.8 mmoles, 2.5 equiv) and heated in a pressure vessel at 110° C. for 3 hours. After completion of reaction (TLC), the reaction was concentrated in vacuo, adsorbed on silica and purified by silica gel flash chromatography using hexane/ethyl acetate gradient to yield 2.63 g of 1b as a off white crystalline solid in 93% yield. $^1$H NMR (700 MHz, DMSO-d6) δ ppm 0.44-0.46 (m, 4H), 0.85-0.88 (m, 4H), 1.66-1.68 (m, 2H), 3.41 (s, 2H), 3.57 (s, 3H), 4.75 (br s, 2H), 6.62 (s, 2H). NMR (176 MHz, DMSO-d6) δ ppm 6.01, 11.76, 51.91, 121.31, 125.43, 126.16, 145.84, 172.78.

(4-Amino-3,5-dicyclopropylphenyl)acetic acid (1c). To a solution of 1b (2.63 g, 10.73 mmoles, 1 equiv) in 20 mL of methanol/water (1:1 v/v) was added lithium hydroxide (2.57 g, 107.3 mmoles, 10 equiv) and stirred at room temperature for 24 hr. After completion of reaction (TLC), the reaction, 2N HCl was added to precipitate the product, 1c as a white solid (near quantitative yield) which was filtered, dried and used in the next step without further purification. $^1$H NMR (700 MHz, DMSO-d6) δ ppm 0.44-0.46 (m, 4H), 0.85-0.88 (m, 4H), 1.65-1.69 (m, 2H), 3.31 (s, 2H), 6.62 (s, 2 H). $^{13}$C NMR (176 MHz, DMSO-d6) δ ppm 5.99, 11.77, 122.04, 125.34, 126.18, 145.64, 173.88.

(4-Azido-3,5-dicyclopropylphenyl)acetic acid (1d) To an ice cold solution of 1c (0.9 g, 3.89 mmoles, 1 equiv) in acetonitrile/water (1:1) was added concentrated hydrochloric acid dropwise 5 mL, followed by a cold aqueous solution of sodium nitrite (0.4 g, 5.84 mmoles, 1.5 equiv). The reaction stirred at 0° C. for 20 min. Thereafter a cold aqueous solution of sodium azide (0.76 g, 11.67 mmoles, 3 equiv) was added dropwise so as to control the effervescence of nitrogen gas observed. The reaction was stirred at 0° C. for a further 1 hr and left to attain room temperature overnight. After completion of reaction (TLC), 2N HCl was added to the reaction mixture, and the reaction extracted three times with ethyl acetate (30 mL). The organic extracts were combined and dried over anhydrous sodium sulfate and concentrated in vacuo. The residue was adsorbed on silica gel and purified by flash chromatography using a hexane/ethyl acetate gradient to yield 0.82 g of 1d as an off white solid in 83% yield. $^1$H NMR (700 MHz, DMSO-d6) δ ppm 0.66-0.68 (m, 4H), 0.97-0.99 (m, 4H), 2.09-2.13 (m, 2H), 3.46 (s, 2H), 6.75 (s, 2H). $^{13}$C NMR (176 MHz, DMSO-d6) δ ppm 8.44, 12.09, 125.46, 133.18, 136.62, 136.84, 173.03.

Methyl 1-[2—(4-azido-3,5-dicyclopropylphenyl)acetylamino]cyclohexane-carboxylate (2a) To an ice cold solution of 1d (0.82 g, 3.18 mmoles, 1 equiv) in anhydrous dichloromethane was added 1-aminocyclohexanoate (0.6 g, 3.82 mmoles, 1.2 equiv), EDCI (0.91 g, 4.77 mmoles, 1.5 equiv) and DMAP (0.58g, 4.77 mmoles, 1.5 equiv) and the reaction stirred overnight at room temperature. After completion of reaction (TLC), the reaction was concentrated in vacuo, adsorbed on silica and purified by silica gel flash chromatography using hexane/ethyl acetate gradient to 2a as a off white solid in near quantitative yield. $^1$H-NMR (700 MHz, DMSO-d6) δ ppm 0.65-0.67 (m, 4H), 0.97-0.99 (m, 4H), 1.21-1.23 (m, 1H), 1.41-1.43 (m, 5H), 1.61-1.66 (m, 2H), 1.89-1.91 (m, 2H), 2.09-2.13 (m, 2H), 3.35 (s, 2H), 3.52 (s, 3H), 6.75 (s, 2H), 8.15 (s, 2H). $^{13}$C NMR (176 MHz, DMSO-d6) δ ppm 8.42, 12.05, 21.42, 25.29, 32.19, 42.01, 52.10, 58.37, 124.73, 134.71, 136.52, 136.56, 170.25, 174.84.

142-(4-Azido-3,5-dicyclopropylphenyl)acetylaminolcyclohexanecarboxylic acid (2b; OPZ) To a solution of 2a (0.4 g, 1.01 mmoles, 1 equiv) in methanol/water 20 mL (1:1 v/v) was added lithium hydroxide (0.48 g, 20.2 mmoles, 20 equiv) and stirred at RT for 24 hr. After completion of the reaction (TLC), 2N HCl was added to the reaction mixture to precipitate the product as a white solid in near quantitative yields. The product is extremely light sensitive and stored at −20° C. until further use. $^1$H NMR (700 MHz, DMSO-d6) δppm 0.65-0.67 (m, 4H), 0.97-0.99 (m, 4H), 1.21-1.23 (m, 1H), 1.41-1.43 (m, 5H), 1.61-1.66 (m, 2H), 1.89-1.91 (m, 2H), 2.09-2.13 (m, 2H), 3.35 (s, 2H), 6.75 (s, 2H), 8.15 (s, 2H). $^{13}$C NMR (176 MHz, DMSO-d6) 5 ppm 8.42, 12.05, 21.42, 25.29, 32.19, 52.10, 58.37, 124.73, 134.71, 136.52, 136.56, 170.25, 174.84.

Figure 3:
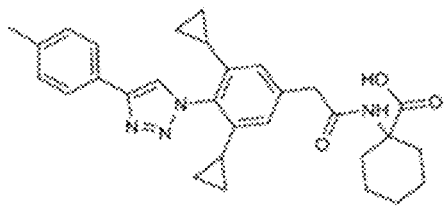
FIG. 3: Structure and analytical data for triazole T1 and ABA/PYR1-mediated PP2C activity in different conditions tested: in situ generated versus purified OP-4-triazole, OPZ and different click reagents on their own or combinations.

Example 3—Model Click Reactions Using OPZ and 4-Ethynyltoluene Demonstrate Feasibility Prior to synthesizing a library of OP-4-triazoles we conducted model click reactions to establish the feasibility and efficiency of using unpurified reaction mixtures directly in ABA receptor activation assays. These reactions were performed using OPZ and 4-ethynyltoluene as follows: we mixed OPZ (4 uL, 25 mM), alkyne (10 uL, 10 mM), sodium ascorbate (2 uL, 20 mM), BTTA (2 uL, 20 mM) and copper(II) sulphate (2 uL, 10 mM) in a 200 μL PCR tube and incubated the reaction at 37° C. for 48 hr. The reaction was monitored using TLC. In parallel, we ran a scaled-up synthesis of the triazole using similar ratios of the reagents and conditions, followed by precipitation of the product by the addition of 2N HCl and subsequent filtration to yield triazole T1 from 4-ethynyltoluene as white powder in quantitative yields. The purified triazole and unpurified click reaction were both tested in receptor-mediated phosphatase inhibition assays. We also tested the effects of the individual click reagents on PP2C activity by running PP2C assays in the presence of sodium ascorbate (50 μM), BTTA (100 μM), copper (II) sulphate (50 μM), or a combination of all the click reagents. The *Arabidopsis* receptors and PP2C ΔN-HAB1 used for this assay were expressed and purified using previously described expression clones and methods (6). Phosphatase assays were conducted in an assay buffer (100 mM Tris-HCl —pH 7.9, 100 mM NaCl, 30 μg,/ml BSA, 0.1% 2-mercaptoethanol) supplemented with 100 nM PYR1, 25 nM ΔN-HAB1, 50 μM test compound (triazole product or OPZ precursor), in the presence or absence of 5 μM ABA. Reactions were mixed and equilibrated for 20 minutes, substrate (4-methylumbelliferyl phosphate, 1 mM final) was added, and fluorescence data were collected (λ, exc=360 nm, λ emm=460 nm) using a Tecan Infinite F200 Pro fluorimeter. PP2C activity was calculated relative to solvent-only control wells (i.e. receptors and PP2C in assay buffer, but no test compound); compounds were tested in duplicate. The results of these experiments (FIG. 3) show that OPZ is weak partial PYR1 agonist/antagonist, that the click reagents individually or combined have minor effects on PP2C activity, and that both the crude in situ click reaction and purified triazole produce similar effects on PP2C activity. These data, therefore, demonstrate that unpurified click reaction products can be tested directly in in vitro ABA receptor activation assays, thus enabling facile construction and characterization of a substituted OP-4-triazole library.

Example 4-Synthesis of a 4002 Member OP-4-Triazole Library 4002 commercially available alkynes were purchased from Enamine, Asinex, Chembridge, and Urosy and solvated in DMSO as 10 mM stocks in 96-well Matrix plates (80 compounds per plate); these stock solutions were used directly in click reactions. Reactions were performed as follows (per well): OPZ (4 μL, 25 mM, solution in DMSO) was mixed with library alkyne (10 μL, 10 mM, solution in DMSO), freshly prepared-sodium ascorbate (2 μL, 20 mM, solution in water), BTTA (2 μL, 20 mM, solution in DMSO), and copper(II) sulphate (2 μL, 10 mM, solution in water) in a 96-well polypropylene PCR plate, which was covered with sealing tape and incubated at 37° C. for 48 hours. Plates were stored at −20° C. prior to their use in receptor activation assays.

Example 5-Screening of the OP-4-Triazole Library for ABA Receptor Antagonists

Figure 4:
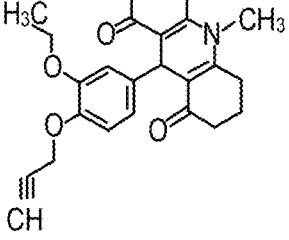
FIG. 4. Table showing vendor ID/Plate IDs for the alkynes clicked against OPZ and the phosphatase activity measured for their click reaction products (50 µM) in the presence of PYR1 (50 nM), PYL4 (100 nM), or PYL8 (50 nM) plus 25 nM HAB1 and 5 µM ABA. Shown also are the reaction efficiencies as estimated by %-consumption of OPZ from each reaction product and greening of cotyledons (normalized to mock control in presence of 10 µM OP-4-triazole and 1 µM ABA). Structures of the alkynes that yielded bioactive OP-triazoles after reaction with OPZ are provided in FIG. 4.
Figure 4:
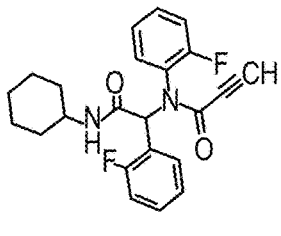
Figure 4:
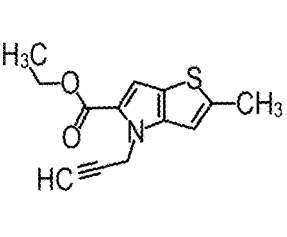
Figure 4:
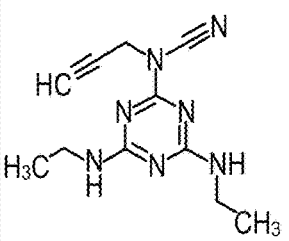
Figure 4:
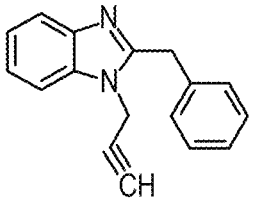
Figure 4:
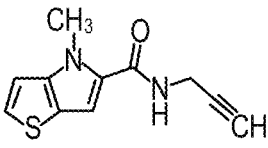
Figure 4:
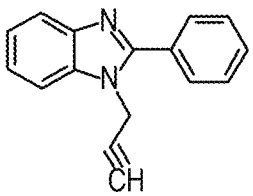
Figure 4:
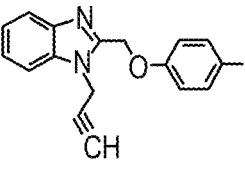
Figure 4:
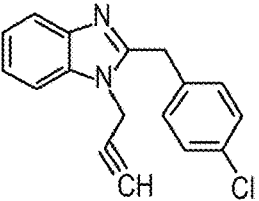
Figure 4:
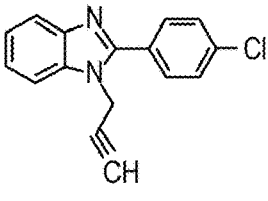
Figure 4:
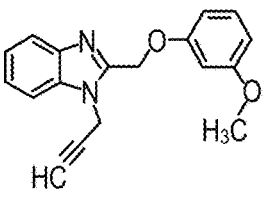
Figure 4:
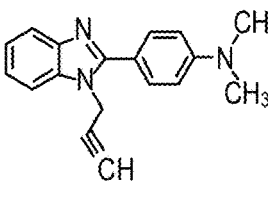
Figure 4:
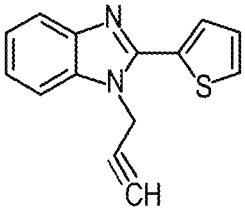
Figure 4:
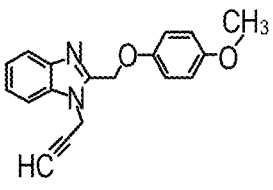
Figure 4:
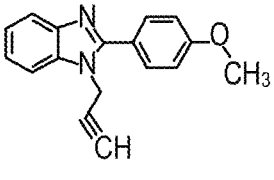
Figure 4:
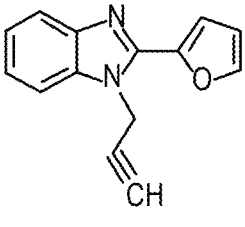
Figure 4:
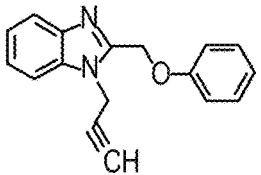
Figure 4:
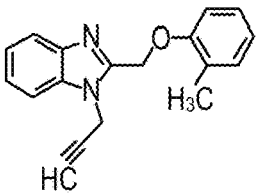
Figure 4:
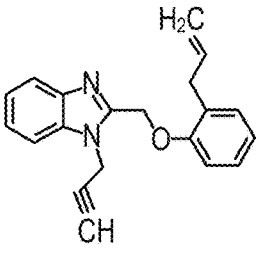
Figure 4:
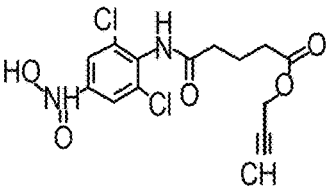
Figure 4:
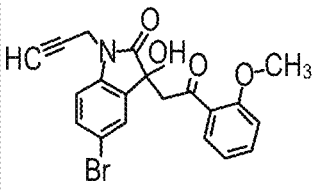
Figure 4:
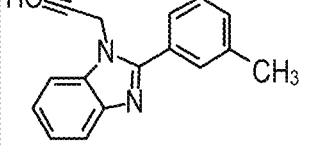
Figure 4:
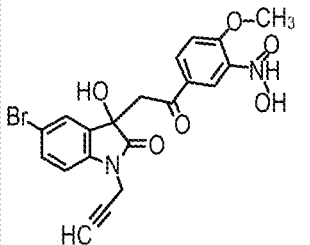
Figure 4:
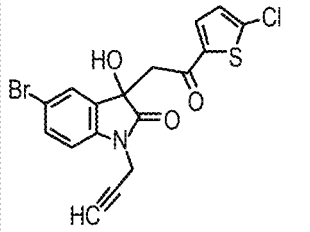
Figure 4:
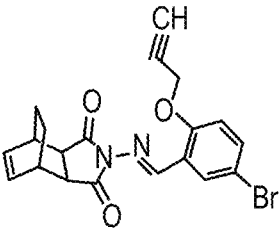
Figure 4:
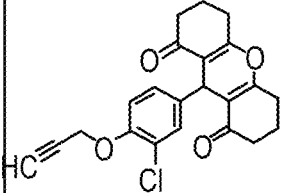
Figure 4:
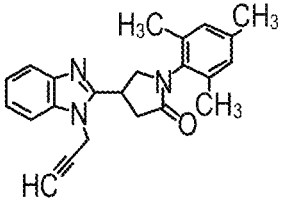
Figure 4:
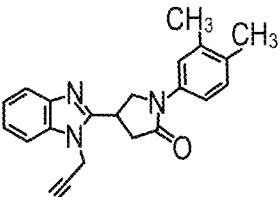
Figure 4:
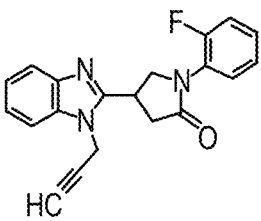
Figure 4:
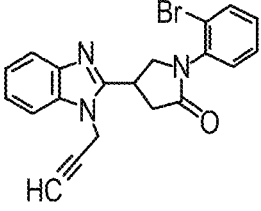
Figure 4:
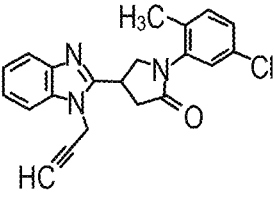
Figure 4:
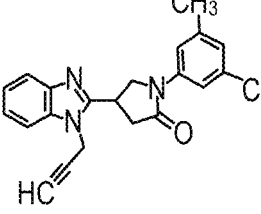
Figure 4:
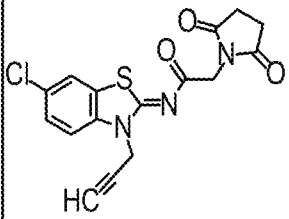
Figure 4:
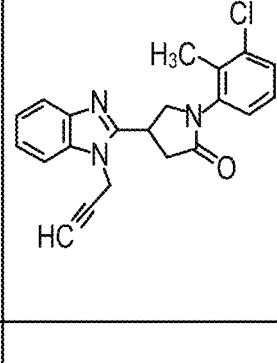
Figure 4:
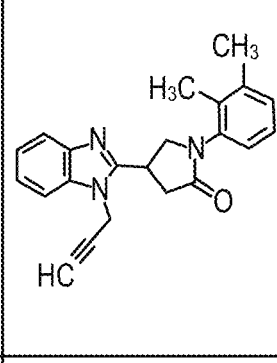
Figure 4:
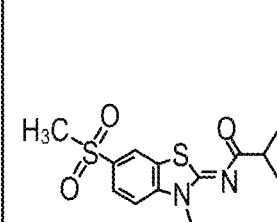
Figure 4:
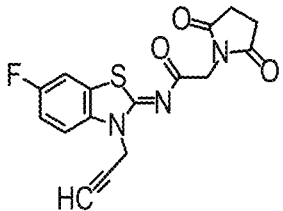
Figure 4:
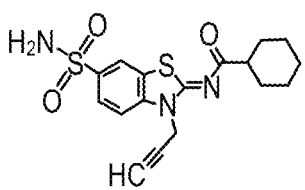
Figure 4:
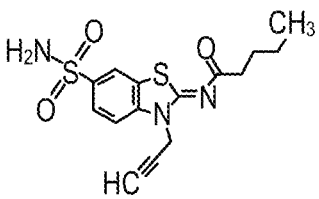
Figure 4:
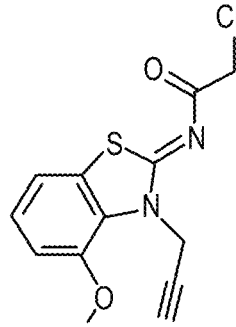
Figure 4:
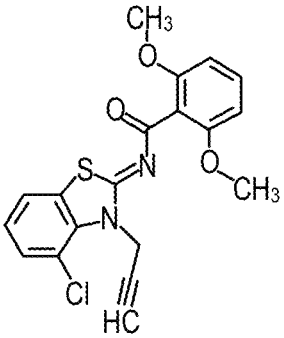
Figure 4:
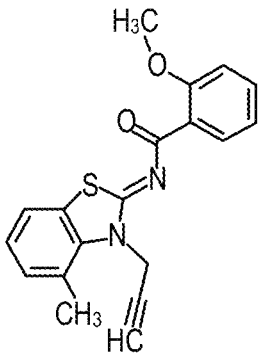
Figure 4:
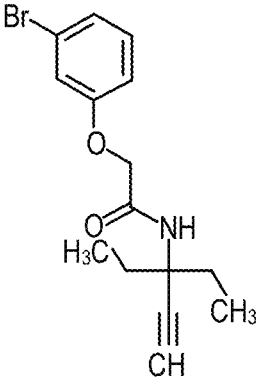
Figure 4:
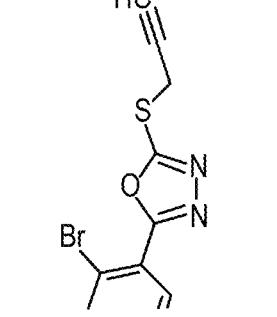
Figure 4:
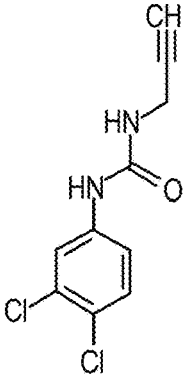
Figure 4:
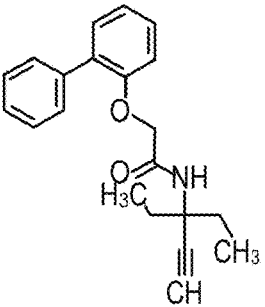
Figure 4:
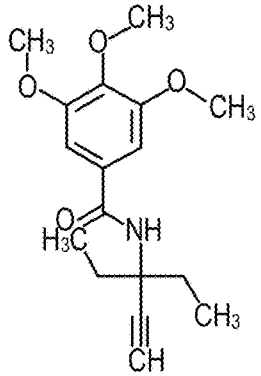
Figure 4:
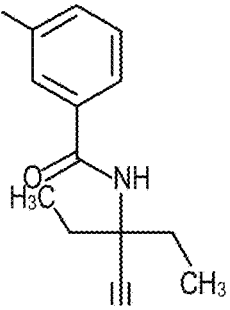
Figure 4:
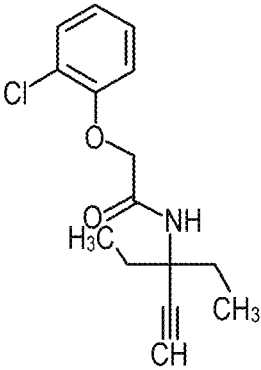
Figure 4:
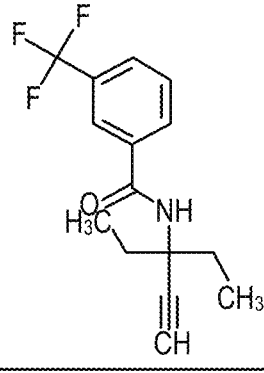
Figure 4:
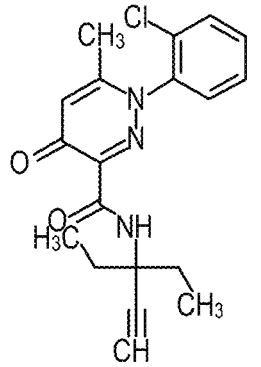
Figure 4:
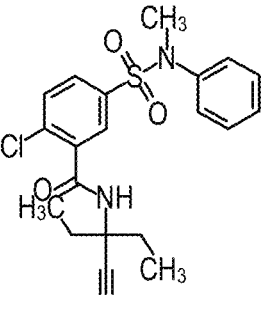
Figure 4:
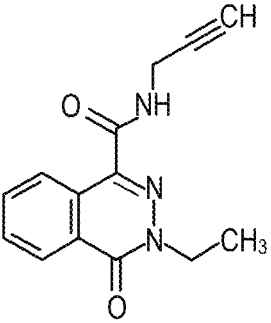
Figure 4:
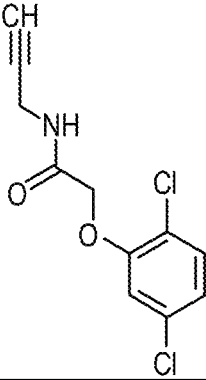
Figure 4:
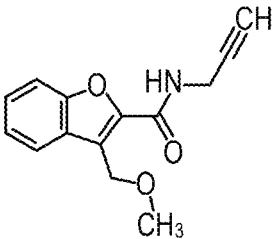
Figure 4:
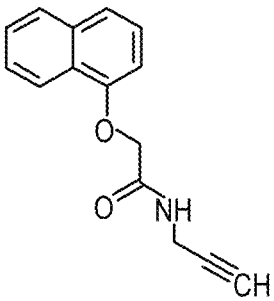
Figure 4:
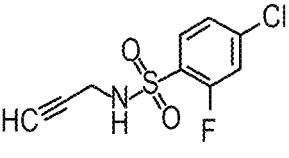
Figure 4:
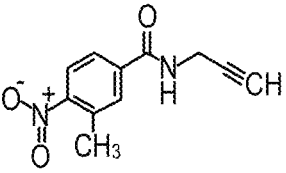
Figure 4:
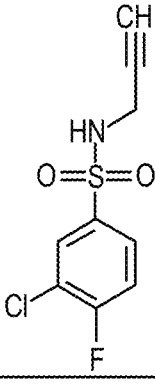
Figure 4:
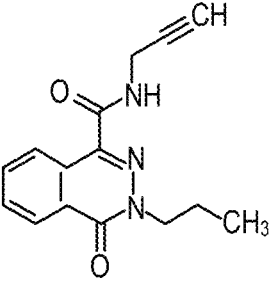
Figure 4:
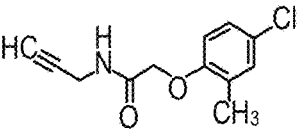
Figure 4:
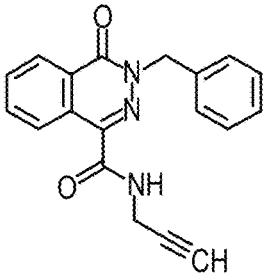
Figure 4:
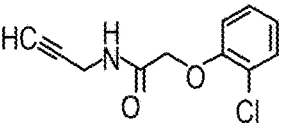
Figure 4:
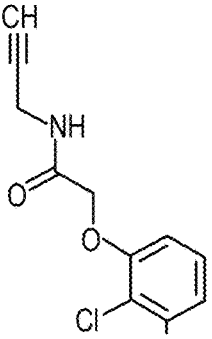
Figure 4:
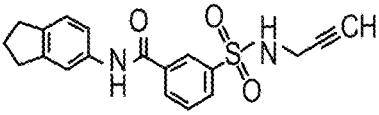
Figure 4:
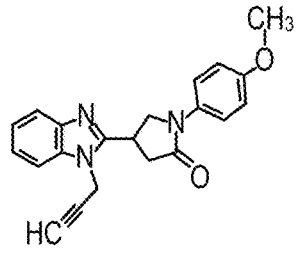
Figure 4:
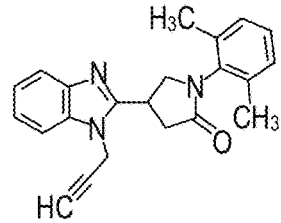
Figure 4:
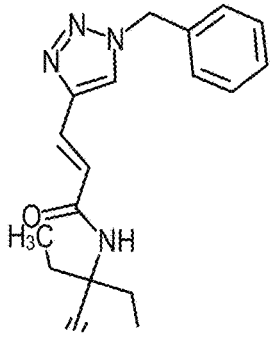
Figure 4:
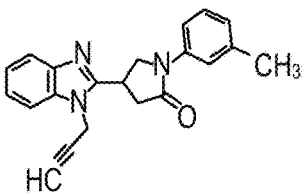
Figure 4:
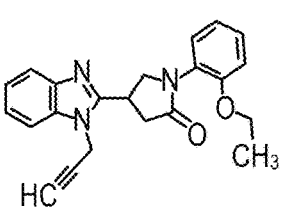
Figure 4:
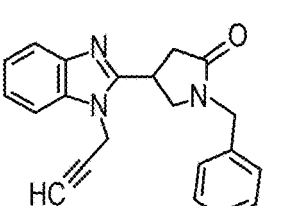
Figure 4:
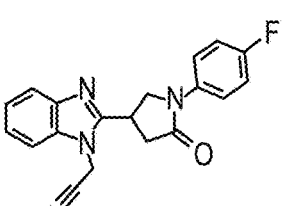
Figure 4:
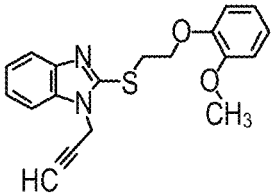
Figure 4:
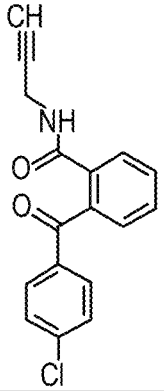
Figure 4:
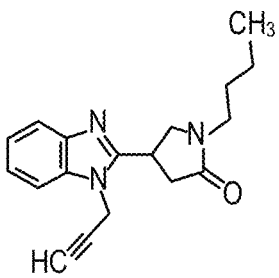
Figure 4:
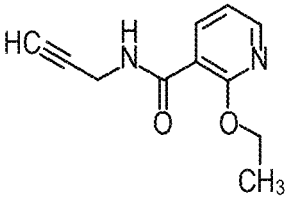
Figure 4:
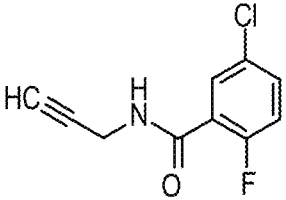
Figure 4:
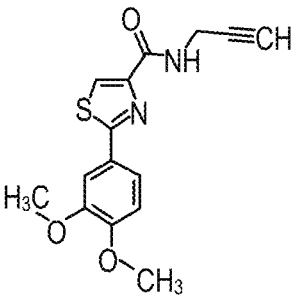
Figure 4:
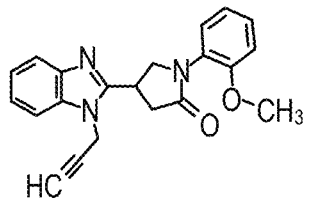
Figure 4:
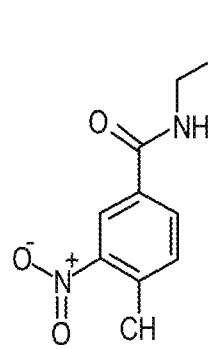
Figure 4:
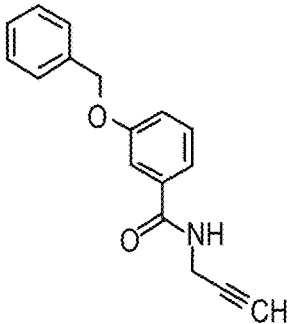
Figure 4:
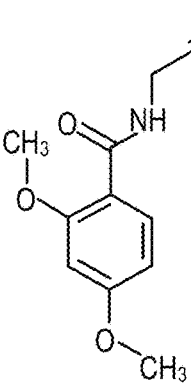
Figure 4:
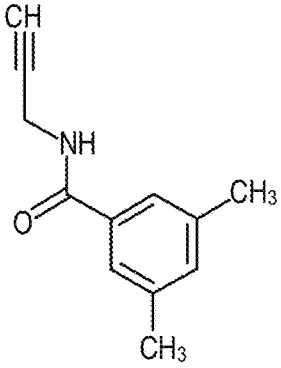
Figure 4:
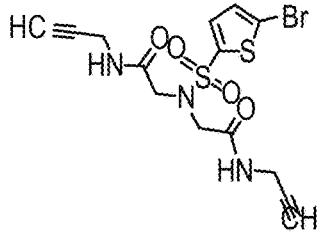
Figure 4:
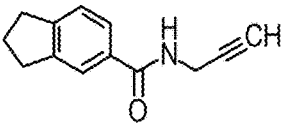
Figure 4:
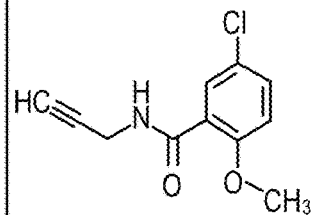
Figure 4:
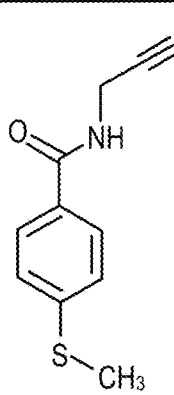
Figure 4:
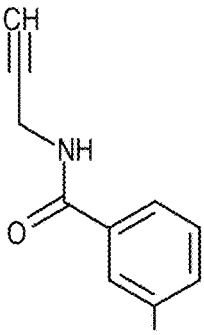
Figure 4:
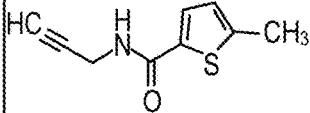
Figure 4:
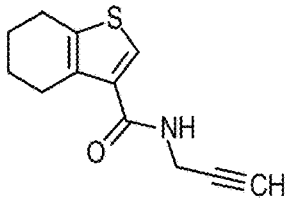
Figure 4:
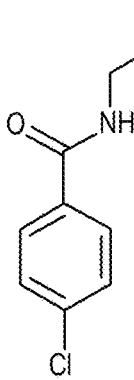
Figure 4:
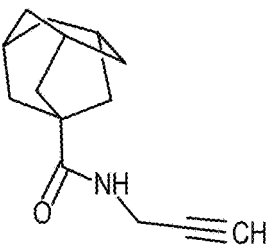
Figure 4:
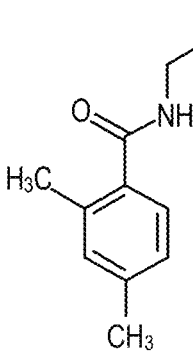
Figure 4:
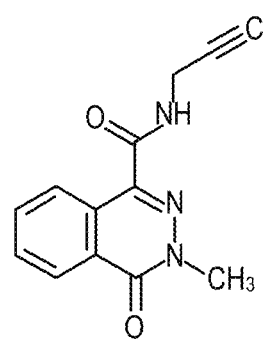
Figure 4:
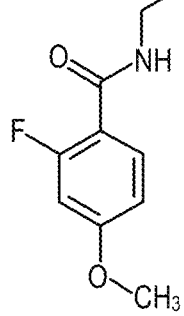
Figure 4:
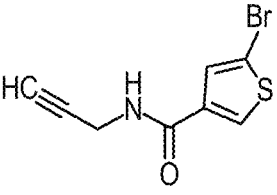
Figure 4:
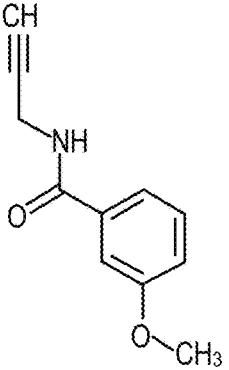
Figure 4:
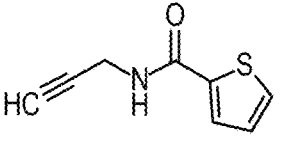
Figure 4:
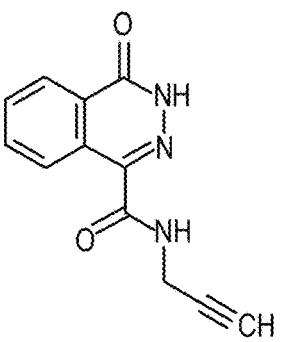
Figure 4:
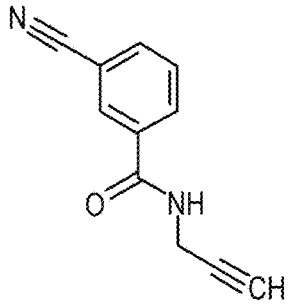
Figure 4:
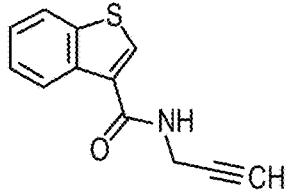
Figure 4:
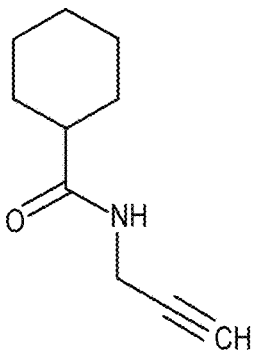
Figure 4:
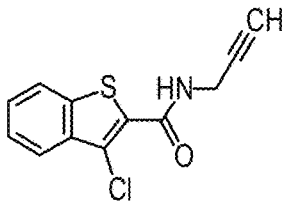
Figure 4:
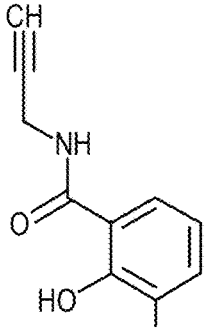
Figure 4:
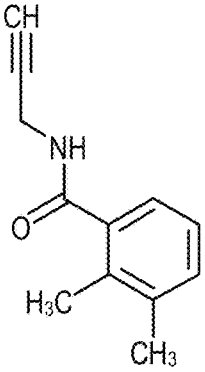
Figure 4:
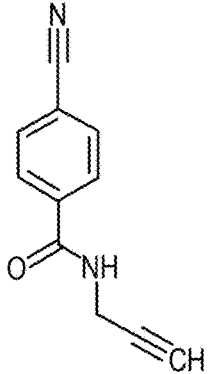
Figure 4:
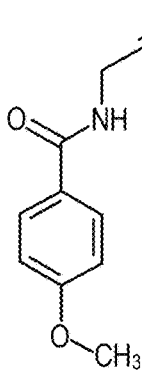
Figure 4:
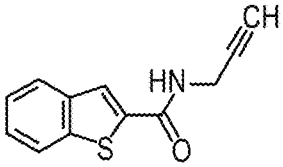
Figure 4:
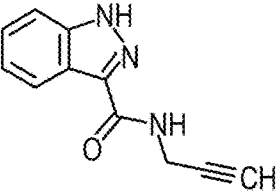
Figure 4:
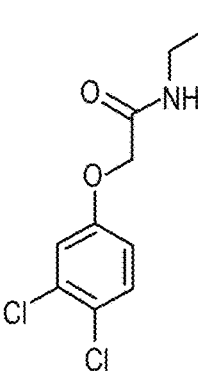
Figure 4:
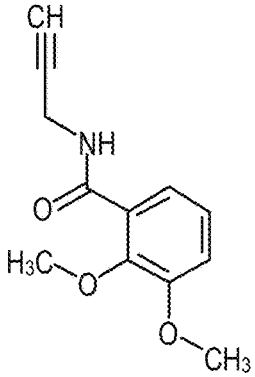
Figure 4:
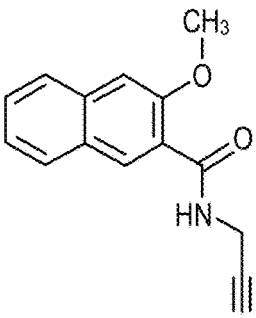
Figure 4:
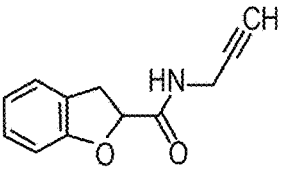
Figure 4:
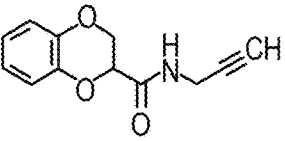
Figure 4:
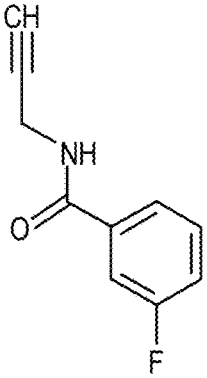
Figure 4:
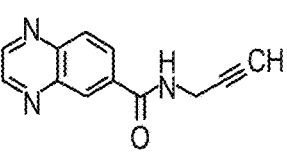
Figure 4:
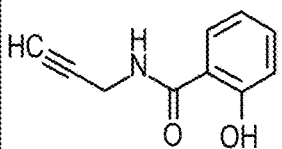
Figure 4:
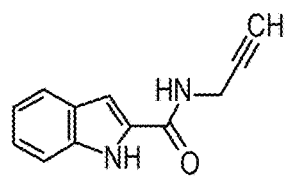
Figure 4:
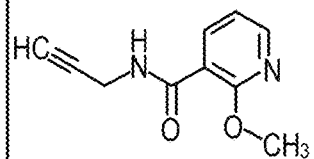
Figure 4:
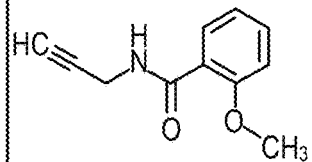
Figure 4:
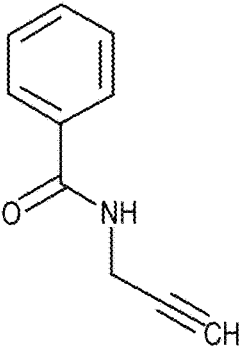
Figure 4:
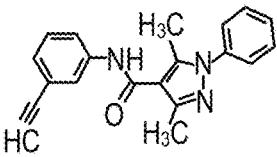
Figure 4:
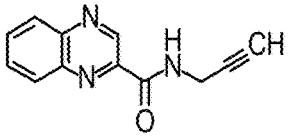
Figure 4:
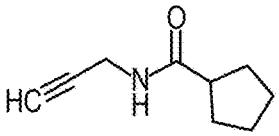
Figure 4:
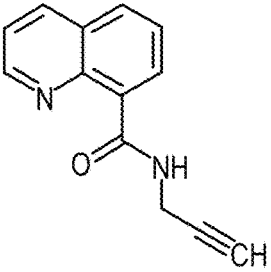
Figure 4:
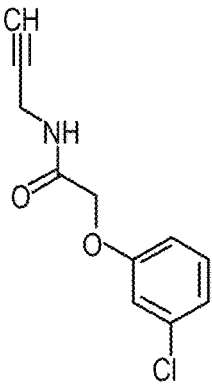
Figure 4:
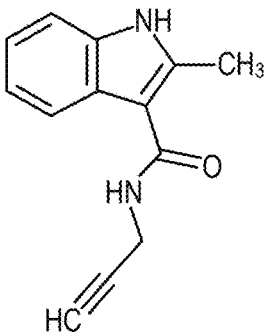
Figure 4:
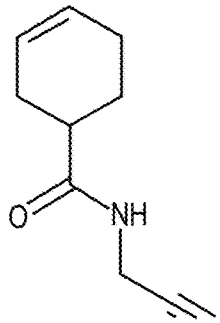
Figure 4:
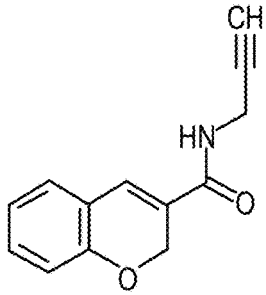
Figure 4:
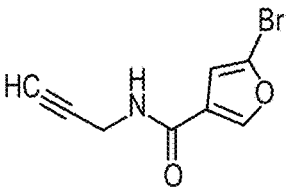
Figure 4:
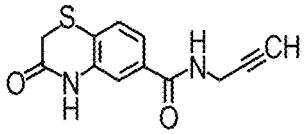
Figure 4:
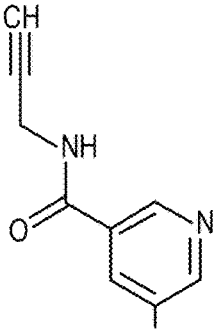
Figure 4:
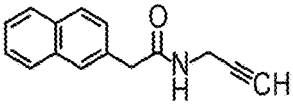
Figure 4:
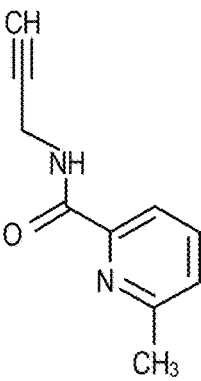
Figure 4:
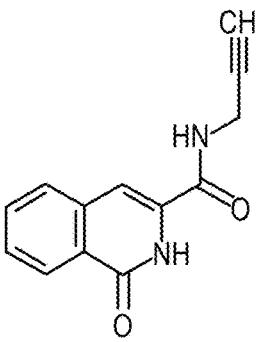
Figure 4:
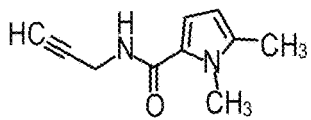
Figure 4:
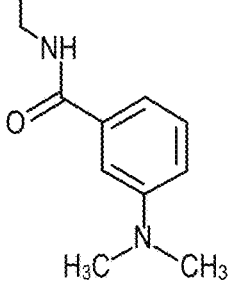
Figure 4:
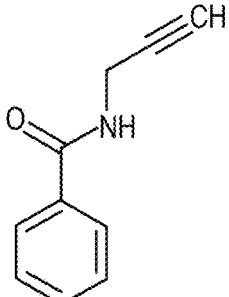
Figure 4:
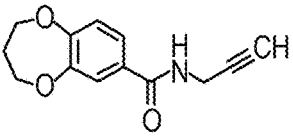
Figure 4:
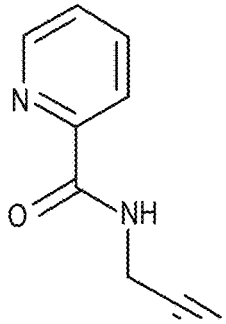
Figure 4:
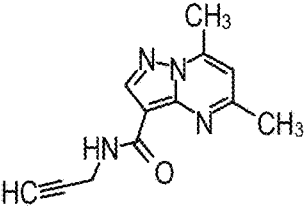
Figure 4:
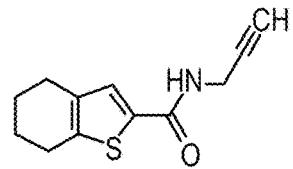
Figure 4:
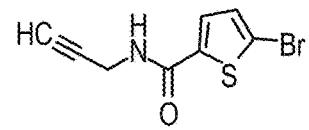
Figure 4:
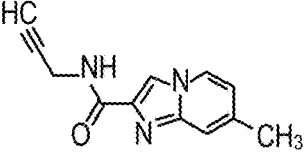
Figure 4:
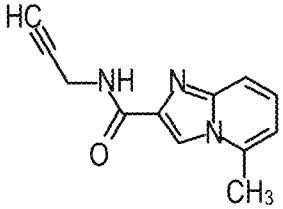
Figure 4:
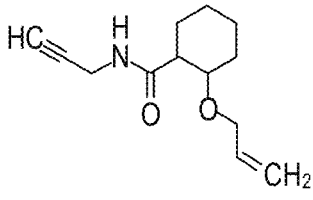
Figure 4:
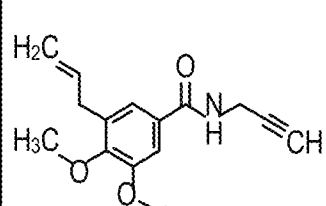
Figure 4:
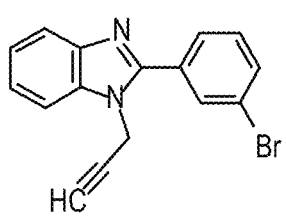
Figure 4:
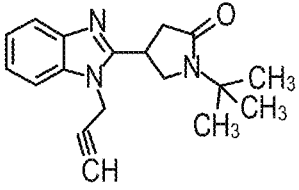
Figure 4:
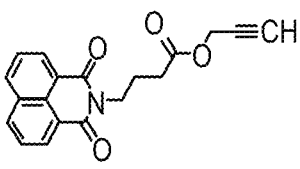
Figure 4:
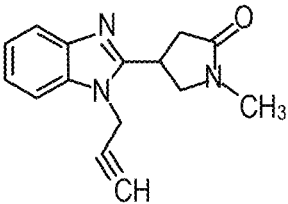
Figure 4:
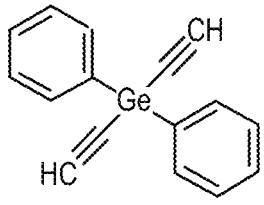

The crude reactions were diluted 100-fold for receptor-mediated phosphatase inhibition assays (~50 μM OP-4-triazole, assuming quantitative conversion) in 96-well plates and conducted as described in Example 1 (PYR1 and HAB1 at 25 nM) in a volume of 100 μL. Both ABA (5 μM) and mock PP2C controls (no ABA) were included in each plate. Duplicate measurements of %-PP2C activity were averaged and wells that enabled recovery of PP2C activity to ≥90% relative to mock PP2C control were classified as hits. A total of 204 hits were obtained and can be classified in to 10 groups based on the functional motif linked to the alkyne: propargyl amines, propynoic acid derivatives, propargyl ethers, propargyl amides, propargyl esters, propynes, propargyl thioethers, propargyl ureas, propargyl sulfonamides, and propargyl carbamates (FIG. 4), which were combined into a small library in 3 plates (plates 1-3) and retested for antagonist activity using receptors from the three receptor subfamilies: PYR1 (50 nM), PYL4 (100 nM), or PYL8 (50 nM), using assays conditions that were otherwise identical to those described in Example 1 (FIG. 5).

Example 6-LC-MS Analyses to Estimate Library Quality and Conversion Rates

Figure 5:
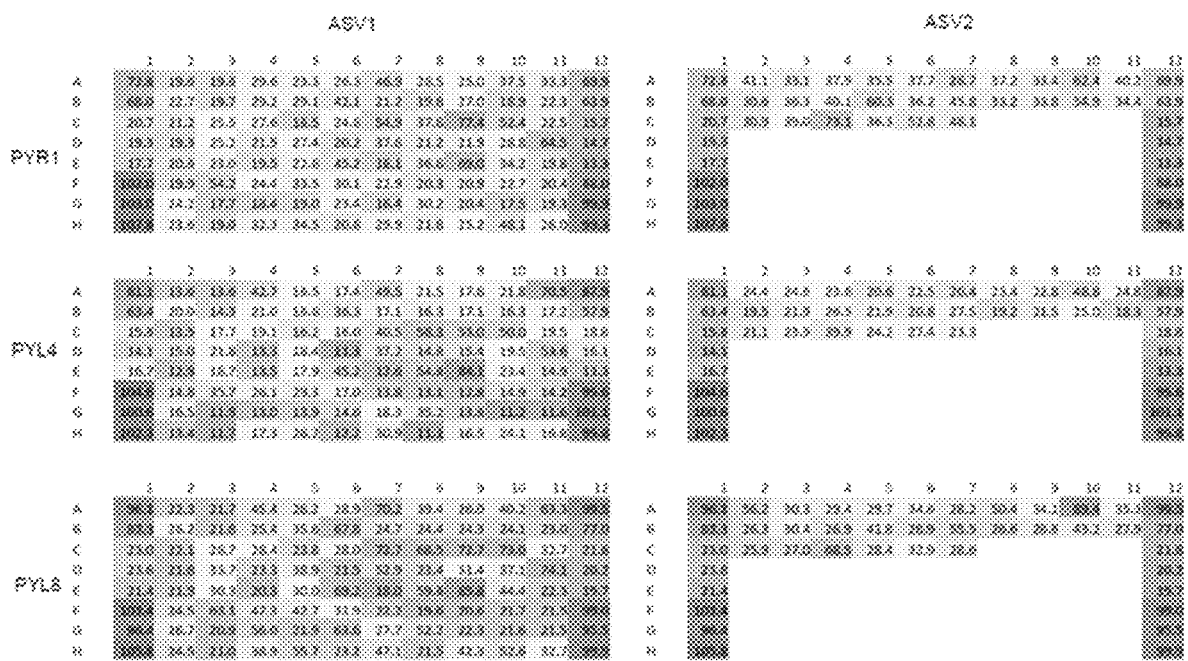
FIG. 5. OPZ conversion observed across all 10 classes of hits obtained in the initial antagonist screen with PYR1
Figure 6:
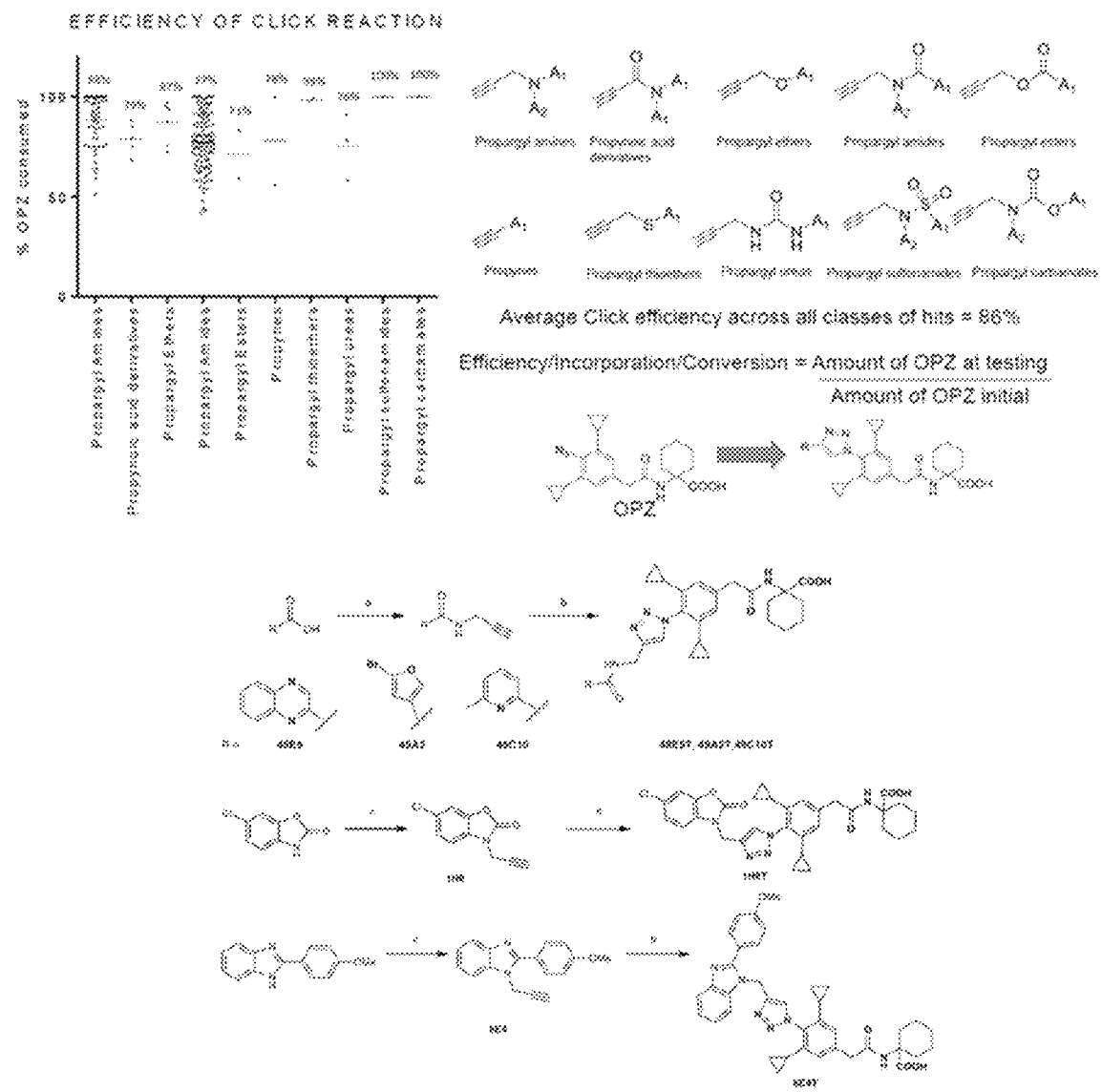
FIG. 6. Synthesis of alkynes and OP-4-triazoles. (a) Propargyl amine, EDCI, DMAP, DCM, 0° C.-RT, 12 hr. (b) OPZ, BTTA, Na ascorbate, Copper (II) sulphate, RT, 48 hr. (c) Propargyl bromide, potassium carbonate, acetone, reflux, 12 hrs.

To investigate library quality we ran high throughput LC-MS experiments to measure remaining OPZ levels for the 204 hit triazole reactions identified in Example 5 and observed an average reaction efficiency (OPZ consumption) of 86% (±11%) (FIGS. 5 and 6). High throughput LC-MS experiments were conducted as follows. Reactions were diluted to 10 μM in 1:1 acetonitrile/water (with 0.1% formic acid) and separated by liquid chromatography on an Agilent Exclipse XDB C-18, 1.8 μm particle and 2.1×50 mm column using 1.6 minute isocratic separations (59% ACN/0.1% formic acid in water) and overlapping injections from a well plate autosampler. Mass spectra were collected after LC separation on an Agilent 6224 TOF MS from electrospray ionized material in positive ion mode, using the ionization and detector settings described in Example 2. The relative amount of OPZ in each reaction was estimated by integrating area under peaks for formula-matched OPZ m/z peaks in comparison to an OPZ standard using MassHunter software.

Example 7-Reactions with Propargyl Amides Produce OP-4-Triazoles with Potent Bioactivity in Seeds To evaluate and prioritize the 204 hits obtained, we examined their effects on ABA-mediated inhibition of *Arabidopsis* seed germination and seedling growth. *Arabidopsis* seeds germinate and produce photosynthetically active cotyledons within 4-days post imbibition under illumination. Low concentrations of ABA (i.e. 1 μM) inhibit both germination and seedling growth, which is easily quantified by image analysis of green pixel counts. This provides a simple test for ABA antagonists, as they will block the inhibitory effects of ABA on greening. We used this assay to characterize the 204 hit molecules. Greening experiments were performed in 96-well polystyrene petri plates using surface sterilized *Arabidopsis* (Col) seeds plated on to 0.7% agar medium containing ½-X MS salts, 0.5% sucrose, 1 μM ABA, and one of the 204 click reactions products (~10 μM). After 4 days of stratification (4° C.), the plates were transferred to a growth chamber under continuous illumination and photographed 4 days later. Each experiment included ABA (1 μM ABA, no antagonist) and mock (no ABA) controls. The results of these experiments revealed that the most potent OP-4-triazoles resulted from click reactions with propargyl amides (FIG. 5). Combined with the in vitro PP2C data from Example 5, these data suggest that these OP-4-peptidotriazoles are active both in vitro and in vivo and were therefore selected for further characterization.

Example 8-Purified OP-4-Triazole Hits are Bioactive

To conduct more detailed analyses of compound mode of action, we performed larger scale synthesis of hit molecules, focusing on propargyl amide derived hits (48E9T, 49C10T, 49A2T), as well as a propargyl carbamate pan antagonist (1H6T) and a propargyl amine selective antagonist (6E4T). The synthetic schemes followed to produce these compounds are shown in FIG. 6. The required alkynes 48E9, 49C10 and 49 Å2 were synthesized by reacting corresponding acids (1 equiv) with propargyl amine (1 equiv), EDCI (1.5 equiv), DMAP (1.2 equiv) in anhydrous DCM at RT for 12 hr. After completions of reaction (TLC), the reaction mixture was concentrated in vacuo, adsorbed on silica, and purified by flash chromatography using a hexane/ethyl acetate gradient to produce white/off white powders in quantitative yields. The alkynes 1H6 and 6E4 were synthesized by N-alkylation of 6-chlorobenz[d]oxazol-2(3H)-one (1 equiv) or 2-(4-methoxyphenyl)-1H-benzimidazole (1 equiv) with propargyl bromide (1.5 equiv) in presence of potassium carbonate (3 equiv) in refluxing acetone for 12 hrs, purified by flash chromatography to produce white powders in quantitative yields. The group of alkynes (1 equiv) were subsequently reacted with OPZ (1 equiv) in the presence of BTTA (0.4 equiv), sodium ascorbate (0.4 equiv), and copper (II) sulphate (0.2 equiv) using DMSO/Water (4:1 v/v) as the solvents. After 48 hours at RT, the triazole reaction products were precipitated using 2N HCl, filtered, and dried as white powders in near quantitative yields.

(2-Propynylamino)(2-quinoxalinyl)formaldehyde (48E9) 4-1 NMR (700 MHz, DMSO-d6) δ ppm 3.15 (t, J=2.8 Hz, 1H), 4.15 (dd, J-2.1 Hz, J-5.6 Hz, 2H), 7.99-8.02 (m, 2H), 8.20-8.22 (m, 2H), 9.45-9.47 (m, 2H). $^{13}$C NMR (176 MHz, DMSO-d6) δ ppm 28.92, 73.41, 81.34, 129.60, 129.92, 131.84, 132.49, 140.28, 143.50, 144.15, 144.52, 163.51.

(5-Bromo-3-furyl)(2-propynylamino)formaldehyde (49 Å2)$^1$H NMR (700 MHz, DMSO-d6) δ ppm 3.15 (t, =2.8 Hz, 1H), 4.01 (dd, 0.1=2.1 Hz, 0.1=5.6 Hz, 2H), 6.94 (s, 1H), 8.27 (s, 1H), 8.70 (t, J=4.9 Hz, 1H). $^{13}$C NMR (176 MHz, DMSO-d6) δ ppm 28.38, 736.64, 81.39, 111.02, 123.34, 125.08, 147.82, 160.56.

(6-Methyl-2-pyridyl)(2-propynylamino)formaldehyde (49C10) $^1$H NMR (700 MHz, DMSO-d6) δ ppm 2.15 (s, 3H), 3.09 (t, J=2.8 Hz, 1H), 4.08 (dd, J=2.1 Hz, J=5.6 Hz, 2H), 7.46 (d, J=7.7 Hz, 1H), 7.85 (m, 2H), 8.95 (t, J=5.6 Hz, 1H). $^{13}$C NMR (176 MHz, DMSO-d6) δppm 24.29, 73.08, 81.73, 119.56, 126.66, 138.36, 149.42, 157.68, 164.25.

6-Chloro-3—(2-propynyl)-1,3-benzoxazolidin-2-one (1H6)$^1$H NMR (700 MHz, DMSO-d6) δ ppm 3.56 (t, J=2.8 Hz, 1H), 4.73 (d, J=2.8 Hz, 2H), 7.34-7.37 (m, 2H), 7.60 (m, 1H). $^{13}$C NMR (176 MHz, DMSO-d6) δ ppm 32.08, 76.55, 77.28, 111.07, 111.14, 124.48, 127.23, 129.61, 142.82, 153.27.

2—(p-Methoxyphenyl)-1—(2-propynyl)-1,3-benzimidazole (6E4))$^1$H NMR (700 MHz, DMSO-d6) δ ppm 3.51 (t, J=2.8 Hz, 1H), 3.87 (s, 3H), 5.14 (d, J=2.8 Hz, 2H), 7.16-7.18 (m, 2H), 7.27-7.33 (m, 2H), 7.66-7.70 (m, 2H), 7.81-7.83 (m, 2H). $^{13}$C NMR (176 MHz, DMSO-d6) δ ppm 34.78, 55.85, 76.54, 79.16, 111.10, 114.87, 119.49, 122.35, 122.78, 122.97, 130.94, 135.85, 142.95, 152.89, 161.02.

1-{2-[3,5-Dicyclopropyl-4—(4-{[(2-quinoxalinyl)carbonylamino]methyl}-1H-1,2,3-triazol-1-yl) phenyllacetylamino}cyclohexanecarboxylic acid (48E9T) $^1$H NMR (700 MHz, DMSO-d6) δ ppm 0.59 (m, 4H), 0.73-0.74 (m, 4H), 1.16-1.25 (m, 3H), 1.42-1.54 (m, 5H), 1.61-1.65 (m, 2H), 1.95-1.97 (m, 2H), 3.35 (s, 2H), 3.47 (s, 2H), 4.76 (d, J=5.6 Hz, 2H), 6.79 (s, 2H), 7.98-8.01 (m, 2H), 8.08 (s, 1H), 8.20-8.22 (m, 2H), 8.29 (s, 1H), 9.50 (s, 1H), 9.55 (t, J=5.6 Hz, 1H).

112—(4-{4-1(5-Bromo-3-furoylamino)methyl]-1H-1,2,3-triazol-1-yl}-3,5-dicyclopropylphenyl)acetylaminolcyclohexanecarboxylic acid (49 Å2T)$^1$H NMR (700 MHz, DMSO-d6) δ ppm 0.59 (m, 4H), 0.72-0.73 (m, 4H), 1.14-1.25 (m, 3H), 1.41-1.55 (m, 5H), 1.62-1.66 (m, 2H), 1.95-1.97 (m, 2H), 3.35 (s, 2H), 3.47 (s, 2H), 4.58 (d, J=5.6 Hz, 2H), 6.80 (s, 2H), 6.97 (d, J=1.4 Hz, 1H), 8.09 (s, 1H), 8.24 (s, 1H), 8.28 (d, J=0.7 Hz, 1H), 8.82 (t, J=5.6 Hz, 1H).

1-{2-13,5-Dicyclopropyl-4—(4-{[(6-methyl-2-pyridyl)carbonylamino[methyl}-1H-1,2,3-triazol-1-yl)phenyl-lacetylaminolcyclohexanecarboxylic acid (49C10)$^1$H NMR (700 MHz, DMSO-d6) δ ppm 0.58-0.59 (m, 4H), 0.72-0.73 (m, 4H), 1.14-1.23 (m, 3H), 1.42-1.55 (m, 5H), 1.62-1.66 (m, 2H), 1.95-1.97 (m, 2H), 2.56 (s, 3H), 3.47 (s, 2H), 4.68 (d, J=5.6 Hz, 2H), 7.46-6.80 (s, 2H), 7.46-7.48 (m, 1H), 7.86-7.89 (m, 2H), 8.09 (s, 1H), 8.24 (s, 1H), 8.28 (d, J=0.7 Hz, 1H), 9.07 (t, J=5.6 Hz, 1H).

1-[2—(4-{4-[(6-Chloro-2-oxo-1,3-benzoxazol-3-yl)methyl]-1H-1,2,3-triazol-1-yl}-3,5-dicyclopropylphenyl)acetylaminolcyclohexanecarboxylic acid (1H6T)$^1$H NMR (700 MHz, DMSO-d6) δ ppm 0.56 (m, 4H), 0.63-0.64 (m, 4H), 1.11-1.25 (m, 3H), 1.40-1.55 (m, 5H), 1.61-1.65 (m, 2H), 1.95-1.97 (m, 2H), 3.47 (s, 2H), 5.24 (s, 2H), 6.83 (s, 2H), 7.25-7.28 (m, 2H), 7.58-7.59 (m, 2H), 8.08 (s, 1H), 8.54 (s, 1H).

1-{2-13,5-Dicyclopropyl-4—(4-1[2—(p-methoxyphenyl)-1,3-benzimidazol-1-yl]methyl)-1H-1,2,3-triazol-1-yl) phenyllacetylamino)cyclohexanecarboxylic acid (6E4T)$^1$H NMR (700 MHz, DMSO-d6) δ ppm 0.55-0.60 (m, 8H), 1.03-1.25 (m, 3H), 1.43-1.54 (m, 5H), 1.61-1.65 (m, 2H), 1.95-1.97 (m, 2H), 3.47 (s, 2H), 3.92 (s, 3H), 5.92 (m, 2H), 6.84 (s, 2H), 7.32 (d, J=8.4 Hz, 2H), 7.60-7.63 (m, 2H), 7.88-7.92 (m, 1H), 8.05-8.07 (m, 1H), 8.13-8.14 (m, 2H), 8.66 (m, 1H).

Example 9-OP-4-Peptidotriazoles are Potent Antagonists In Vivo

Figure 7:
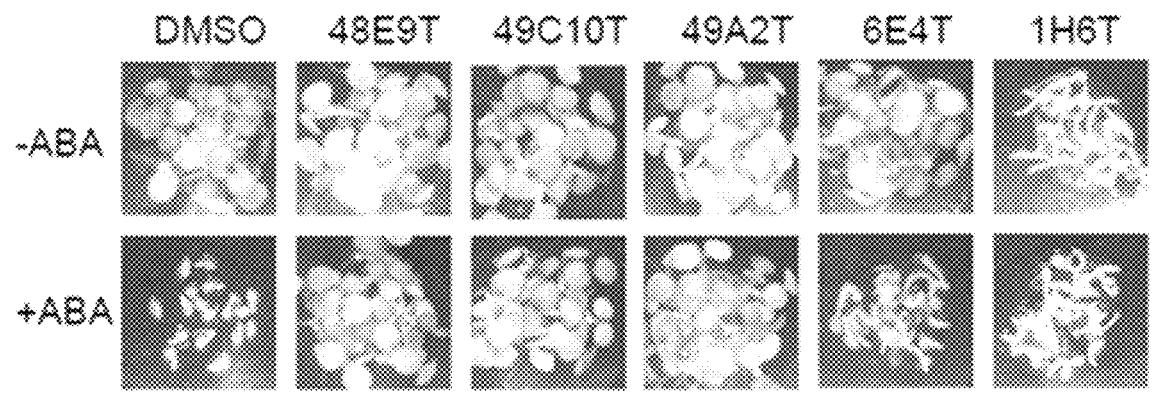
FIG. 7. OP-4-peptidotriazoles (30 µM) antagonize ABA (1 µM) effects in *Arabidopsis*.

The OP-4-triazoles 48E9T, 49C10T, 49 Å2T, 1H6T and 6E4T were tested in *Arabidopsis* greening assays at 30 μM in presence or absence of 1 μM ABA using conditions described in Example 7. These experiments confirmed that the pure OP-4-peptidotriazoles formed from alkynes of the propargyl amide class (48E9, 49C10, 49 Å2) were indeed highly effective in blocking the effects of ABA in inhibiting greening in cotyledons, whereas the PYR1-selective antagonist 6E4T was only weakly effective; the carbamate based ligand 1H6T, while weakly active, exhibited possible phytotoxicity at 30 μM. (FIG. 7). Based on these results we focused efforts on optimizing the OP-4-peptidotriazoles.

Example 10-Solid Phase Synthesis and Characterization of a Focused Combinatorial Propargyl Amide Library Our discovery of OP-4-peptidotriazoles as potent, bioactive pan-antagonists prompted us to explore the chemical space of amide substituents in an attempt to improve activity and better understand structure activity relationships. We used solid phase coupling reagents to rapidly synthesize a 106 member library of diverse aryl/heteroaryl propargyl amides by coupling diverse carboxylic acids (obtained from Combiblocks) with propargyl amine in presence of polymer supported EDCI. Reactions were carried out in a 10 mL glass vial fitted with a small stir bar. Polymer supported EDCI (2 equiv, with labeling of 1.4 mmol/g, Sigma Aldrich) was weighed into siliconized vials (coated with Sigmacote) and 2 mL of anhydrous chloroform was added to swell the resin as it was being stirred. Carboxylic acid (1 equiv) was added to the polymer suspension and the resultant mixture stirred at RT for 30 mins, after which propargyl amine (1 equiv) was added and the reaction stirred for 48 hrs at RT. The reaction mixture was subsequently filtered through a polypropylene syringe filter to separate the resin from the reaction, and the resin washed with 3 mL anhydrous chloroform. The filtrate was concentrated under vacuum to yield the crude propargyl amide, which was used directly used (without further purification) as a 10 mM stock in DMSO to react with OPZ as described in Example 4. The OP-4-peptidotriazoles formed were tested for antagonism of PYR1, PYL4, and PYL8, as described in Example 5. The structures and activity of the in situ generated triazoles is shown in FIG. 8. These experiments produced ten OP-4-peptidotriazoles with activity in the crude reactions that appeared comparable to or better than the original OP-4-peptidotriazole hits 48E9T and 49 Å2T across all three receptor subfamilies.

Figure 9:
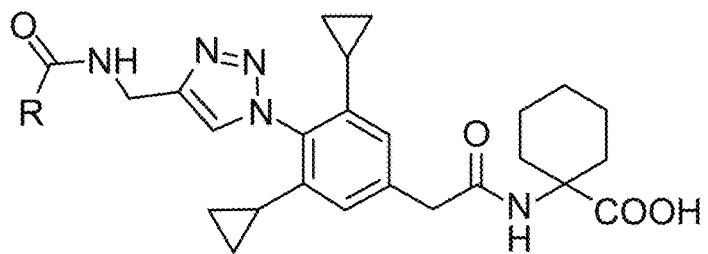
FIG. 9. Structures and analytical data for triazoles resynthesized, as determined by LC-MS as described in Example 2. LCMS analysis carried out in positive ion mode and masses indicate [M+H]+ ion FIG. 10. Antagonist potency against different *Arabidopsis* receptors, as measured using agonist/receptor-mediated inhibition of ΔN-HAB1 phosphatase activity (n=3); n.s indicates that PP2C activity was not significantly different at 50 µM test chemical in presence of 5 µM ABA (the highest concentration tested). All assays contained 50 nM receptor and 25 nM ΔN-HAB1 except PYL4 where the receptor concentration was 100 nM. Error bars indicate S. D.

Since we did not purify the amides prior to running the reactions, the hits were resynthesized using conditions similar to those adopted in Example 8 to make quantitative comparisons of activity. The structure and analytical data of resynthesized triazoles is shown in FIG. 9 below.

Example 11-Characterization of OP-4-Triazole Antagonist Selectivity

The pure OP-4-peptidotriazoles synthesized were tested for their ability to antagonize ABA-mediated receptor activation in vitro using the assay method described in Example 5. The compounds were tested for activity against recombinant PYR1, PYL4, or PYL8 at concentrations ranging from 61 nM to 100,000 nM in triplicate; $EC_{50}$ values were inferred from this data by fitting to a log(inhibitor) vs. response-(variable slope) model (GraphPad) (FIG. 10). These experiments show that ASV1E9T is a the strongest ABA receptor antagonist synthesized and that it exhibits an ~3 order of magnitude improvement in potency compared to the ABA antagonist PanMe. Moreover, these data show that AA1 does not possess detectable antagonist activity at 50 µM in vitro, as the PP2C activity observed was statistically indistinguishable from the ABA-only controls for all receptors tested (PYR1: $p=0.2$, PYL4: $p=0.7$, and PYL8: $p=0.6$), we conclude based on these data that AA1 is not an ABA receptor pan-antagonist, in contrast to previous reports. Our data show that heterobiaryl substituted head groups on the peptidotriazole made for better antagonists as compared to monoaryl/heteroaryl substituted head groups. Within the monoaryl ring systems, halo substituted furanyl/thienyl derivatives were better than pyridyl derivatives, with 2-halo substitutions preferred over 3-halo substitutions.

Figure 11:
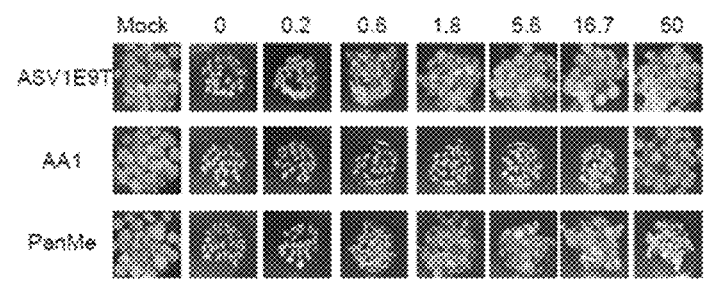
FIG. 11. The potency of different antagonists on *Arabidopsis* greening assays and their corresponding greening $EC_{50}$ values (concentrations required to restore greening to 50% of mock treated in presence of 1 µM ABA). No greening was observed with 1 µM ABA and greening for chemical treatments was normalized to mock which was treated as 100%. % germination in *Arabidopsis* germination assays in presence of 1 µM ABA and 200 nM antagonist. Mock treated controls had 100% germination, while ABA controls had an germination of 1-2%.

Example 12-Several OP-4-Triazoles are Potent ABA Antagonists in *Arabidopsis* Seed Germination/Greening Assays Purified triazoles were evaluated for their ability to block the effects of exogenous ABA in inhibiting seed germination/greening, performed as described in Example 7 using the purified OP-4-peptidotriazole hits, PanMe, AA1, and OPZ at concentrations ranging from 200 nM to 50000 nM in triplicate in presence of 1 µM ABA. Seed germination was scored at the lowest concentration tested, while greening data (normalized to mock control) was fitted to log(inhibitor) vs. response-(variable slope) model using non-linear regression to infer the $EC_{50S}$, using GraphPad Prism 6.0. These experiments show that ASV1E9T is the most potent antagonist in vivo amongst those tested (FIG. 11), whereas AA1 affects greening only at the highest concentration tested. PanMe on the other hand blocks ABA's effects at lower concentrations but was phytotoxic at higher concentrations, hence an accurate estimation of its $EC_{50}$ could not be ascertained.

Figure 12:
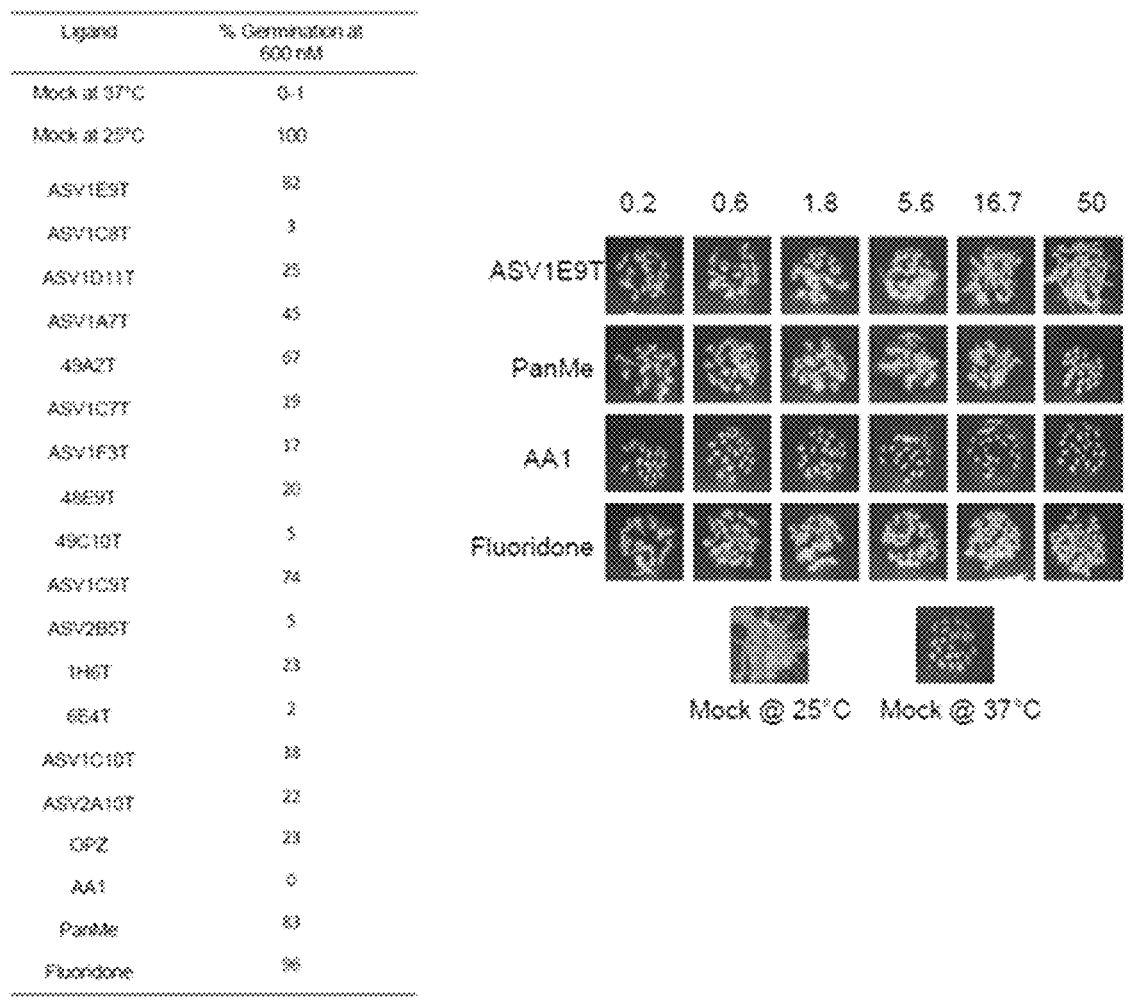
FIG. 12. Activity of antagonists in vivo, in a thermoinhibition assay. *Arabidopsis* seeds plated on 0.7% agar medium containing ½-x MS salts, 0.5% sucrose, with different doses of OP-4-peptidotriazoles, PanMe, AA1, OPZ and fluridone, an ABA biosynthetic inhibitor as a (positive control). After 4 d of stratification at 4° C., the plates were transferred to an incubation chamber at 37° C. in dark for 72 hrs. After heat treatment, the plates were placed in dark in an incubation chamber at RT for 48 hrs and photographed thereafter.

Example 13-OP-4-Peptidotriazoles Antagonize Thermoinhibition of Seed Germination Adverse environmental conditions during germination can affect dormancy in several species. For example, high temperatures during seed imbibition can prevent seed germination and induce a form of secondary seed dormancy in a process called thermoinhibition. Although thermoinhibtion is complex, elevated ABA levels induced by heat play a critical role, as evidenced by both the identification of ABA-deficient varieties of lettuce with reduced sensitivity to thermoinhibition and pharmacological experiments using fluridone, which disrupts ABA biosynthesis and thermoinhibition in many species. Chemicals that can counter this effect of heat stress could find use as seed treatments to ensure consistent germination under adverse conditions. To establish if our OP-4-peptidotriazoles block thermoinhibition, we conducted assays as follows. 96 well polystyrene petri plates with surface sterilized *Arabidopsis* seeds plated on 0.7% agar medium containing ½-x MS salts, 0.5% sucrose, and doses spanning from 0.2 µM to 50 µM of different OP-4-peptidotriazoles, PanMe, AA1, OPZ and fluridone as a positive control. After 4 d of stratification at 4° C., the plates were transferred to an incubation chamber at 37° C. in dark for 72 hrs. After heat treatment, the plates were placed in dark in an incubation chamber at RT for 48 hrs and photographed. These experiments revealed that several OP-4-peptidetriazoles block thermoinhibition (ASV1E9T, ASV1C9T, 49 Å2T). PanMe blocks thermoinhibition but its effects decreased at higher concentrations, whereas fluridone blocks thermoinhibition at all concentrations tested (FIG. 12). AA1 was inactive in this assay, consistent with it having a mechanism of action not involving direct antagonism of ABA receptor activity.

Example 14-OP-4-Peptidotriazoles Block ABA Effects on Primary Root Growth

Purified triazoles were evaluated for their ability to block effects of exogenous ABA in inhibiting primary root growth in *Arabidopsis* seedlings. *Arabidopsis* seeds were surface sterilized and plated on 0.7% agar medium containing ½-x MS salts, 0.5% sucrose. After 4 d of stratification at 4° C., transferred to dark chamber for 48 hrs. 5-6 seedlings at this stage were transferred to chemical plates containing purified triazole hits, PanMe, AA1 and OPZ at 5 and 10 µM in triplicate in presence of 10 µM ABA. Additional ABA controls (10 µM ABA, no antagonist) were also performed to assess effects of ABA on growth in absence of antagonist and transferred to dark chamber at RT for 72 hrs. Root lengths were measured and normalized to mock controls (FIG. 13). These experiments revealed that ASV1E9T was the most potent antagonist amongst all the chemicals tested and PanMe and AA1 exhibited weak effects under these conditions.

Example 15-OP-4-Triazole Block ABA Induced Gene Expression

Figure 14:
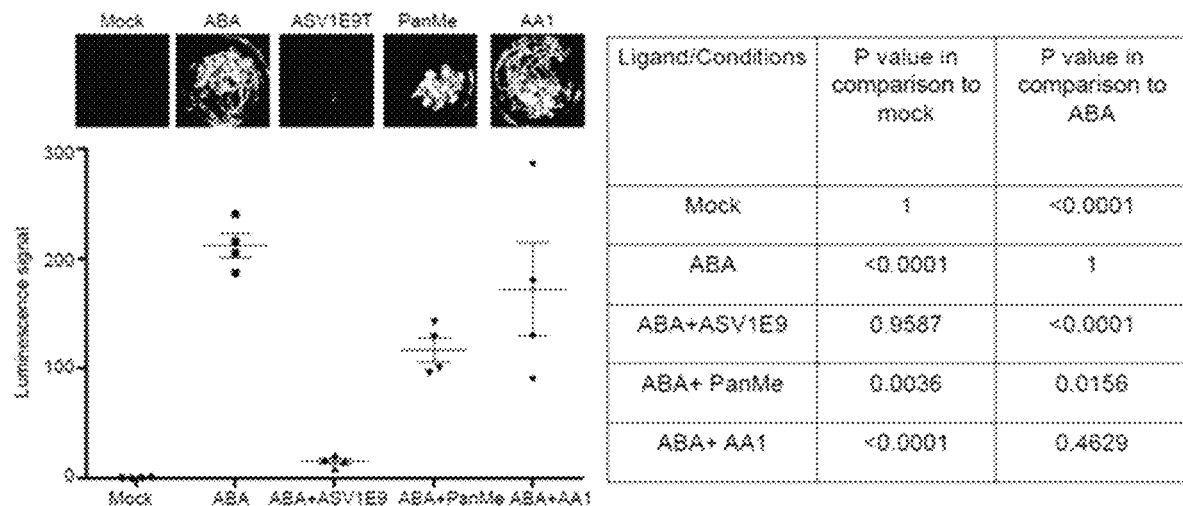
FIG. 14. Activity of antagonists in vivo, as measured using a luciferase-based assay. Antagonist activity was measured using 10 day old *Arabidopsis thaliana* transgenic seeds; each well contains 20-30 seedlings per well and was treated with 25 µM of test chemicals and 25 µM ABA or a mock control. Luminescence images were captured 6-hours post-treatment. The grey scale images were converted to false color in Photoshop (left) and luminescence quantified using ImageJ. Error bars represent standard error of mean for quadruplicate treatments. Values in the adjacent table represent p-value comparison to mock and ABA treated control using one-way ANOVA and post-hoc Dunnett's test.

ASV1E9T, PanMe, AA1 and OPZ were evaluated for their ability to block effects of exogenous ABA in inducing MAPKKK18 gene expression in *Arabidopsis* seedlings. *Arabidopsis* seeds (MAPKKKI8::Luc reporter line) were surface sterilized grown and plant growth liquid medium (½ Murashige and Skoog medium and 0.5% Sucrose) under 16 hour light and 8 hour dark conditions. 10 day old seedlings were transferred to new plant growth liquid medium with test chemical at 25 µM in presence of equimolar concentration of ABA and 100 µM luciferin. Luciferase assay image were taken by XYZ camera after 6 hr of treatments. The average luminescent intensity was quantified using ImageJ. Average intensity was calculated for quadruplicates and the error bars on graphs represent the standard error of mean. These experiments revealed that ASV1E9T potently blocked ABA induced MAPKKK18::Luc gene expression whereas PanMe was less effective under these conditions and AA1 was not significantly different than the control. (FIG. 14)

Example 16-ASV1E9 Antagonizes ABA's Effects on Transpiration

Figure 15:
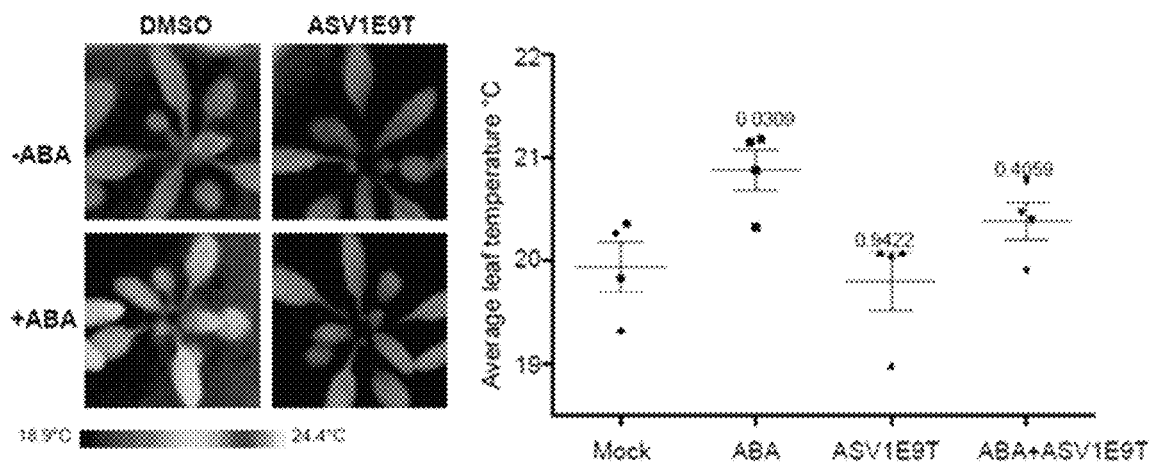
FIG. 15. Representative infrared images of *Arabidopsis* plants treated with 10 μM test chemicals and quantification of leaf temperature at 24 hrs, error bars indicate SEM. The values shown above the error bars indicate the p-value for comparison with the mock for each chemical treatment using one way ANOVA using Dunnett's test.

Seeds from Col-0 were surface sterilized in bleach and plated onto 0.5×MS, 0.5% sucrose agar medium. 3-5 day old seedlings were then transferred from agar plates to soil and grown on 16 hour days for 3 weeks. Plants were treated by foliar spraying with a aqueous solutions of 0.1% DMSO carrier solvent, 0.02% Silwet-77 surfactant (Lehle seeds), and antagonist ASV1E9T from 10 µM (5 mL/pot) in presence of absence of 10 µM of ABA. Thermographs were collected with a FLIR camera (T62101) 24 hours after compound applications and quantified using the FLIR camera software by measuring the average leaf temperature of 5 or 6 leaves per plant. Average leaf temperatures were calculated for 4 replicate plants (in 4 pots) per treatment. Statistical comparisons between treated and the mock treated plants were performed using one way ANOVA-Dunnett's test. These experiments revealed that ASV1E9T suppresses the effects of exogenous application of ABA (FIG. 15).

Example 17-ASV1E9 Antagonizes ABA's Effects on Transpiration

Seeds from Col-0 were surface sterilized in bleach and plated onto 0.5×MS, 0.5% sucrose agar medium. 3-5 day old seedlings were then transferred from agar plates to soil and grown on 16 hour days for 3 weeks. Plants were treated by foliar spraying with a aqueous solutions of 0.1% DMSO carrier solvent, 0.02% Silwet-77 surfactant (Lehle seeds), and antagonist ASV1E9T from 10 µM (5 mL/pot) in presence of absence of 10 µM of ABA. Thermographs were collected with a FLIR camera (T62101) 24 hours after compound applications and quantified using the FUR camera software by measuring the average leaf temperature of 5 or 6 leaves per plant. Average leaf temperatures were calculated for 4 replicate plants (in 4 pots) per treatment. Statistical comparisons between treated and the mock treated plants were performed using one way ANOVA-Dunnett's test. These experiments revealed that ASV1E9T suppresses the effects of exogenous application of ABA (FIG. 15).

1-[2-(4-Azido-3-cyclopropylphenyl)acetylamino]cyclohexanecarboxylic acid (3CBZ) $^1$H NMR (700 MHz, DMSO-d6) δ ppm 0.61-0.64 (m, 2H), 0.92-0.95 (m, 2H), 1.18-1.24 (m, 3 H), 1.36-1.53 (m, 5H), 1.59-1.63 (m, 2H), 1.92-1.94 (m, 2H), 1.98-2.01 (m, 2H), 3.40 (s, 2H), 6.86 (s, 1H), 7.11-7.15 (m, 2H), 8.00 (s, 1H).

1-{2-[3-Cyclopropyl-4—(4-{[(2-quinoxalinyl)carbonylamino]methyl}-1H-1,2,3-triazol-1-yl)phenyl]acetylamino}cyclohexanecarboxylic acid (3CB-48E9T)$^1$H NMR (700 MHz, DMSO-d6) δppm 0.62-0.64 (m, 2H), 0.83-0.87 (m, 4H), 1.42-1.5 (m, 5H), 1.60-1.63 (m, 3H), 1.94-1.96 (m, 2H), 3.34 (s, 1H), 3.53 (s, 2H), 4.76 (d, J=5.6 Hz, 2H), 7.30-731 (m, 1H), 7.21-7.22 (m, 1H), 7.01 (s, 1H), 7.99-8.01 (m, 2H), 8.11 (s, 1H), 8.21-8.22 (m, 2H), 8.34 (s, 1H), 9.50 (s, 1H), 9.56 (t, J=5.6 Hz, 1H).

It is understood that the examples and embodiments described herein are for illustrative purposes only. Various modifications or changes in light thereof will be suggested to persons skilled in the art and are to be included within the spirit and purview of this application and the scope of the appended claims. All publications, sequence accession numbers, patents, and patent applications cited herein are hereby incorporated by reference in their entirety for all purposes, including U.S. Provisional Application No. 62/691,534 (filed Jun. 28, 2018).

REFERENCES

1. S. R. Cutler, P. L. Rodriguez, R. R. Finkelstein, S. R. Abrams, Abscisic Acid: Emergence of a Core Signaling Network. *Annu. Rev. Plant Biol.* 61, 651-679 (2010).
2. S.-Y. Park et al., Abscisic acid inhibits type 2C protein phosphatases via the PYR/PYL family of START proteins. *Science.* 324, 1068-1071 (2009).
3. Y. Ma et al., *Regulators of PP2C phosphatase activity function as abscisic acid sensors. Science.* 324, 1064-1068 (2009).
4. T. Umezawa et al., Type 2C protein phosphatases directly regulate abscisic acid-activated protein kinases in *Arabidopsis. Proc. Natl. Acad. Sci.* U S. A. 106, 17588-17593 (2009).
5. F.-F. Soon et al., Molecular mimicry regulates ABA signaling by SnRK2 kinases and PP2C phosphatases. *Science.* 335, 85-88 (2012).
6. M. Okamoto et al., Activation of dimeric ABA receptors elicits guard cell closure, ABA-regulated gene expression, and drought tolerance. *Proc. Natl. Acad. Sci. U.S.A* 110, 12132-12137 (2013).
7. M.-J. Cao et al., Combining chemical and genetic approaches to increase drought resistance in plants. *Nat. Commun.* 8, 1183 (2017).
8. A. S. Vaidya et al., A Rationally Designed Agonist Defines Subfamily ILEA Abscisic Acid Receptors As Critical Targets for Manipulating Transpiration. *ACS Chem. Biol.* 12, 2842-2848 (2017).
9. J. Frackenpohl et al., Potent Analogues of Abscisic Acid—Identifying Cyano-Cyclopropyl Moieties as Promising Replacements for the Cyclohexenone Headgroup. *Eur. J. Org. Chem.* 2018, 1416-1425 (2018).
10. J. Frackenpohl et al., Use of substituted isoquinolinones, isoquinolindiones, isoquinolintriones and dihydroisoquinolinones or in each case salts thereof as active agents against abiotic stress in plants. *US Patent* (2015), (available at https://patentimages.storage.googleapis.com/85/bf/14/6a7bab7007eff7/U.S. Pat. No. 9,173,395.pdf).
11. S. R. Cutler, S. V. Wendeborn, P. J. Jung, M. D. Lachia, R. Dumeunier, Compounds that induce aba responses. US Patent (2016), (available at https://patentimages.storage.googleapis.com/3c/8e/a5/53ecd16d2042a7/US20160280651A1.pdf).
12. S. R. Cutler, M. Okamoto, Synthetic compounds for vegetative ABA responses. US Patent (2016), (available at https://patentimages.storage.googleapis.com/0d/77/e5/b485cd4b65b762/U.S. Pat. No. 9,345,245.pdf).
13. W. Dejonghe, M. Okamoto, S. R. Cutler, Small Molecule Probes of ABA Biosynthesis and Signaling. *Plant Cell Physiol.* 59, 1490-1499 (2018).
14. M. D. Lachia et al., 2-oxo-3,4-dihydroquinoline compounds as plant growth regulators. US Patent (2018), (available at https://patentimages.storage.googleapis.com/02/4b/ee/fc4a6a0f677484/US20180044297A1. pdf).
15. J. Frackenpohl et al., Use of substitute oxo tetrahydroquinoline sulfonamides or salts thereof for raising stress tolerance of plants. *US Patent* (2017), (available at https://patentimages.storage.googleapis.com/0d/e0/59/3fb3cd32900682/US20170027172A1.pdf).
16. J. Frackenpohl et al., Use of substituted dihydrooxindolylsulfonamides, or the salts thereof, for increasing the stress tolerance of plants. *US Patent* (2016), (available at https://patentimages.storage.googleapis.com/cb/6e/25/842328f2b2cbef/US20160237035A1. pdf).
17. J. Frackenpohl et al., Substituted 1-cycloalkyl-2-oxotetrahydroquinolin-6-ylsulfonamides or salts thereof and use thereof to increase stress tolerance in plants. *US Patent* (2018), (available at https://patentimages.storage.googleapis.com/6d/43/e5/67ddOad006b0f2/US20180020662A1.pdf).
18. J. Frackenpohl, L. Willms, J. Dittgen, Substituted cyano cycloalkyl penta-2, 4-dienes, cyano cycloalkyl pent-2-en-4-ynes, cyano heterocyclyl penta-2, 4-dienes and cyano heterocyclyl pent-2-en-4-ynes as . . . . US Patent App. 15 (2017), (available at https://patents.google.com/patent/US20170210701A1/en).
19. J. Frackenpohl et al., Aryl—and hetarylsulfonamides as active ingredients against abiotic plant stress. *US Patent* (2011), (available at https://patentimages.storage.googleapis.com/a7/2d/ea/8a60a636e4fdd7/US20110230350A1. pdf).
20. S. R. Cutler, M. D. Lachia, S. V. Wendeborn, C. R. A. Godfrey, D. Sabbadin, Carbamate quinabactin. World Patent (2018), (available at https://patentimages.storage.googleapis.com/65/27/d8/68509d60cc0199/WO2018017490A1.pdf).
21. C. R. A. Godfrey, M. D. Lachia, S. V. Wendeborn, D. Sabbadin, Plant growth regulator compounds. World Patent (2018), (available at https://patentimages.storage.googleapis.com/87/fd/61/816a6c284d84f1/WO2018007217A1. pdf).
22. S. R. Cutler, S. V. Wendeborn, O. Loiseleur, M. D. Lachia, D. Sabbadin, Derivatives of halo quinabactin. US Patent (2018), (available at https://patentimages.storage.googleapis.com/af/59/c9/c06faa2b 1d5db6/US20180312470A1. pdf).
23. J. Takeuchi et al., Designed abscisic acid analogs as antagonists of PYL-PP2C receptor interactions. *Nat. Chem. Biol.* 10, 477-482 (2014).
24. J. Takeuchi, T. Ohnishi, M. Okamoto, Y. Todoroki, Conformationally restricted 3'-modified ABA analogs for controlling ABA receptors. *Org. BiomoL Chem.* 13, 4278-4288 (2015).
25. J. Takeuchi et al., Structure-Based Chemical Design of Abscisic Acid Antagonists That Block PYL-PP2C Receptor Interactions. *ACS Chem. Biol.* 13, 1313-1321 (2018).
26. Y. Mikame et al., Synthesis of All Stereoisomers of RK460 and Evaluation of Their Activity and Selectivity as Abscisic Acid Receptor Antagonists. *Chemistry*. 25, 3496-3500 (2019).
27. Y. Ye et al., A Novel Chemical Inhibitor of ABA Signaling Targets All ABA Receptors. *Plant Physiol.* 173, 2356-2369 (2017).

The invention claimed is:
1. A compound of Formula I:

$$\text{(I)}$$

[Structure showing a pyridine/pyrimidine ring with substituents $R^{5a}$, $R^{4a}$, $R^{4b}$, $R^{5b}$, connected via L to Y-NH-C($R^{2a}$)($R^{2b}$)-$CO_2R^3$, and a triazole ring with $R^{6a}$, $R^{6b}$, $R^1$-Z substituents]

or a salt thereof;
wherein
$R^1$ is a heterocyclic, aryl, or heteroaryl group, optionally substituted with from 1 to 4 $R^9$ groups;
L is selected from the group consisting of a single bond, $-(O)_m-CH_2-$, and $-(O)_m-CH(R^{10})-$;
m is an integer selected from the group consisting of 0 and 1;
Y is $-C(O)-$ or $-S(O)_2-$;
Z is a single bond or $-C(O)-NR^7-$;
$R^{2a}$ and $R^{2b}$ are each independently selected from the group consisting of hydrogen and $R^{10}$, wherein at most one of $R^{2a}$ or $R^{2b}$ is hydrogen; or, alternatively, $R^{2a}$ and $R^{2b}$ join to form a four—to seven-membered carbocyclic or heterocyclic ring, optionally substituted with from 1 to 4$R^9$ groups;
$R^3$ is selected from the group consisting of hydrogen, $R^{10}$, and $C_{7-11}$ arylalkyl, optionally substituted with from 1 to 4 $R^9$ groups;
$R^{4a}$ and $R^{4b}$ are each independently selected from the group consisting of N and CH;
$R^{5a}$ and $R^{5b}$ are selected from the group consisting of hydrogen, $C_{1-3}$ alkyl, $C_{3-5}$ cycloalkyl, $C_{1-3}$ haloalkyl, $C_{1-3}$ alkoxy, $C_{1-3}$ haloalkoxy, $C_{1-3}$ hydroxyalkyl, halo, hydroxyl, cyano, amino, $-(CO)OH$, $-(CO)(O-C_{1-6}$ alkyl), $-(CO)NH_2$, and$-(CO)NH(R^{10})$; and wherein at least one of $R^{5a}$ and $R^{5b}$ is $C_{3-5}$ cyclopropyl;
$R^{6a}$ and $R^{6b}$ are independently selected from the group consisting of hydrogen, $C_{1-3}$ alkyl, $C_{3-5}$ cycloalkyl, $C_{1-3}$ haloalkyl, $C_{1-3}$ alkoxy, $C_{1-3}$ haloalkoxy, $C_{1-3}$ hydroxyalkyl, halo, hydroxyl, cyano, amino, $-(CO)OH$, $-(CO)(O-C_{1-6}$ alkyl), $-(CO)NH_2$; or, alternatively, $R^{6a}$ and $R^{6b}$ join to form a four- to seven-membered carbocyclic or heterocyclic ring, optionally substituted with from 1 to 4 $R^9$ groups and $-(CO)NH(R^{10})$;
each $R^7$ is independently selected from the group consisting of hydrogen, $C_{1-3}$ alkyl, $C_{3-5}$ cycloalkyl, $C_{1-3}$ haloalkyl, $C_{1-3}$ hydroxyalkyl, and $C_{4-5}$ cycloalkylalkyl;

each R⁹ is independently selected from the group consisting of $C_{1-6}$ alkyl, $C_{3-6}$ cycloalkyl, $C_{1-6}$ haloalkyl, $C_{1-6}$ alkoxy, $C_{1-6}$ haloalkoxy, $C_{1-6}$ hydroxyalkyl, halo, hydroxyl, cyano, amino, —(CO)OH, —(CO)(O—$C_{1-6}$ alkyl), —(CO)NH₂, —O(CO)R⁷, and —NH(CO)R⁷;

each R¹⁰ is independently selected from the group consisting of $C_{1-6}$ alkyl, optionally substituted with 1 to 4 R¹² groups;

each R¹¹ is independently selected from the group consisting of $C_{1-6}$ alkyl, $C_{7-11}$ arylalkyl, and $C_{4-10}$ heteroaryllalkyl, wherein said R¹¹ is further substituted with 1 to 4 R¹¹ groups; and each R¹² is independently selected from the group consisting of $C_{1-6}$ alkyl, $C_{3-6}$ cycloalkyl, $C_{1-6}$ haloalkyl, $C_{1-6}$ alkoxy, $C_{1-6}$ haloalkoxy, $C_{1-6}$ hydroxyalkyl, halo, hydroxyl, cyano, amino, —(CO)NH₂, —(CO)NH($C_{1-6}$ alkyl), —(CO)OH, —(CO)(O—$C_{1-6}$ alkyl), —(CO)NH₂, $C_{6-10}$ aryl, and $C_{2-9}$ heteroaryl.

2. The compound of claim 1, wherein L is a single bond or —CH₂—.

3. The compound of claim 1, wherein Y is —C(=O)—.

4. The compound of claim 1, wherein Z is —C(=O)—NH—.

5. The compound of claim 1, wherein R¹ is an aryl group.

6. The compound of claim 1, wherein R¹ is or a heteroaryl group.

7. The compound of claim 1, wherein $R^{2a}$ and $R^{2b}$ join to form a spirocyclohexyl or spirocyclopentyl group, optionally substituted with from 1 to 4 R⁹ groups.

8. The compound of claim 1, wherein R³ is hydrogen.

9. The compound of claim 1, wherein $R^{4a}$ and $R^{4b}$ are CH.

10. The compound of claim 1, wherein $R^{5a}$ and $R^{5b}$ are selected from the group consisting of hydrogen, $C_{1-3}$ alkyl, $C_{3-5}$ cyclopropyl, $C_{1-3}$ haloalkyl, $C_{1-3}$ alkoxy, and $C_{1-3}$ haloalkoxy.

11. The compound of claim 1, wherein $R^{6a}$ and $R^{6b}$ are hydrogen.

12. The compound of claim 1, wherein each R⁷ is independently selected from the group consisting of hydrogen, $C_{1-3}$ alkyl, and $C_{1-3}$ haloalkyl.

13. The compound of claim 1, wherein each R⁷ is hydrogen.

14. The compound of claim 1, wherein the group:

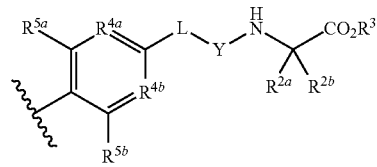

is selected from the group consisting of:

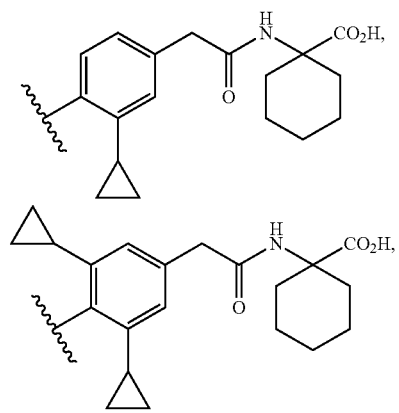

and a salt thereof.

15. An agricultural chemical formulation formulated for contacting to plants, the agricultural formulation comprising a carrier and the compound of claim 1.

16. A method of enhancing seed germination in a plant, the method comprising contacting a seed with a sufficient amount of the formulation of claim 15 to enhance germination.

17. A method of enhancing transpiration in a plant, the method comprising contacting the plant with a sufficient amount of the compound of claim 1 to enhance transpiration.

18. A method of antagonizing ABA receptor activity in a plant, the method comprising contacting the plant with a sufficient amount of the compound of claim 1.

19. A method of enhancing photosynthesis in a plant, the method comprising contacting the plant with a sufficient amount of the compound of claim 1.

* * * * *